US010532020B2

(12) United States Patent
Valia et al.

(10) Patent No.: US 10,532,020 B2
(45) Date of Patent: Jan. 14, 2020

(54) NAIL COATINGS HAVING ENHANCED ADHESION

(71) Applicant: Creative Nail Design, Inc., Vista, CA (US)

(72) Inventors: David Valia, San Diego, CA (US); Jamie Ellis, Vista, CA (US)

(73) Assignee: Revlon Consumer Products Corporation, New York, NY (US)

( * ) Notice: Subject to any disclaimer, the term of this patent is extended or adjusted under 35 U.S.C. 154(b) by 0 days.

(21) Appl. No.: 15/348,266

(22) Filed: Nov. 10, 2016

(65) Prior Publication Data

US 2017/0056313 A1  Mar. 2, 2017

Related U.S. Application Data

(63) Continuation-in-part of application No. 14/786,491, filed as application No. PCT/US2014/035028 on Apr. 22, 2014, now Pat. No. 9,713,585, and a continuation-in-part of application No. 13/827,483, filed on Mar. 14, 2013, now abandoned.

(60) Provisional application No. 61/814,691, filed on Apr. 22, 2013, provisional application No. 61/692,096, filed on Aug. 22, 2012.

(51) Int. Cl.
*A61K 8/00* (2006.01)
*A61Q 3/02* (2006.01)
*A61K 8/73* (2006.01)

(52) U.S. Cl.
CPC .............. *A61K 8/731* (2013.01); *A61Q 3/02* (2013.01); *A61K 2800/95* (2013.01)

(58) Field of Classification Search
CPC .. A61K 2800/95; A61K 8/731; A61K 8/8152; A61K 8/891; A61K 2800/43; A61K 2800/594; A61K 2800/884; A61K 8/36; A61K 8/37; A61K 8/375; A61K 8/585; A61K 8/8129; A61K 8/8135; A61K 8/8147; A61K 8/85; A61K 8/87; A61Q 3/02; A45D 29/11
See application file for complete search history.

(56) References Cited

U.S. PATENT DOCUMENTS

| | | |
|---|---|---|
| 364,467 A | 6/1887 | Baum |
| 541,482 A | 6/1895 | Grove |
| 766,335 A | 8/1904 | Farnsworth |
| 838,648 A | 12/1906 | Robertson |
| 2,465,188 A | 3/1949 | Barry et al. |
| 3,438,796 A | 4/1969 | Hanke et al. |
| 4,410,570 A | 10/1983 | Kreuzer et al. |
| 4,434,010 A | 2/1984 | Ash |
| 4,871,534 A | 10/1989 | Montgomery |
| 4,930,866 A | 6/1990 | Berning et al. |
| 5,047,492 A | 9/1991 | Weidner et al. |
| 5,118,495 A | 6/1992 | Nafziger et al. |
| 5,130,125 A | 7/1992 | Martin et al. |
| 5,171,363 A | 12/1992 | Moffat |
| 5,302,379 A | 4/1994 | Sojka |
| 5,356,616 A * | 10/1994 | Sojka ..................... A61Q 3/02 424/61 |
| 5,389,726 A | 2/1995 | Sojka |
| 5,484,867 A | 1/1996 | Lichtenhan et al. |
| 5,512,272 A | 4/1996 | Krzysik |
| 5,512,273 A | 4/1996 | Martin |
| 5,569,535 A | 10/1996 | Phillips et al. |
| 5,576,509 A | 11/1996 | Refouvelet et al. |
| 5,589,562 A | 12/1996 | Lichtenhan et al. |
| 5,607,904 A | 3/1997 | Jarrett |
| 5,624,486 A | 4/1997 | Schmid et al. |
| 5,639,447 A | 6/1997 | Patel |
| 5,643,555 A | 7/1997 | Collin et al. |
| 5,658,976 A | 8/1997 | Carpenter et al. |
| 5,662,891 A | 9/1997 | Martin |
| 5,676,938 A | 10/1997 | Kimura et al. |
| 5,688,494 A | 11/1997 | Graves et al. |
| 5,720,804 A | 2/1998 | Martin |
| 5,750,741 A | 5/1998 | Crocker et al. |
| 5,785,958 A | 7/1998 | Sirdesai et al. |

(Continued)

FOREIGN PATENT DOCUMENTS

| | | |
|---|---|---|
| EP | 0 432 572 | 6/1991 |
| FR | 2 939 661 | 6/2010 |

(Continued)

OTHER PUBLICATIONS

Ayandele et al. Polyhedral Oligomeric Silsesquioxane (POSS)-Containing Polymer Nanocomposites (review). Nanomaterials 2012, 2, 445-475.*
EP0409_Product Information by Hibrid the creators of POSS. 2015. 1 page.*
EP0408_Product Information by Hibrid the creators of POSS. 2015. 1 page.*
U.S. Appl. No. 61/629,096, filed Aug. 22, 2012, Valia et al.
International Search Report and Written Opinion dated Nov. 12, 2014, issued in International Application No. PCT/US2013/035798.
International Search Report and Written Opinion dated Sep. 9, 2014, issued in International Application No. PCT/US2014/035028.

(Continued)

*Primary Examiner* — Robert A Wax
*Assistant Examiner* — Olga V. Tcherkasskaya
(74) *Attorney, Agent, or Firm* — Dorsey & Whitney LLP

(57) ABSTRACT

The present embodiments relate to a nail coating having a major advantage in that it enables a nail coating to adhere to a natural nail or uncoated nail for long wear periods without adhesion loss or other signs of breakdown of the coating. Nail topcoats with improved abrasion resistance are also disclosed. Adhesion of a composition for nail coatings be improved by addition of a polyhedral oligomeric silsesquioxane (POSS). Nail coating compositions that benefit from the addition of a POSS include enamels, reactive composition such as those containing acrylates, solventless compositions and water-based compositions.

13 Claims, No Drawings

(56) References Cited

U.S. PATENT DOCUMENTS

| | | | |
|---|---|---|---|
| 5,858,544 A | 1/1999 | Banaszak Holl et al. | |
| 5,939,576 A | 8/1999 | Lichtenhan et al. | |
| 5,942,638 A | 8/1999 | Lichtenhan et al. | |
| 5,965,147 A | 10/1999 | Steffier | |
| 5,985,951 A * | 11/1999 | Cook | A61K 8/731 |
| | | | 424/401 |
| 6,051,242 A | 4/2000 | Patel et al. | |
| 6,100,417 A | 8/2000 | Lichtenhan et al. | |
| 6,127,557 A | 10/2000 | Van Santen et al. | |
| 6,207,364 B1 | 3/2001 | Takamuki et al. | |
| 6,252,030 B1 | 6/2001 | Zank et al. | |
| 6,254,878 B1 | 7/2001 | Bednarek et al. | |
| 6,270,561 B1 | 8/2001 | Nguyen | |
| 6,277,451 B1 | 8/2001 | Mehl et al. | |
| 6,280,756 B1 | 8/2001 | Ramin et al. | |
| 6,333,025 B2 | 12/2001 | Ramin | |
| 6,362,279 B2 | 3/2002 | Lichtenhan et al. | |
| 6,372,843 B1 | 4/2002 | Barruel et al. | |
| 6,425,936 B1 | 7/2002 | Sammons et al. | |
| 6,486,254 B1 | 11/2002 | Barbee et al. | |
| 6,489,079 B1 | 12/2002 | Verschueren et al. | |
| 6,653,365 B2 | 11/2003 | Jia | |
| 6,716,919 B2 | 4/2004 | Lichtenhan et al. | |
| 6,759,460 B2 | 7/2004 | Kamo et al. | |
| 6,818,207 B1 | 11/2004 | Schoon et al. | |
| 6,927,270 B2 | 8/2005 | Lichtenhan et al. | |
| 6,939,551 B2 | 9/2005 | Amato et al. | |
| 6,991,782 B2 | 1/2006 | Kanji et al. | |
| 7,011,821 B2 | 3/2006 | Amato et al. | |
| 7,198,639 B2 | 4/2007 | Lai et al. | |
| 7,297,460 B2 | 11/2007 | Vanmaele et al. | |
| 7,320,956 B2 | 1/2008 | Johnson et al. | |
| 7,572,872 B2 | 8/2009 | Flodin et al. | |
| 7,678,321 B2 | 3/2010 | Sirdesai et al. | |
| 7,682,622 B2 | 3/2010 | Horino | |
| 7,704,517 B2 | 4/2010 | Wang et al. | |
| 7,722,899 B2 | 5/2010 | Ono et al. | |
| 7,723,415 B2 | 5/2010 | Lichtenhan et al. | |
| 7,786,209 B2 | 8/2010 | Carlini et al. | |
| 7,803,358 B2 | 9/2010 | Gordan et al. | |
| 7,829,073 B2 | 11/2010 | Martin et al. | |
| 7,879,316 B2 | 2/2011 | Ferrari et al. | |
| 7,943,120 B2 | 5/2011 | Toyoda et al. | |
| 7,964,747 B2 | 6/2011 | Kim et al. | |
| 7,985,523 B2 | 7/2011 | Zhou et al. | |
| 8,025,829 B2 | 9/2011 | Zhang et al. | |
| 8,025,869 B2 | 9/2011 | Yu | |
| 8,080,257 B2 | 12/2011 | Kanji et al. | |
| 8,084,177 B2 | 12/2011 | Zhou et al. | |
| 8,124,058 B2 | 2/2012 | Schoon et al. | |
| 8,133,478 B2 | 3/2012 | Maitra et al. | |
| 8,263,677 B2 | 9/2012 | Conger et al. | |
| 8,367,742 B2 | 2/2013 | Vu et al. | |
| 8,399,537 B2 | 3/2013 | Conger et al. | |
| 8,492,454 B2 | 7/2013 | Vu et al. | |
| 8,901,199 B2 | 12/2014 | Vu et al. | |
| 2002/0114773 A1 | 8/2002 | Kanji et al. | |
| 2003/0012775 A1 | 1/2003 | Socci et al. | |
| 2004/0120915 A1 | 6/2004 | Yang et al. | |
| 2004/0180011 A1 | 9/2004 | Schlosser | |
| 2004/0191201 A1 | 9/2004 | Maio et al. | |
| 2004/0202622 A1* | 10/2004 | Quadir | A61K 8/585 |
| | | | 424/59 |
| 2004/0202623 A1* | 10/2004 | Quadir | A61K 8/585 |
| | | | 424/59 |
| 2005/0065297 A1 | 3/2005 | Patel | |
| 2005/0096427 A1* | 5/2005 | Odajima | C08F 290/14 |
| | | | 524/755 |
| 2005/0142089 A1 | 6/2005 | Lu et al. | |
| 2005/0192409 A1* | 9/2005 | Rhodes | C08F 230/08 |
| | | | 525/326.7 |
| 2005/0201961 A1 | 9/2005 | Lu et al. | |
| 2005/0220745 A1 | 10/2005 | Lu | |
| 2005/0244351 A1 | 11/2005 | Reinhart et al. | |
| 2006/0008441 A1 | 1/2006 | Kanji et al. | |
| 2006/0110346 A1 | 5/2006 | Lu | |
| 2006/0263318 A1 | 11/2006 | Lichtenhan et al. | |
| 2007/0132113 A1 | 6/2007 | Hinterman | |
| 2007/0141008 A1 | 6/2007 | Jones | |
| 2007/0166271 A1 | 7/2007 | Gordon et al. | |
| 2007/0286827 A1 | 12/2007 | Sheariss et al. | |
| 2008/0081022 A1* | 4/2008 | Yu | A61K 8/585 |
| | | | 424/43 |
| 2008/0102050 A1 | 5/2008 | Li et al. | |
| 2008/0175804 A1 | 7/2008 | Farcet | |
| 2008/0181859 A1 | 7/2008 | Farcet | |
| 2008/0305062 A1 | 12/2008 | Bui et al. | |
| 2009/0087473 A1 | 4/2009 | Inage | |
| 2009/0233031 A1 | 9/2009 | Weber et al. | |
| 2010/0012263 A1 | 1/2010 | Oshima et al. | |
| 2010/0055061 A1 | 3/2010 | Mandelli et al. | |
| 2010/0074854 A1 | 3/2010 | Guerchet et al. | |
| 2010/0098761 A1 | 4/2010 | Song et al. | |
| 2010/0166685 A1 | 7/2010 | Farcet | |
| 2011/0020413 A1 | 1/2011 | Gormley et al. | |
| 2011/0042004 A1 | 2/2011 | Schubert et al. | |
| 2011/0081306 A1 | 4/2011 | Vu et al. | |
| 2011/0082228 A1 | 4/2011 | Vu | |
| 2011/0110994 A1 | 5/2011 | Inokuchi et al. | |
| 2011/0236341 A1 | 9/2011 | Dop | |
| 2011/0262375 A1 | 10/2011 | Hinterman et al. | |
| 2011/0274633 A1 | 11/2011 | Vu et al. | |
| 2012/0003167 A1 | 1/2012 | Cavazzuti et al. | |
| 2012/0014899 A1 | 1/2012 | Dop | |
| 2012/0064019 A1 | 3/2012 | Cavazzuti et al. | |
| 2012/0071582 A1* | 3/2012 | Iezzi | C09D 163/00 |
| | | | 523/150 |
| 2012/0100089 A1 | 4/2012 | Barba et al. | |
| 2012/0128746 A1 | 5/2012 | Maitra et al. | |
| 2012/0142793 A1* | 6/2012 | Frey | C07F 7/21 |
| | | | 521/50.5 |
| 2012/0171137 A1 | 7/2012 | Bradsaw et al. | |
| 2012/0172495 A1* | 7/2012 | Czubarow | C08G 59/306 |
| | | | 523/456 |
| 2014/0053859 A1 | 2/2014 | Valia et al. | |
| 2014/0053895 A1 | 2/2014 | Reichertz et al. | |
| 2014/0056833 A1 | 2/2014 | Vu et al. | |

FOREIGN PATENT DOCUMENTS

| | | |
|---|---|---|
| JP | H 0240314 A | 2/1990 |
| WO | WO-9848769 A1 | 11/1998 |
| WO | WO-2011/011304 A2 | 1/2011 |
| WO | WO-2011/031578 A1 | 3/2011 |
| WO | WO-2011/043879 A1 | 4/2011 |
| WO | WO-2011/043880 A1 | 4/2011 |
| WO | WO-2012018403 A1 | 2/2012 |
| WO | WO-2012078751 A2 | 6/2012 |
| WO | WO-2012089692 A2 | 7/2012 |

OTHER PUBLICATIONS

Nielson "A Safe and Sustainable Plasticizer for Medical Applications," Medical Plastics, Collected Papers of the International Conference and Seminar, 20th, 2006 as evidenced by SciFinder abstract, printed 2014.

Ayandele et al., "Polyhedral Oligomeric Silsesquioxane (POSS)-Containing Polymer Nanocomposites (review)", Nanomaterials, 2012, vol. 2, pp. 445-475.

* cited by examiner

NAIL COATINGS HAVING ENHANCED ADHESION

CLAIM OF PRIORITY

This application is a continuation-in-part of U.S. application Ser. No. 14/786,491, filed Oct. 22, 2015, which is a U.S. National Stage of International Application No. PCT/US2014/035028, filed Apr. 22, 2014, which claims the benefit of U.S. Provisional Application No. 61/814,691, filed Apr. 22, 2013, each of which is hereby incorporated by reference in its entirety. This application is also a continuation-in-part of U.S. application Ser. No. 13/827,483, filed Mar. 14, 2013, which claims the benefit of U.S. Provisional Application No. 61/692,096, filed Aug. 22, 2012, each of which is hereby incorporated by reference in its entirety.

BACKGROUND OF THE DISCLOSURE

The nail plate (i.e., the natural nail) is primarily composed of keratin, a water-insoluble, fibrous protein that is a major structural component of skin, hair, wool, silk, feathers, scales, nails and hooves. While keratins can obviously differ greatly in their amino acid makeup, hard keratins may all be generally characterized as cross-linked polypeptides. Alpha-keratins such as nails and hooves may be further characterized by their relatively higher percentages of the amino acid cysteine. Typically, the alpha-helix coils of the polypeptides are cross-linked with disulphide bonds between adjacent cysteines. The resulting plate-like cells are cemented to each other with a sticky substance and held together by rivet-like structures called desmosomes. Many cell layers adhere to each other to form the nail plate, a structure that resembles a brick and mortar wall.

Conventional coatings for natural nails may be generally classified into three categories: nail polishes (also known as lacquers, varnish or enamels); artificial nails (also known as gels or acrylics); and hybrids. Nail enamels typically comprise various solid components which are dissolved and/or suspended in non-reactive solvents. Upon application and drying, the solids deposit on the nail surface as a clear, translucent or colored film. Usually, nail polishes are easily scratched and are easily removable with solvent, usually within one minute and if not removed as described, will chip or peel from the natural nail in one to five days.

Nail enamels coat the surface of the nail plate to provide a decorative finish with a characteristic glossy finish. Nail enamels conventionally comprise a film forming component, which is frequently nitrocellulose, cellulose acetate butyrate, or a combination of one or both of those cellulosics with a polyester or other polymeric compound. Most nail polishes are made of nitrocellulose dissolved in a solvent (e.g. butyl acetate or ethyl acetate) and either left clear or colored with various pigments. Typical components may include: film forming agents, resins and plasticizers, solvents, and coloring agents.

Artificial nails polymerize on the surface of a natural nail to form a hard, tough surface. Artificial nails conventionally include one or more (meth)acrylate monomers and a photoinitiator or hardener which may be mixed immediately before use. Optionally, the artificial nail composition may include a solvent or may utilize a liquid (meth)acrylate as a solvent. Artificial nails of this sort typically bond tightly and possibly irreversibly to the nail plate and must be removed by physical means such as filing.

Hybrid systems include both film-forming components and polymerizable components. In exemplary hybrid systems, the polymerizable components, for example (meth) acrylates, form a 3-dimensional (3-D) thermoset lattice and the film forming component, for example nitrocellulose or cellulose acetate butyrate is dispersed within the 3-D network. The 3-D thermoset lattice provides enhanced durability, toughness, and scratch-resistance over conventional nail enamels while the interdispered film-forming component provides a soluble network to allow for improved removability characteristics over artificial nails.

Application of nail coatings to the surface of the nail plate typically requires the surface of the nail plate to be treated. The surface treatment typically involves the use of a primer and/or roughening of the nail plate such as with the use of a file. This treatment process may cause damage to the nail plate, which is particularly problematic for individuals having thin nails.

Primers are adhesion promoters that improve adhesion by increasing interfacial compatibility between surfaces, e.g., the nail plate and an applied coating. For example, a coating of nail polish may resist chipping and peeling if a good primer is used. Primers are more compatible with the nail plate than the nail polish. Primers act as the "go-between" or "anchor", to improve adhesion.

Primers are also frequently used with artificial nail enhancements since acrylic nail products normally have poor adhesion to nail plates. In general, nail plate primers can be thought of as double-sided sticky tape, joining the nail plate to the nail enhancement. The nail plate surface is made up of chemical groups possessing specific structures. Primer molecules typically match the chemical and structural characteristics of the nail plate. In specific embodiments, one end of the primer is reactive with methacrylate monomers. With these types of primers, physical abrasion of the nail plate is required to achieve proper levels of adhesion to the keratin substrate. As such, these primers can be destructive, and if used improperly they can cause damage to the nail plate and surrounding tissue. These primers can also cause discoloration of the nail enhancement. Indeed, they are the leading cause of discoloration.

There remains a need in the art for nail coatings with enhanced adhesion that do not peel or chip from the nail surface but do not damage or discolor the nail surface.

BRIEF SUMMARY OF THE DISCLOSURE

Throughout this description, including the foregoing description of related art, any and all publicly available documents described herein, including any and all U.S. patents, are specifically incorporated by reference herein in their entirety. The foregoing description of related art is not intended in any way as an admission that any of the documents described therein, including pending United States patent applications, are prior art to embodiments of the present disclosure.

Moreover, the description herein of any disadvantages associated with the described products, methods, and/or apparatus, is not intended to limit the disclosed embodiments. Indeed, embodiments of the present disclosure may include certain features of the described products, methods, and/or apparatus without suffering from their described disadvantages.

Embodiments of the present disclosure relate to nail coatings. In specific non-limiting embodiments, the disclosure relates to nail coating compositions containing at least one polyhedral oligomeric silsesquioxane (POSS) and having improved adhesion.

The nail coatings described herein eliminate the need to surface prep the nail plate with primers, filings or other means that may cause damage or otherwise thin the nail plate. In specific non-limiting embodiments, described herein are nail coating compositions and methods that provide enhanced adhesion of the coating to the nail, and/or between layers of a multilayer coating.

Provided in some embodiments is a nail coating that includes at least one film forming agent; at least one silicone resin; and solvent. In specific embodiments, the at least one film forming agent is a cellulosic resin.

Provided in some embodiments is a nail coating including at least one film forming agent; at least one plasticizer; at least one silicone resin; and solvent.

Provided in some embodiments is a nail coating containing at least one film forming agent; at least one silicone resin; at least one coloring agent; and solvent. In specific non-limiting embodiments, the at least one film forming agent is a cellulosic resin.

Provided in some embodiments is a nail coating that includes at least one film forming agent; at least one plasticizer; at least one silicone resin; at least one coloring agent; and at least one solvent. In specific non-limiting embodiments, the at least one film forming agent is a cellulosic resin.

In various embodiments, the silicon resin and film forming agent, such as a cellulosic resin, are combined in a ratio of silicon resin to the film forming agent from about 1:10 to about 1:1. In some specific non-limiting embodiments, the silicon resin is a polyhedral oligomeric silsesquioxane. In some specific non-limiting embodiments, the cellulosic resin is nitrocellulose, a cellulose ester, a cellulose acetate alkylate, or a cellulose acetate alkylate. In specific embodiments, the cellulose acetate alkylate is selected from the group consisting of cellulose acetate butyrate, cellulose acetate propionate, and mixtures thereof.

In various specific embodiments, the plasticizer is an alkyl citrate, including but not limited to acetyl tributyl citrate. In other specific embodiments, the plasticizer is an acetylated monoglyceride.

In some embodiments, the nail coating composition includes at least one polyhedral oligomeric silsesquioxane.

Provided in some embodiments is a nail topcoat comprising: at least one film forming agent; at least one silicone resin; a component selected from at least one ethylenically unsaturated monomer, at least one urethane (meth)acrylate resin or a combination thereof; at least one photoinitiator; and a solvent.

Provided in some embodiments is a top coat containing at least one film forming agent; at least one plasticizer; at least one silicone resin; at least one photoinitiator; solvent; and a component selected from at least one ethylenically unsaturated monomer, at least one urethane (meth)acrylate resin or a combination thereof.

In specific embodiments, the plasticizer is an alkyl citrate, including but not limited to acetyl tributyl citrate. In other specific embodiments, the plasticizer is an acetylated monoglyceride.

In various embodiments, the nail coating composition can further include a film-forming polymer. In specific embodiments, the film-forming polymer is water-dispersible, and the composition includes water. In other specific embodiments, the nail coating composition includes a non-aqueous, non-reactive solvent. In various embodiments, the nail coating composition further includes at least one reactive (meth)acrylate; and at least one non-reactive, solvent dissolvable polymer.

According to some embodiments, there is provided a nail topcoat that includes at least one film forming agent; at least one plasticizer; at least one silicone resin a component selected from at least one ethylenically unsaturated monomer, at least one urethane (meth)acrylate resin or a combination thereof; at least one high molecular weight (meth)acrylate polymer or copolymer; at least one photoinitiator; and solvent. In this and other embodiments, the (meth)acrylate polymer or copolymer can be a copolymer of an alkyl (meth)acrylate and a (meth)acrylic acid.

In some embodiments, the (meth)acrylate polymer or copolymer is a copolymer of an alkyl methacrylate and methacrylic acid. In some embodiments, the alkyl methacrylate is methyl methacrylate or butyl methacrylate.

In specific embodiments, the nail coating composition can further include at least one reactive (meth)acrylate; at least one reactive urethane (meth)acrylate; at least one polymethylmethacrylate (PMMA)-polymethylacrylic acid (PMAA) copolymer; at least one non-reactive, solvent dissolvable polymer; and at least one non-reactive solvent. In these embodiments as well as others, the nail coating composition can further include at least one reactive polypropylene glycol (meth)acrylated monomer or polyethylene glycol (meth)acrylated monomer.

Provided in some embodiments is a nail topcoat that includes at least one film forming agent; at least one silicone resin; at least one ethylenically unsaturated monomer; at least one high molecular weight (meth)acrylate polymer or copolymer; at least one photoinitiator; and solvent. In some specific embodiments, the nail coating composition further includes at least one reactive (meth)acrylate; and a polymerization accelerator, a polymerization initiator, or a combination thereof; wherein the composition is free of added solvent. In some specific embodiments, the nail coating composition further includes a multicarbonyl-vinyl containing monomer.

Provided in some embodiments is a nail topcoat containing at least one film forming agent; at least one silicone resin; at least one ethylenically unsaturated monomer; at least one urethane (meth)acrylate resin; at least one photoinitiator; and at least one solvent. In specific embodiments, the nail coating composition further includes at least one reactive urethane (meth)acrylate. In some specific embodiments, the nail coating composition further includes at least one polymethylmethacrylate (PMMA)-polymethylacrylic acid (PMAA) copolymer. In various embodiments, the nail coating composition cures to an acrylic thermoset having voids defined therein upon exposure to actinic radiation. In other embodiments, the nail coating composition cures to an acrylic thermoset having voids defined therein upon exposure to visible light. In specific embodiments, the nail coating composition further includes a non-reactive solvent.

Provided in some embodiments is a nail topcoat that includes at least one film forming agent; at least one silicone resin; at least one urethane (meth)acrylate resin; at least one photoinitiator; and solvent. In various specific embodiments, the at least one reactive (meth)acrylate includes hydroxypropyl methacrylate (HPMA), hydroxyethyl methacrylate (HEMA), ethyl methacrylate (EMA), tetrahydrofurfuryl methacrylate, pyromellitic dianhydride di(meth)acrylate, pyromellitic dianhydride glyceryl dimethacrylate, pyromellitic dimethacrylate, methacroyloxyethyl maleate, 2-hydroxyethyl methacrylate/succinate, 1,3-glycerol dimethacrylate/succinate adduct, phthalic acid monoethyl methacrylate, or a mixture thereof.

Provided in some embodiments is a nail topcoat including at least one film forming agent; at least one silicone resin; at least one ethylenically unsaturated monomer; at least one photoinitiator; and at least one solvent. In specific embodiments, the nail coating composition further includes at least one reactive polypropylene glycol (meth)acrylated monomer or polyethylene glycol (meth)acrylated monomer.

Provided in some embodiments is a nail topcoat containing at least one film forming agent; at least one silicone resin; at least one urethane (meth)acrylate resin; at least one high molecular weight (meth)acrylate polymer or copolymer; at least one photoinitiator; and at least one solvent. In some embodiments, the nail coating composition further includes an adhesion promoter. In specific embodiments, the adhesion promoter is selected from the group consisting of: hydroxypropyl methacrylate (HPMA); hydroxyethyl methacrylate (HEMA); ethyl methacrylate (EMA); tetrahydrofurfuryl methacrylate (THFMA); pyromellitic dianhydride di(meth)acrylate; pyromellitic dianhydride glyceryl dimethacrylate; pyromellitic dimethacrylate; methacroyloxyethyl maleate; 2-hydroxyethyl methacrylate/succinate; 1,3-glycerol dimethacrylate/succinate adduct; phthalic acid monoethyl methacrylate; methacroyloxyethyl maleate; 2-hydroxyethyl methacrylate/succinate; 1,3-glycerol dimethacrylate/succinate adduct; butyl methacrylate; isobutyl methacrylate; PEG-4 dimethacrylate; PPG monomethacrylate; trimethylolpropane trimethacrylate; isopropylidenediphenyl bisglycidyl methacrylate; lauryl methacrylate; cyclohexyl methacrylate; hexyl methacrylate; urethane methacrylate; triethylene glycol dimethacrylate; ethylene glycol dimethacrylate; tetraethylene glycol dimethacrylate; trimethylolpropane trimethacrylate; neopentylglycol dimethacrylate; acetoacetoxy methacrylate; acetoacetoxyethyl methacrylate (AAEMA); polyetheramine; glycidyl methacrylates; maleic anhydride; terpolymers containing vinyl acetate; organosilanes; organotitanates; chlorinated polyolefins; sucrose acetate isobutyrate; caprylic/capric triglyceride; glyceryl hydrogenated rosinate; pentaerythryl hydrogenated rosinate; styrene/methyl styrene/indene copolymer; blocked isocyanate PVC; polyamidoamine PVC; and mixtures thereof.

Provided in some embodiments is a nail topcoat that includes at least one film forming agent; at least one silicone resin; at least one ethylenically unsaturated monomer; at least one urethane (meth)acrylate resin; at least one high molecular weight (meth)acrylate polymer or copolymer; at least one photoinitiator; and at least one solvent.

In some specific embodiments, the at least one polyhedral oligomeric silsesquioxane can include Glycidyl POSS® Cage Mixture (sold by Hybrid Plastics as EP0409); Trimethoxy-[2-(7-oxabicyclo[4.1.0]hept-3-yl)ethyl]silane, hydrolyzed (sold by Hybrid Plastics as EP0408); Hydrolyzed [3-(Trimethoxysilyl)propyl]aniline (sold by Hybrid Plastics as AM0281); [(dimethyl(norbornenylethyl)silyloxy)dihydroxy]-POSS® (sold by Hybrid Plastics as NB1038); (vinyl silsesquioxane resin)-liquid (sold by Hybrid Plastics as PM1285MV); Acrylo POSS® Cage Mixture (sold by Hybrid Plastics as MA0736); methacrylated ethoxylated POSS®; ethoxylated glycidyl POSS®; or a mixture thereof.

In some specific embodiments, the plasticizer is an alkyl citrate, including but not limited to acetyl tributyl citrate, or an acetylated monoglyceride. In some embodiments, the (meth)acrylate polymer or copolymer is a copolymer of an alkyl (meth)acrylate and a (meth)acrylic acid, for example, a copolymer of an alkyl methacrylate, such as butyl methacrylate or methyl methacrylate, and methacrylic acid. In specific embodiments, the nail coating composition further includes a di-, tri-, or poly-functional ethylenically unsaturated reactant.

Provided in some embodiments is a nail coating system comprising the nail coating of any of the present embodiments and a nail topcoat. Provided in some embodiments is a nail coating system that includes a nail coating and the nail topcoat of any of the present embodiments.

In various specific embodiments, the solvent-dissolvable polymer or film-forming polymer is selected from the group consisting of: a cellulose ester; a cellulose acetate alkylate; a cellulose acetate butyrate; a cellulose acetate propionate; ethyl tosylamide; adipic acid/fumaric acid/phthalic acid/tricyclodecane dimethanol copolymer; adipic acid/neopentyl glycol/trimellitic anhydride copolymer; phthalic anhydride/trimellitic anhydride/glycols copolymer; polyethyl cellulose; polyhydroxypropyl cellulose; polyethyl acrylate oxide; poly lactic acid; nitrocellulose; cellulose ester; and mixtures thereof.

Provided in some embodiments is a multilayer nail coating system that includes the nail coating described herein and a nail topcoat. Provided in some embodiments is a multilayer nail coating system that includes at least a nail coating and the nail topcoat of the present embodiments.

Provided in some embodiments is a method of applying a nail coating to an uncoated nail, the method including the steps of: applying the nail coating of the present embodiments to the uncoated nail. In specific embodiments, the method further includes applying a nail topcoat to the coated nail surface.

Provided in some embodiments is a method of applying a nail coating to a natural nail that includes the steps of: applying a nail coating of the present embodiments to the natural nail. In some specific embodiments, the method also includes applying a nail topcoat to the coated nail surface. In other specific embodiments, the natural nail is not roughened or otherwise treated in order to promote the adhesion of a nail coating prior to applying the nail coating. In yet other embodiments, the natural nail is not surface treated with a primer prior to applying the coating. In some specific embodiments, the natural nail is not surface treated with a file prior to applying the coating.

Provided in some embodiments is a method of improving adhesion of a nail coating comprising adding at least one polyhedral oligomeric silsesquioxane to a nail coating composition described herein.

In one embodiment, the nail coating composition further includes at least one reactive (meth)acrylate; and at least one non-reactive, solvent dissolvable polymer. In one embodiment, the nail coating composition further includes: at least one reactive (meth)acrylate; at least one reactive urethane (meth)acrylate; at least one polymethylmethacrylate (PMMA)-polymethylacrylic acid (PMAA) copolymer; at least one non-reactive, solvent dissolvable polymer; and at least one non-reactive solvent. In specific embodiments, the nail coating composition further includes at least one reactive polypropylene glycol (meth)acrylated monomer or polyethylene glycol (meth)acrylated monomer.

In some embodiments, the nail coating composition can further include a film-forming polymer. In specific embodiments, the film-forming polymer is water-dispersible, and the composition further includes water.

In other embodiments, the nail coating composition further includes a non-aqueous, non-reactive solvent. In some embodiments, the nail coating composition further includes: at least one reactive (meth)acrylate; a polymerization accelerator, a polymerization initiator, or a combination thereof; and wherein the composition is free of added solvent. In specific embodiments, the nail coating composition further includes a multicarbonyl-vinyl containing monomer.

Still other aspects and advantages of the present invention will become readily apparent by those skilled in the art from the following detailed description, wherein it is shown and described preferred embodiments of the invention, simply by way of illustration of the best mode contemplated of carrying out the invention. As will be realized, the invention is capable of other and different embodiments, and its several details are capable of modifications in various obvious respects, without departing from the invention. Accordingly, the description is to be regarded as illustrative in nature and not as restrictive.

DETAILED DESCRIPTION OF THE INVENTION

Exemplary Definitions

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and not intended to be limiting. Other features and advantages of the invention will be apparent from the following detailed description and claims.

For the purposes of promoting an understanding of the embodiments described herein, reference will be made to preferred embodiments and specific language will be used to describe the same. The terminology used herein is for the purpose of describing particular embodiments only, and is not intended to limit the scope of the present invention. As used throughout this disclosure, the singular forms "a," "an," and "the" include plural references unless the context clearly dictates otherwise. Thus, for example, a reference to "a composition" includes a plurality of such compositions, as well as a single composition.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and not intended to be limiting. Other features and advantages of the invention will be apparent from the following detailed description and claims.

The terms "nail" and "nail surface" mean the natural, keratinaceous nail surface, or a natural nail to which an artificial nail or nail tip is adhered. In other words, the polymerizable compositions of the invention may be applied directly to the keratinaceous surface of the natural nail, or to a nail surface having affixed thereto an artificial nail or nail tip enhancement.

Exemplary Nail Coatings

The present application describes nail coatings. As compared to conventional nail enamels, the nail coating of the present embodiments has a major advantage in that it enables the nail coating, which may also contain color, to adhere to the natural nail for long wear periods without adhesion loss or other signs of breakdown of the coating. The improved wear is achieved without the need of surface prepping the nail, such as with the use of primers or by slightly roughing the surface with a file or other means. For example, the nail coating of the present embodiments may be applied directly to the nail.

In some embodiments, it may be recommended to simply clean the surface of the nail to remove excess dirt and/or excess of natural oils. Cleaning of the nail surface may be achieved with the light use of solvent such as isopropyl alcohol or acetone.

According to some embodiments, nail coatings of the present invention include: at least one film forming agent; at least one silicone resin; at least one coloring agent; and solvent. According to some embodiments, nail coatings of the present invention contain at least one film forming agent, at least one plasticizer, at least one silicone resin; at least one coloring agent; and a solvent.

In one aspect, the invention is a single layer nail coating that may contain color and exhibits enhanced adhesion to the nail surface to resist chipping and peeling. According to an aspect, the disclosure provides a primer for pre-treating a nail surface before application of a nail coating that may, for example, improve adhesion of the nail coating to the nail surface, compared to an untreated nail. According to an aspect, the disclosure provides a nail coating that is a basecoat interposed between the nail surface and an additional layer that may enhance appearance, e.g., by providing a gloss finish or containing color or may provide a protective surface. According to an aspect, the disclosure provides a color layer that is applied to an exposed surface of a basecoat. According to an aspect, the disclosure provides a protective topcoat that is applied to an exposed surface of a color layer or basecoat.

Provided in some embodiments is a nail coating comprising: between about 1.5% by weight to about 35% by weight of at least one film forming agent; between about 1% by weight and about 10% by weight of at least one silicone resin; and between about 50% by weight and about 70% by weight of solvent.

Provided in some embodiments is a nail coating comprising between about 1.5% by weight and about 35% by weight of at least one film forming agent; between about 0% by weight and about 10% by weight of at least one plasticizer; between about 1% by weight and about 10% by weight of at least one silicone resin; and between about 50% by weight and about 70% by weight of solvent. In embodiments, the nail coating can also include between about 0% by weight and about 10% by weight of at least one coloring agent.

Provided in some embodiments is a nail coating comprising between about 1.5% by weight and about 50% by weight of at least one film forming agent. In some embodiments, the nail coating includes between about 10% by weight and about 50% by weight of at least one film forming agent. In some embodiments, the nail coating contains between about 1.5% by weight and about 35% by weight of at least one film forming agent. In some embodiments, the nail coating contains between about 8% by weight and about 20% by weight of at least one film forming agent. In some embodiments, the nail coating contains between about 10% by weight and about 35% by weight of at least one film forming agent. In some embodiments, the nail coating contains between about 10% by weight and about 25% by weight of at least one film forming agent. In some embodiments, the nail coating includes between about 10% by weight and about 20% by weight of at least one film forming agent. In some embodiments, the nail coating includes between about 20% by weight and about 35% by weight of at least one film forming agent.

In specific embodiments, the nail coatings described contain between about 0% by weight and about 20% by weight of at least one plasticizer.

In some specific embodiments, the nail coatings contain between about 0.5% by weight and about 20% by weight of at least one plasticizer. In some embodiments, the nail coating contains between about 1% by weight and about 10% by weight of at least one plasticizer. In some embodiments, the nail coating contains between about 2% by weight and about 10% by weight of at least one plasticizer. In some embodiments, the nail coating contains between about 3% by weight and about 10% by weight of at least one plasticizer. In some embodiments, the nail coating contains between about 5% weight to about 10% by weight of at least one plasticizer. In some embodiments, the nail coating contains between about 3% by weight and about 7% by weight of at least one plasticizer.

In some specific embodiments, the plasticizer is present in the amount of at least 0.05% by weight, at least 1% by weight; or at least 3% by weight. In some embodiments, the nail coating contains between about 1% by weight and about 3% by weight of a plasticizer; or between about 1% by weight about 7% by weight of a plasticizer.

In specific embodiments, the at least one plasticizer is an acetylated monoglyceride. In some embodiments, the acetylated monoglyceride is present in the amount of at least 1% by weight; or at least 3% by weight. In some specific embodiments, the nail coating contains between about 1% by weight and about 3% by weight of an acetylated monoglyceride; or between about 1% by weight and about 7% by weight of an acetylated monoglyceride.

In specific embodiments, the at least one plasticizer is an alkyl citrate. In some embodiments, the alkyl citrate is present in the amount of at least 1% by weight; or at least 3% by weight. In some specific embodiments, the nail coating contains between about 1% by weight and about 3% by weight of an alkyl citrate; or between about 1% by weight and about 7% by weight of an alkyl citrate. In some embodiments, the alkyl citrate is acetyl tributyl citrate.

Some embodiments of the nail coatings of the invention described herein achieve enhanced adhesion by the incorporation of a polyhedral oligomeric silsesquioxane into the composition that is applied to the nail. Nail coatings of the invention provide enhanced adhesion to the nail surface, including natural nails and artificial nails, and, when used in multilayer systems, interlaminar adhesion between the various layers. As such, the nail coatings have longer wear characteristics, i.e. remain intact on the nail surface for longer periods of time. In most cases, the inventive nail coatings remain readily removable by use of suitable solvents.

In some specific embodiments, the nail coatings contain between about 1% by weight and about 10% by weight of at least one silicone resin; or between about 3% by weight and about 10% by weight of at least one silicone resin; or between about 5% by weight and about 10% by weight of at least one silicone resin; or between about 3% by weight and about 7% by weight of at least one silicone resin. In specific embodiments, the silicone resin is a polyhedral oligomeric silsesquioxane.

A number of nail coating systems can demonstrate enhanced adhesion by the incorporation of a polyhedral oligomeric silsesquioxane. Among these are polymerizable nail coating systems; film-forming nail coating systems; water based nail coating systems; and liquid-and-powder nail coating systems. Described herein is each of these nail coating systems, and the components that may be used in nail coating formulations according to each system.

In some embodiments, nail coatings of the present invention contains between about 1% by weight and about 10% by weight of at least one coloring agent; or between about 3% by weight and about 10% by weight of at least one coloring agent; or includes between about 5% by weight and about 10% by weight of at least one coloring agent; or between about 3% by weight and about 7% by weight of at least one coloring agent. In some specific embodiments, the at least one coloring agent may be present in the nail coating composition in an amount up to about 5% by weight relative to the total weight of the composition; or between about 2% by weight and about 3% by weight.

In some specific embodiments, nail coatings of the present invention contain between about 50% by weight and about 70% by weight solvent; or between about 60% by weight and about 70% by weight solvent; or between about 55% by weight and about 65% by weight solvent.

In some embodiments, the nail coatings described herein are applied to the nail in conjunction with the use of a nail topcoat. For example, the nail coating, optionally containing a color agent, is applied to an uncoated or natural nail surface, allowed to dry, and then a nail topcoat is applied on top of the nail coating. The nail topcoat may be any topcoat known in the art. In some embodiments, the nail topcoat is a nail topcoat according to the present embodiments, described in more detail herein below.

In various embodiments, the invention comprises the addition of POSS to a wide range of nail coatings and nail coating systems including nail enamels, polymerizable nail coatings (artificial nails, gels acrylics), hybrid systems, and nail primers. In these embodiments, the POSS can be added to an existing stock or base system or formulated as a part of the stock or base system. As used herein, "base system" refers to an existing nail coating that does not include POSS and is distinguished from a "basecoat" which refers to a nail coating applied directly to a nail prior to an additional coating.

The coating systems to which POSS can be added to enhance adhesive properties is described herein. Also provided herein are descriptions of the various components that can be present in nail coatins described.

Non-limiting nail coatings to which POSS can be added include those disclosed in U.S. Pat. Nos. 8,124,058; 6,818, 207; 8,399,537; 8,263,677; 8,367,742; 5,985,951; 5,785, 958; 5,576,509; 5,965,147; 5,639,447; 6,051,242; 5,130, 125; 5,512,273; 5,662,891; 5,720,804; 4,871,534; 5,785, 958; 8,492,454; 8,541,482; 8,901,199; and 7,678,321; in US Patent Application Publication Nos. 2010/0012263; 2005/ 0065297; 2007/0286827; 2014/0056833; 2014/0053895; and 2014/0053859; and in PCT Publication Nos. WO 2011/ 011304; WO 2011/031578; WO 2011/043880 and WO 2011/043879. The disclosures of each of these patents, publications, and patent applications are hereby incorporated by reference in their entirety.

Exemplary Nail Topcoats

Provided in some embodiments is a nail topcoat having improved abrasion resistance. According to some specific embodiments, nail topcoats according to the invention include at least one film forming agent, at least one silicone resin; at least one photoinitiator; a component selected from at least one ethylenically unsaturated monomer and, at least one urethane (meth)acrylate resin or a combination thereof; and at least one solvent.

Provided in some embodiments is a nail topcoat including at least one film forming agent, at least one plasticizer, at least one silicone resin; a component selected from at least one ethylenically unsaturated monomer and, at least one urethane (meth)acrylate resin or a combination thereof; at least one photoinitiator; and at least one solvent.

Provided in some embodiments is a nail topcoat that includes at least one film forming agent, at least one silicone resin; at least one ethylenically unsaturated monomer; at least one photoinitiator; and solvent. In some specific embodiments, the nail topcoat contains at least one film forming agent, at least one silicone resin; at least one ethylenically unsaturated monomer; at least one high molecular weight (meth)acrylate polymer or copolymer; at least one photoinitiator; and solvent. In some embodiments, the nail topcoat contains at least one film forming agent, at least one silicone resin; at least one ethylenically unsaturated monomer; at least one urethane (meth)acrylate; at least one photoinitiator; and at least onesolvent.

Provided in some embodiments is a nail topcoat containing at least one film forming agent; at least one silicone resin; at least one urethane (meth)acrylate resin; at least one photoinitiator; and solvent.

In some specific embodiments, the nail topcoat contains at least one film forming agent; at least one silicone resin; at least one urethane (meth)acrylate resin; at least one high molecular weight (meth)acrylate polymer or copolymer; at least one photoinitiator; and at least one solvent. In some specific embodiments, the nail topcoat contains at least one film forming agent; at least one silicone resin; at least one ethylenically unsaturated monomer; at least one urethane (meth)acrylate resin; at least one high molecular weight (meth)acrylate polymer or copolymer; at least one photoinitiator; and at least one solvent.

According to some specific embodiments, the nail topcoat contains between about 5% by weight and about 40% by weight of at least one film forming agent; between about 0% by weight and about 10% by weight of at least one plasticizer; between about 0.1% by weight and about 10% by weight of at least one silicone resin; between about 50% by weight and about 70% by weight of solvent; between about 0.5% by weight and about 10% by weight of at least one ethylenically unsaturated monomer; between about 0.5% by weight and about 10% by weight of at least one high molecular weight (meth)acrylate; and between about 0.1% by weight and about 5% by weight of at least one photoinitiator.

According to some specific embodiments, the nail topcoat contains between about 5% by weight and about 40% by weight of at least one film forming agent; between about 0% by weight and about 5% by weight of at least one plasticizer; between about 0.1% by weight and about 5% by weight of at least one silicone resin; between about 50% by weight and about 70% by weight % of solvent; between about 0.5% by weight and about 7% by weight of at least one ethylenically unsaturated monomer; between about 0.5% by weight and about 5% by weight of high molecular weight (meth)acrylate; and between about 0.005% by weight and about 5% by weight of photoinitiator.

According to some specific embodiments, the nail topcoat contains between about 1.5% by weight and about 50% by weight of at least one film forming agent. In some embodiments, the nail topcoat contains between about 10% by weight and about 50% by weight of at least one film forming agent.

According to some specific embodiments, the nail topcoat contains between about 1.5% by weight and about 35% by weight of at least one film forming agent. In some embodiments, the nail topcoat contains between about 8% by weight and about 20% by weight of at least one film forming agent According to some specific embodiments, the nail topcoat contains between about 10% by weight and about 35% by weight of at least one film forming agent. In some embodiments, the nail topcoat contains between about 10% by weight and about 25% by weight of at least one film forming agent.

According to some specific embodiments, the nail topcoat contains between about 10% by weight and about 20% by weight of at least one film forming agent.

According to some specific embodiments, the nail topcoat contains between about 20% by weight and about 35% by weight of at least one film forming agent.

In some embodiments that include a plasticizer, the nail topcoat contains between about 0.1% by weight and about 5% by weight of at least one plasticizer; or about 0.5% by weight and about 20% by weight of at least one plasticizer; or between about 1% by weight and about 10% by weight of at least one plasticizer; or between about 2% by weight and about 10% by weight of at least one plasticizer; or between about 3% by weight and about 10% by weight of at least one plasticizer; or between about 5% by weight and about 10% by weight of at least one plasticizer; or between about 3% by weight and about 7% by weight of at least one plasticizer.

In some embodiments, the plasticizer is present in the amount of at least 1% by weight; or at least 3% by weight; or between about 1% by weight and about 3% by weight of a plasticizer; or between about 1% by weight and about 7% by weight of a plasticizer.

In some embodiments that include at least one silicone resin, the nail topcoat contains between about 1% by weight and about 10% by weight of at least one silicone resin; or between about 3% by weight and about 10% by weight of at least one silicone resin; or between about 5% by weight and about 10% by weight of at least one silicone resin; or between about 3% by weight and about 7% by weight of at least one silicone resin. In specific embodiments, the silicone resin is a polyhedral oligomeric silsesquioxane.

In some embodiments that include a photoinitiator, the nail topcoat contains between about 0.005% by weight and about 5% by weight photoinitiator; or between about 0.01% by weight and about 5% by weight photoinitiator; or between about 0.1% by weight and about 5% by weight photoinitiator.

In some embodiments that contain an ethylenically unsaturated monomer, the nail topcoat of the invention includes between about 0.5% by weight and about 10% by weight of at least one ethylenically unsaturated monomer; or between about 0.5% by weight and about 7% by weight of at least one ethylenically unsaturated monomer.

In some embodiments that contain a high molecular weight (meth)acrylate polymer or copolymer, the nail coating includes between about 0.5% by weight and about 10% by weight of the at least one (meth)acrylate polymer or copolymer; or between about 0.5% by weight and about 5% by weight of at least one (meth)acrylate polymer or copolymer.

In some embodiments that contain at least one (meth) acrylate polymer or copolymer, the nail coating contains between about 1% by weight and about 10% by weight of at least one (meth)acrylate polymer or copolymer; or between about 3% by weight and about 10% by weight of at least one (meth)acrylate polymer or copolymer; or between about 5% by weight and about 10% by weight of at least one (meth) acrylate polymer or copolymer; or between about 3% by weight and about 7% by weight of at least one (meth) acrylate polymer or copolymer.

In some embodiments containing a urethane (meth)acrylate resin, the nail coating of the invention includes between about 0.5% by weight and about 10% by weight of at least one urethane (meth)acrylate resin; or between about 0.5% by weight and about 5% by weight of at least one urethane (meth)acrylate resin; or between about 1% by weight and about 10% by weight of at least one urethane (meth)acrylate resin; or between about 3% by weight and about 10% by weight of at least one urethane (meth)acrylate resin; or between about 5% by weight and about 10% by weight of at least one urethane (meth)acrylate resin; or between about 3% by weight and about 7% by weight of at least one urethane (meth)acrylate resin.

In some embodiments containing one or more solvents, the nail topcoat contains between about 50% by weight and about 70% by weight solvent; or between about 60% by weight and about 70% by weight solvent; or between about 55% by weight and about 65% by weight solvent.

According to some embodiments, the nail topcoat contains between about 1.5% by weight and about 40% by weight of at least one film forming agent; between about 0.1% by weight and about 10% by weight of at least one plasticizer; between about 0.1% by weight and about 10% by weight of at least one silicone resin; between about 50% by weight and about 70% by weight of solvent; between about 0.5% by weight and about 10% by weight of at least one ethylenically unsaturated monomer; between about 0.5% by weight and about 10% by weight of at least one urethane (meth)acrylate resin; and between about 0.1% by weight and about 5% by weight of at least one photoinitiator.

According to some embodiments, the nail topcoats contains between about 5% by weight and about 40% by weight of at least one film forming agent; between about 0.1% by weight and about 5% by weight of at least one plasticizer; between about 0.1% by weight and about 5% by weight of at least one silicone resin; between about 50% by weight and about 70% by weight of solvent; between about 0.5% by weight and about 7% by weight of at least one ethylenically unsaturated monomer; between about 0.5% by weight and about 5% by weight of urethane (meth)acrylate resin; and between about 0.1% by weight and about 5% by weight of photoinitiator.

Exemplary Multilayer System

According to some embodiments, provided herein is a nail coating system that includes a nail coating according to the present embodiments and a nail topcoat. According to some embodiments, there is provided a multilayer nail coating system that includes at least a nail coating according to the present embodiments and a nail topcoat. The nail topcoat may be any topcoat known in the art. In some embodiments, the nail topcoat is a nail topcoat according to the present embodiments.

Nail coating systems of the present embodiments provide a nail coating to the nail having improved wear. "Wear," as used herein, refers to the length of time the consistency, coverage, texture, and/or color of a material remains unnoticeably different when compared to the time of application, as viewed by the naked eye of a normal observer. Wear may be evaluated by a test involving the application to a human nail and evaluating the consistency, texture and color of the composition after an extended period of time. For example, the consistency, texture and/or color of a nail coating may be evaluated immediately following application and these characteristics may then be re-evaluated and compared after an individual has worn the nail coating for a certain amount of time, for example one day, five days, seven days, ten days, or longer. These characteristics may be evaluated with respect to other compositions, such as commercially available compositions, a control or standard. The amount of time a coating is "wearable" is identifies as the amount of time the coating remains unnoticeably different, i.e. the amount if time the coating exists without showing signs of wear.

The nail coatings of the present embodiments show long wear or improved wear as compared to enamel coatings know in the prior art. "Long wear" or "improved wear" refers to the ability of a nail coating to stay on for an extended period of time without damage such as imprinting, chipping or loss of adhesion. "Long wear" may also be described as the ability to retain the appearance of having been freshly or recently applied for an extended period of time, for example one day, five days, seven days, ten days, or longer. Such nail coatings can also be described as having good or effective staying power, in that they can resist transfer from the surface to which they are applied for an extended period of time, preferably under various conditions. "Long wear" is used interchangeably herein with "extended wear," "increased wear," or "longer wear."

In some embodiments, nail coatings of the present embodiments are wearable for at least five days. In some embodiments, nail coatings of the present embodiments are wearable for at least seven days. In some embodiments, nail coatings of the present embodiments are wearable for at least ten days. In some embodiments, nail coatings of the present embodiments are wearable for at least seven to ten days. In some embodiments, nail coatings of the present embodiments are wearable for at least five to seven days.

According to an aspect, the inventive coating is applied as distinct layers, one or more of which may be at least partially cured. POSS can be present in any one or more layers of the coating. According to an aspect, the inventive coating can be applied as two distinct layers. According to an aspect, the inventive coating can be applied as three distinct layers. As such, it is contemplated that the coating can be applied as a two-layer, or three-layer system, or coild possibly include more than three layers. According to an aspect, a formulation for any of the layers may comprise colorant.

Aspects of the present disclosure provide a basecoat as a layer intermediate between the nail and coating surfaces. The inventive basecoat can be a polymerizable liquid, and provides a conformal coating over the nail surface. The basecoat may also contain a pigment or color. The inventive composition may be polymerizable with actinic radiation. The actinic radiation may be ultraviolet (UV) radiation. In some embodiments, no additional layers are applied over the basecoat.

Aspects of the present disclosure provide an intermediate layer that can be a decorative layer, for example a color layer. The intermediate layer may be applied to an exposed surface of a basecoat layer.

Aspects of the present disclosure provide a topcoat layer to be applied to an exposed surface of the basecoat or intermediate layer. The one or more layers of a nail coating can include one or more components selected from the following categories of components: reactive monomers, and/or oligomers, and/or polymers; a high-molecular weight (meth)acrylate polymer or copolymer; a polymer which conveys enhanced adhesiveness and which confers solvent sensitivity to the polymerized lattice; a urethane methacrylate resin; a (meth)acrylate monomer which provides improved adhesion, viscosity, wear and durability; an aromatic or aliphatic (meth)acrylate monomer which may be present to improve adhesion; a monomer and/or oligomer providing one or more free hydroxyl groups; an adhesion promoter; a non-reactive, solvent-dissolvable polymer; an optional resin; a plasticizer; a UV stabilizing agent; a polymerization initiator/photoinitiator; a polymerization regulator; a color agent; and a solvent.

Exemplary Film Forming Agents

In some embodiments, the at least one film forming agent in the coating (nail coating or nail topcoat) is a film forming polymer. Film forming polymers include, but are not limited to, polyesters; resins, such as polyurethane resins, alkyd resins, and polyvinyl resins such as polyvinyl acetate, polyvinyl chloride, polyvinylbutyrate; (meth)acrylic and vinyl copolymers such as styrene/butadiene copolymers, acrylate/vinyl acetate copolymers, acrylonitrile/butadiene copolymers, ethylene/vinyl acetate copolymers, and silicone resins other than POSS resins as defined herein. In some embodiments, the at least one film forming agent is a cellulosic resin.

Certain embodiments of the polymerizable liquid composition of the present disclosure may comprise a non-reactive, solvent-dissolvable polymer.

According to an aspect, the non-reactive, solvent-dissolvable polymer is a cellulose ester. According to a particular aspect, the non-reactive, solvent-dissolvable polymer is a cellulose acetate alkylate.

According to a more particular aspect, the non-reactive, solvent-dissolvable polymer is a cellulose acetate butyrate or a cellulose acetate propionate. The non-reactive, solvent-dissolvable polymer may be a mixture of any acceptable polymer.

According to a further aspect, the non-reactive, solvent-dissolvable polymer may be present at from about 0 to about 75 wt %.

The removable, adhesion-promoting nail coating composition may comprise a non-reactive, solvent-dissolvable polymer selected from the group consisting of ethyl tosylamide, adipic acid/fumaric acid/phthalic acid/tricyclodecane dimethanol copolymer, adipic acid/neopentyl glycol/trimellitic anhydride copolymer, phthalic anhydride/trimellitic anhydride/glycols copolymer, polyethyl cellulose, polyhydroxypropyl cellulose, polyethyl acrylate oxide, poly lactic acid, nitrocellulose, cellulose ester, and mixtures thereof.

Cellulosic Resins as Film Forming Agents

According to some embodiments, the at least one film forming agent is at least one cellulosic resin. In some specific embodiments, the cellulosic resin is the major film former in the enamel.

In some specific embodiments, the silicon resin and cellulosic resin are combined in a ratio of silicon resin to cellulosic resin from about 1:10 to about 1:1. This includes, but is not limited to, from about 1:10 to about 1:4, from about 1:10 to about 1:6, from about 1:10 to about 1:8, from about 1:2 to about 1:1, from about 1:4 to about 1:1, from about 1:6 to about 1:1, from about 1:8 to about 1:1; from about 1:8 to about 1:4, from about 1:6 to about 1:4, from about 1:6 to about 1:2, and from about 1:8 to about 1:2.

In some specific embodiments, the cellulosic resin is nitrocellulose or other cellulose derivative, such as a cellulose ester, cellulose acetate alkylate (e.g., cellulose acetate propionate, cellulose acetate butyrate) and ethyl cellulose.

Nitrocellulose and cellulose esters useful in accordance with the present invention are identified in U.S. Pat. No. 6,333,025, the text of which is hereby incorporated by reference.

In some specific embodiments, the cellulosic resin is a nitrocellulose. In specific embodiments, Nitrocellulose is present in the nail coating composition in an amount ranging from about 1.5% by weight and 35% by weight relative to the total weight of the composition; or about 8% by weight and 20% by weight, relative to the total weight of the composition.

In some embodiments of the invention, the nail coatings may also include at least one film forming agent. In specific, non-limiting embodiments, the film forming agent is present in an amount up to 50% by weight; or an amount less than 40% by weight, relative to the total weight of cellulose resin. In some specific embodiments, the amount of additional film forming agent ranges from about 1% by weight and 15% by weight relative to the total weight of Non-limiting examples of film forming agents include polymers such as polyesters; resins, such as polyurethane resins, alkyd resins, and polyvinyl resins such as polyvinyl acetate, polyvinyl chloride, polyvinylbutyrate; (meth)acrylic and vinyl copolymers such as styrene/butadiene copolymers, acrylate/vinyl acetate copolymers, acrylonitrile/butadiene copolymers, and ethylene/vinyl acetate copolymers.

In some embodiments, the cellulosic resin is a cellulose ester. In some embodiments the cellulose ester is a cellulose acetate alkylate. The cellulose acetate alkylate may be selected from the group consisting of cellulose acetate butyrate, cellulose acetate propionate, and mixtures thereof.

Silicone Resins

"Silicone resins" refers to a variety of polymers which are characterized by repeating Si subunits having at least one and up to four oxygen bridges with other Si atoms. Of the four possible Si bonds, instead of oxygen bridges, up to three R groups can be present. By varying the subunits and substituents, a vast variety of polymers can be created. Silicone resins have been disclosed previously in U.S. Pat. No. 8,080,257, in which the silicone resins are used as a film forming agents in conjunction with a liquid fatty phase that includes at least one hydrocarbon based polymer that includes a hetero atom as part of the polymer skeleton.

In some embodiments, the silicone resin may be either a siloxysilicate or a polysiloxane. Siloxysilicates have the formula $[R_3—Si—O]_x—(SiO_{4/2})_y$, wherein x and y range from about 50 to about 80, and polysiloxanes have the formula $[R_3—Si—O]—(R_2SiO)_x—[Si—R_3]$, wherein X is at least 2000. The R groups can be, for example, an alkyl, hydroxyl, alkoxysilane, amine, chlorosilane, epoxide, ester, halide, methacrylate, molecular silica, nitrile, norbornene, olefin, phosphine, silane, silanol, styrenic polymer, or polyolefin.

In yet another instance, the siloxysilicate is of the formula $[R_3—Si—O]_x—(SiO_{4/2})_y$, wherein x and y range from about 50 to about 80, and R is an alkyl, hydroxyl, alkoxysilane, amine, chlorosilane, epoxide, ester, halide, methacrylate, molecular silica, nitrile, norbornene, olefin, phosphine, silane, silanol, styrenic polymer, or polyolefin.

In another instance, the siloxysilicate is a trimethylsiloxysilicate.

In some embodiments, the polysiloxane is of the formula $[R_3—Si—O]—(R_2SiO)_x—[Si—R_3]$, wherein X is at least 2000, and R is an alkyl, hydroxyl, alkoxysilane, amine, chlorosilane, epoxide, ester, halide, methacrylate, molecular silica, nitrile, norbornene, olefin, phosphine, silane, silanol, styrenic polymer, or polyolefin. In some embodiments, the polysiloxane is dimethicone.

Silicone resins are named in accordance with what is referred to in the art as "MDTQ" nomenclature, whereby a silicone resin is described depending upon the various monomeric siloxane subunits ("Si subunits") which form the polymer. Each letter, "M," "D," "T" and "Q" stands for a different subunit. "M" denotes the monofunctional unit $(CH_3)_3SiO_{1/2}$. This unit is referred to as monofunctional because the silicone atom shares only one oxygen with another Si atom in the chain. The "M" unit can be represented by the structure:

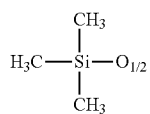

At least one of the methyl groups can be replaced, as demonstrated by the formula $R(CH_3)_2SiO_{1/2}$, where R can be a substituent other than a methyl group, for example a functional group or a longer alkyl group that may include functional groups as represented by the structure:

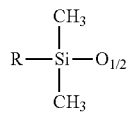

One or more of the methyl groups can be replaced by an R group which may be the same or different.

The letter "D" denotes the difunctional subunit $(CH_3)_2SiO_{2/2}$ where two of the available bonds from the silicone atom are bound to oxygen in the formation of the polymeric chain. The "D" subunit can be represented as:

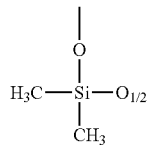

As is the case in connection with the M subunit, one or more methyl groups may be replaced with the same or different R groups as defined above.

The symbol "T" denotes the trifunctional subunit, $(CH_3)SiO_{3/2}$ and can be represented as:

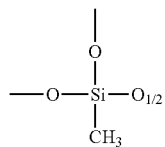

As illustrated above in connection with the "M" subunit, a methyl group can be replaced in the "T" subunits with another R group as defined above.

Finally, the symbol "Q" denotes the quadrifunctional subunit $SiO_{4/2}$ which can be represented as:

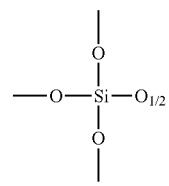

From this description, it is apparent that by varying the number and types of subunits, "M", "D", "T" and "Q", and by varying the methyl or R groups, a vast number of combinations can be created.

In some embodiments, the silicone resin is a Q resin. By the term Q resin, it is meant that the resin contains predominantly Si subunits of the Q type, or that those of skill in the art would regard the particular resin predominantly as a Q resin. MQ resins are also referred to as "siloxysilicates", such as trimethylsiloxysilicates, represented by the following formula: $[(CH_3)_3-Si-O]_x-(SiO_{4/2})_y$ (MQ Units) where x and y can have values ranging from 50 to 80.

In a further embodiment, the silicone resin is a siloxysilicate chosen from any combination of M and Q units, for example, $[(R)_3-Si-O]_x-(SiO_{4/2})_y$, wherein x and y can have values ranging from 50 to 80 and at least one R group is chosen from an alkyl group other than a methyl group, for example functional group or a longer hydrocarbon chain that may be functionalized. For example, a Q resin can be chosen from among the Wacker 803 and 804 resins, available from Wacker Silicone Corporation, and G.E. 1,170 002, available from General Electric.

The term "silsesquioxane" generally refers to a class of silicone resins of the T type ("T resins"). In some embodiments, the silicone resin can be chosen from silsesquioxanes represented by the following formula: $(CH_3SiO_{3/2})_x$ (T Units) where x has a value of up to several thousand and the methyl may be replaced by another R group as described above for the M subunits. Note, however, that where a polymethylsilsesquioxane is employed, it is not combined with a POSS (Polyhedral Oligomeric Silsesquioxane) of the type having only 8 fully saturated Si subunits (complete cage of $R_1$ to $R_8$ methyl groups, as defined further below). Polymethylsilsesquioxanes are those silsesquioxanes wherein each substituent (R group) is a methyl group.

In some embodiments, the silicone resin is a "polyalkylsiloxane" or D resin. Again, by the term "D resin" it is meant that the resin contains predominantly Si subunits of the D type, or that those of skill in the art would regard the particular resin predominantly as a D resin.

In some embodiments, the polysiloxane is of the formula $[R_3-Si-O]-(R_2SiO)_x-[Si-R_3]$, wherein X is at least 2000, and R is an alkyl, hydroxyl, alkoxysilane, amine, chlorosilane, epoxide, ester, halide, methacrylate, molecular silica, nitrile, norbornene, olefin, phosphine, silane, silanol, styrenic polymer, or polyolefin. D resins include dimethylsiloxanes having the CTFA designation dimethicone. These siloxanes are available commercially from the General Electric Company as the Viscasil Series and from Dow Corning as the DC200 series.

Substituted Silicone Resins

As stated previously, the M, D and T subunits may include one or more substituents (R groups). As non-limiting examples, these R groups include an alkyl, hydroxyl, alkoxysilane, amine, chlorosilane, epoxide, ester, halide, methacrylate, molecular silica, nitrile, norbornene, olefin, phosphine, silane, silanol, styrenic polymer or polyolefin.

More than one substitution can be made, wherein one, two or more of the methyl groups available are replaced with the same or different R groups. These groups can be directly bonded to the Si atom, or may be bound through a bridging moiety that may contain other functional groups, such as an azo, diazo, epoxy or halogen, which may be reactive functional groups.

Polyhedral Oligomeric Silsesquioxanes or 'POSS'

Various embodiments of the present invention incorporate Polyhedral Oligomeric (or Oligo) Silsequioxane (POSS). In some embodiments, the POSS is an extended Polyhedral Oligomeric (or Oligo) Silsequioxane (EPOSS) molecule containing six or more Si atoms within its cage like structure Silsesquioxane (POSS) into nail coatings. These compounds are distinguished from other silicone resins by their rigid three-dimensional cage-like structures. In some embodiments, the POSS used in the present embodiments has a three dimensional cage structure formed of a plurality of Si subunits, i.e. Si—O subunits, at least one of the subunits having one or more R groups.

In some embodiments, the term "POSS" may refer to POSS molecules having 8 Si atoms or less (e.g., 6, 7 or 8), while EPOSS may be used to refer to structures those cage structures having greater than 8 Si atoms. All silicone resins forming cage structures may be used in the present embodiments. Accordingly, unless indicated otherwise, the term "POSS" refers to POSS or EPOSS molecules regardless of the number of Si atoms.

POSS are inorganic materials with a siloxane core and reactive functional groups on the surface and represented by the general formula of $RSiO_{1.5}$. Generally POSS are nano-sized, but may be larger depending upon the number of Si and O atoms in the structure, as well as substituents that might be present as described elsewhere herein. Cubic silsesquioxanes, such as octa(dimethylsiloxy) silsequioxanesilsesquioxane ($R_8Si_8O_{12}$), consist of a rigid, crystalline silica-like core that is well-defined spatially (0.5-0.7 nm) which can be linked covalently to eight (8) R groups.

A description of possible cages is discussed in U.S. Pat. No. 5,942,638, which is incorporated by reference in its entirety. Each of the cages can be further modified by attaching reactive moieties to the cage atoms. Depending upon the substituents, the core can account for approximately 5%, or 10%, or 15%, or 20%, or 25%, or 30%, or 35%, or 40%, or 45%, or 50%, or 55%, or 60%, or 65%, or 70%, or 75%, or 80%, or 85%, of the total volume and the highly enhanced surface effects. The structure of the organic phase between the rigid, hard particles can be varied systematically; the potential exists to carefully tune mechanical, optical properties to establish structure-property relationships.

For example, by varying the functionality of the R group, it is possible to create multi-functionalized macromonomers, for example octa-functional macromonomers that will self-polymerize or copolymerize with other functionalized cubes to provide nanocomposites whose length scales and interfacial interactions are well-defined. The structure of the organic phase between the rigid, hard particles can be varied systematically; the potential exists to carefully tune mechanical, and/or optical properties to establish structure property relationships. Also, by varying the functionality of the R group it is possible to enhance physical and chemical interactions between a nail surface and the coating or between coating layers in a multi-layer system to provide for the enhanced adhesion observed.

In some embodiments, POSS refers to only those compounds existing in a rigid, "cage"-type configuration, examples of which are shown in Formulas I-V, below. In some embodiments, POSS refers to only certain structures, such as, by way of non-limiting examples, those illustrated in Formulas I, III and IVA, which are referred to herein as being "complete cages" wherein all of the sides of the three-dimensional structure are completed sides and all of the Si atoms are completely saturated.

In some embodiments, the nail coatings (nail coating or nail topcoat) do not include other POSS that can exist, for example, in the ladder configuration of Formula VI. For example, the polymethylsilsesquioxane known as Resin MK, has previously been disclosed in connection with cosmetic formulations in U.S. Publication No. US2002/0114773, which is incorporated by reference in its entirety. As disclosed therein, the belief is that the compounds exist in both a "cage" (i.e., Formula I, wherein $R_1$-$R_8$ are $CH_3$—) and "ladder" configuration (Formula VI).

It is also believed that the majority of the silicone polymers are present in the "ladder" configuration (Formula VI). To the extent that this composition contains the "ladder" configuration, it is not POSS as that term is used with respect to the present invention.

The POSS used in the nail coatings of the present embodiments may form the three-dimensional cage structure.

In some embodiments, the POSS has at least six Si molecules. In some embodiments, the POSS contains eight Si atoms. POSS may also include greater than eight Si atoms or in mixtures containing, for example, six to twelve Si atoms or eight to twelve Si atoms, for example as a mixture of compounds containing eight, ten and twelve Si atoms. The number of Si atoms can also range from six to one hundred, alternatively six to thirty, also alternatively six to twenty and finally alternatively six to sixteen, either as a single POSS structure (i.e. having the same configuration of Si and O atoms even if other substituents vary) or as a mixture of compounds with varying numbers of Si atoms with the same or varying R groups. In some embodiments, at least four of the Si atoms are bound, through an oxygen atom, to at least three other Si atoms (referred to herein as being "completely saturated"). All of the Si atoms are bound to at least one other Si atom through an oxygen bridge.

As shown in the exemplary and non-limiting structures of Formulas I through V and VII through X, POSS forms a rigid three-dimensional cage structure having at least two completed sides. This rigid cage structure is distinguished from ladders and other structures which are not held in place in three directions (see, e.g., Formula VI for an exemplary ladder structure). Each of the Si atoms is bound to at least one R group with no more than three, no more than two or no more than one Si atom being bound to more than two R groups. For example, the POSS molecule illustrated by Formula III has six saturated Si atoms and five complete sides—two sides bounded by three Si atoms connected through oxygen bridges and three sides bounded by four Si atoms connected through oxygen bridges. Formula IIB has four such saturated Si atoms and two completed sides—both bounded by four Si atoms connected through oxygen bridges. Formula IIC has six saturated Si atoms and three completed sides all bounded by four Si atoms connected through oxygen bridges.

POSS molecules in accordance with some embodiments have the complete cage structure of Formula I:

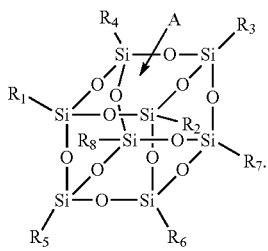

Formula IIA

It is also possible that one or even two of the oxygen bridges between successive Si atoms are broken or missing, in which case the "PO SS" is referred to as having an "incomplete" casecage structure. By way of non-limiting examples, consider the rigid three-dimensional cage structures illustrated in Formulas IIA-E:

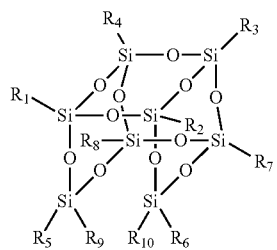

Formula IIA

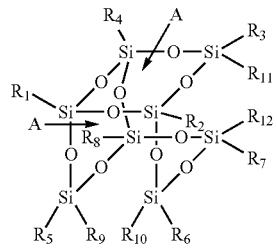

Formula IIB

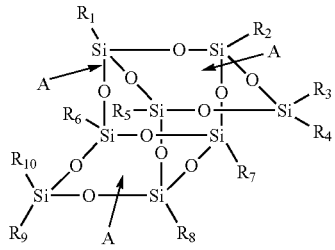

Formula IIC

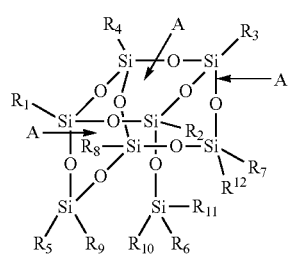

Formula IID

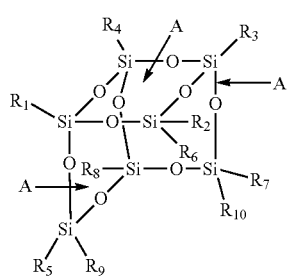

Formula IIE

Formula III is a complete cage, but produced from six Si atoms:

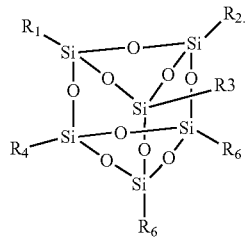

Formula III

In Formula IVA, the number of Si atoms in the cage is ten:

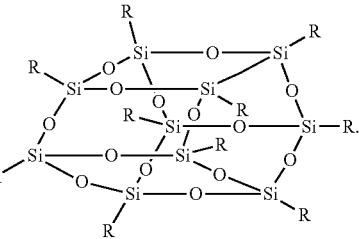

Formula IVA

In Formula IVB, the number of Si atoms is ten:

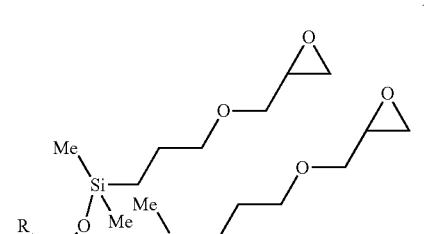

Formula IB

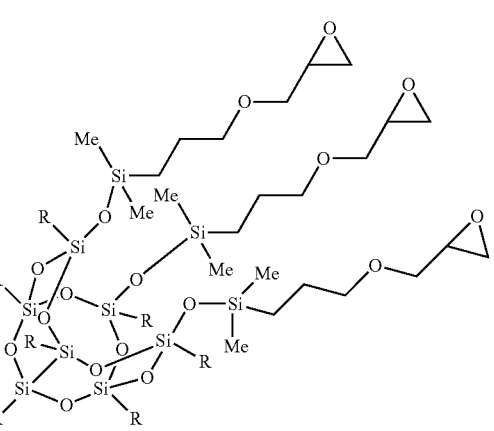

In Formula IVC, the number of Si atoms in the cage is twelve:

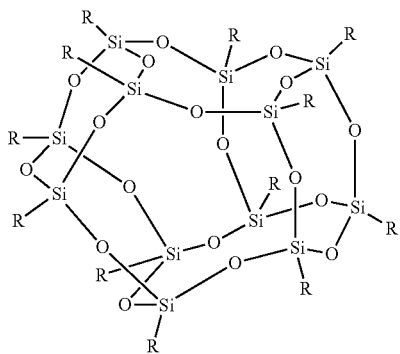

Formula IVC

In Formula IVD, the number of Si atoms in the cage or core is sixteen:

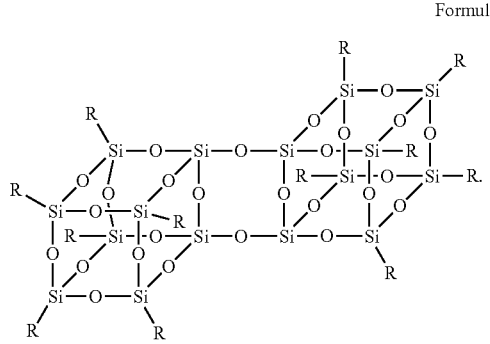

Formula IVD

In Formula WE, the number of Si atoms in the cage or core is sixteen:

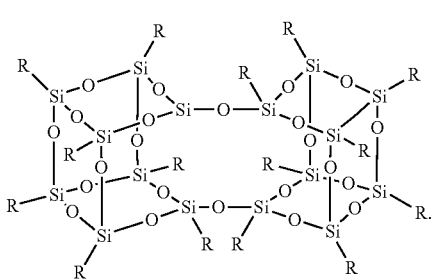

Formula IVE

An example of an "incomplete" cage structure, wherein one or more of the oxygen bridges between successive Si atoms is broken or missing, is illustrated in Formula V:

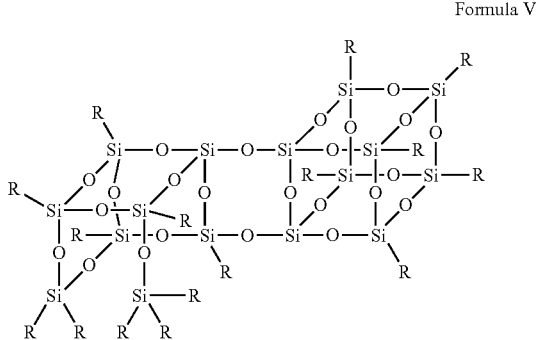

Formula V

Formula VI, a ladder configuration (not a POSS as defined herein), can be a monomer linked end to end to other similar structures. It is not rigid as it can fold or flex around each R—Si—O—Si—R axis of the molecule. No such movement is possible in the rigid 3-D cage structures (whether complete or incomplete) of the POSS of the present embodiments. Thus, the molecules of this formula are not POSS.

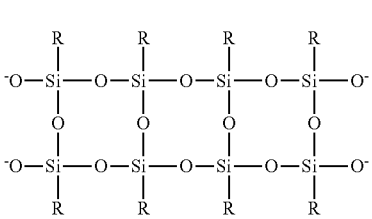

Formula VI

Note also that when referencing POSS molecules as being in accordance with Formula II, having the structure of Formula II, or being other than a completed cage, the sides which are illustrated as "open," "missing" or "broken" are illustrative only. When reference is made to Formula II, it is understood that any one or two sides, or any one or two oxygen bridges, may be broken or missing. The structure of the POSS molecule can be roughly thought of as a box (prism in the case of Formula III) or cage shape with silicon (Si) atoms at each corner. Each Si atom is connected to at least one other Si atom through bonds to an oxygen atom (also referred to as an "oxygen bridge").

In specific embodiments, at least four of the Si atoms in the POSS structure are "completely saturated." As used herein, a Si atom is "completely saturated" if bound, through oxygen atoms, to three other Si atoms within the cage as shown in Formulas I, III and IVA, most preferably, all of the Si atoms are "completely saturated". While illustrated in Formula I as Si atoms, the groups at each corner may be the same or different and may be one or more atoms or groups including, without limitation, silicon, silane, siloxane, silicone or organometallic groups.

The POSS used in the compositions described herein can have a rigid 3-dimensional cage structure as illustrated, for example, in Formulas I-V and VII-X and the cage has at least two completed sides A. Each Si is bound to at least one R group. In some embodiments no more than one Si atom is bound to more than two R groups. In some embodiments no more than two Si atoms are bound to more than two R groups. In some embodiments no more than three Si atoms are bound to more than two R groups.

In some embodiments, POSS materials can be represented by the formula $[RSiO_{1.5}]\infty$ where $\infty$ represents molar degree of polymerization and R represents an organic substituent (H, siloxy, cyclic or linear aliphatic or aromatic groups that may additionally contain reactive functionalities such as alcohols, esters, amines, ketones, olefins, ethers or halides or which may contain fluorinated groups). The POSS used may be either homoleptic or heteroleptic. Homoleptic systems contain only one type of R group while heteroleptic systems contain more than one type of R group.

In some specific embodiments, the internal cage-like framework is primarily comprised of inorganic silicon-oxygen bonds, while the exterior of the nanostructure is covered by both reactive and/or nonreactive organic functionalities (R), which ensure compatibility and tailorability of the nanostructure with organic monomers and polymers.

POSS and POSS nanostructure compositions are represented by the formulas:

$[(RSiO_{1.5})_n]_{\Sigma\#}$ for homoleptic compositions, $[(RSiO_{1.5})_n(R'SiO_{1.5})_m]_{\Sigma\#}$ for heteroleptic compositions (where R≠R').

$[(RSiO_{1.5})_n(XSiO_{1.5})_m]_{\Sigma\#}$ for functionalized heteroleptic compositions having a closed cage structure (where R groups can be equivalent or inequivalent). A functionalized heteroleptic POSS composition having an open cage structure may be represented by the formula $[(RSiO_{1.5})_n(RX-SiO_{1.0})_m]_{\Sigma\#}$.

By way of example, homoleptic POSS Formulas III, I, IVA and IVC are designated as $[(RSiO_{1.5})_6]_{\Sigma 6}$, $[(RSiO_{1.5})_6]_{\Sigma 6}$, $[(RSiO_{1.5})_8]_{\Sigma 8}$, $[(RSiO_{1.5})_{10}]_{\Sigma 10}$, and $[(RSiO_{1.5})_{12}]_{\Sigma 12}$, respectively. Similarly, functionalized heteroleptic open cage POSS can have the following structures and designations:

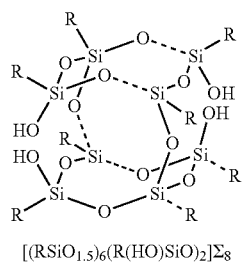

$[(RSiO_{1.5})_6(R(HO)SiO)_2]_{\Sigma 8}$

Formula VII

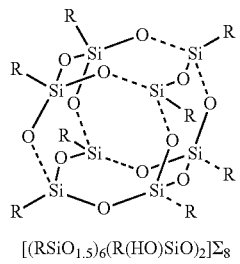

$[(RSiO_{1.5})_6(R(HO)SiO)_2]_{\Sigma 8}$

Formula VIII

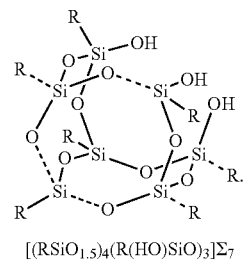

$[(RSiO_{1.5})_4(R(HO)SiO)_3]_{\Sigma 7}$

Formula IX

In all of the above structures and formulas, R is the same or different and can be any of the moieties as defined elsewhere herein and X includes but is not limited to OH, Cl, Br, I, alkoxide (OR), acetate ($COCH_3$), acid (COOH), ester (COOR), peroxide (OOR), amine ($NR_2$), isocyanate (NCO), epoxy, olefin and R. The symbols m and n refer to the stoichiometry of the composition. The symbol Σ indicates that the composition forms a nanostructure and the symbol # refers to the number of silicon (Si) atoms contained within the nanostructure. The value for # is usually the sum of m+n, where n ranges typically from one to twenty-four and m ranges typically from one to twelve. It should be noted that Σ# is not to be confused as a multiplier for determining stoichiometry, as it merely describes the overall nanostructural characteristics of the system (aka cage size).

Examples of attributes that enable the nanostructure described above to function as 1-10 nm reinforcing and adhesion promoting agents include: their unique size with respect to polymer chain dimensions, and their ability to be compatibilized with polymer systems to overcome repulsive forces that promote incompatibility and expulsion of the nanoreinforcing agent by the polymer chains. That is, nanostructured chemicals can be tailored to exhibit preferential affinity/compatibility with a wide range of nail coating compositions through variation of the R groups on each nanostructure.

At the same time, the nanostructureds can be tailored to be incompatible or compatible with other microstructures within the same polymer, thus allowing for selective reinforcement of specific polymer microstructure. Therefore, the factors to effect a selective nano-reinforcement include specific nanosizes of nanostructures, distributions of nanosizes, and compatibilities and disparities between the nanostrucuture and the polymer nail coating system. For POSS, dispersion of the molecules and their compatibility with polymer segments is thermodynamically governed by the free energy of mixing equation ($\Delta G=\Delta H-T\Delta S$). The nature of the R group and ability of the reactive groups on the POSS cage to react or interact with polymers and surfaces greatly contributes to a favorable enthalpic ($\Delta H$) term while the entropic term ($\Delta S$) for POSS is highly favorable because of the monoscopic cage size and distribution of 1.0.

Substituted POSS

The POSS used in the present invention is typically "derivatized" with one or more R groups that include a functional group. Other R groups may not include functional groups, but can be varied to modify the POSS by, for example, enhancing compatibility with solvents or other components of the nail coating, varying the size of the POSS to alter physical characteristics of the final coating, or enhancing solubility of the POSS in the nail coating. As non-limiting examples, one or more R groups could be an alkyl group, alkene, alkyne, hydroxyl, thiol, ester, acid, ether. In some embodiments, the "R groups" include, without limitation, one or more of the following: hydrogen, methyl, ethyl, propyl, isobutyl, isooctyl, phenyl, cyclopentyl, cyclohexyl, cycloheptyl, —$OSi(CH_3)_2$—$CH_2$—$CH_2$—$(CF_2)_5CF_3$, —$(CH_2)_3SH$, $N^+(CH_3)_3$, $O^-N^+CH_3)_3$, —OH, —$(CH_2)_nN^+H_3X^-$ wherein n is 0-30 and X is a counterion,

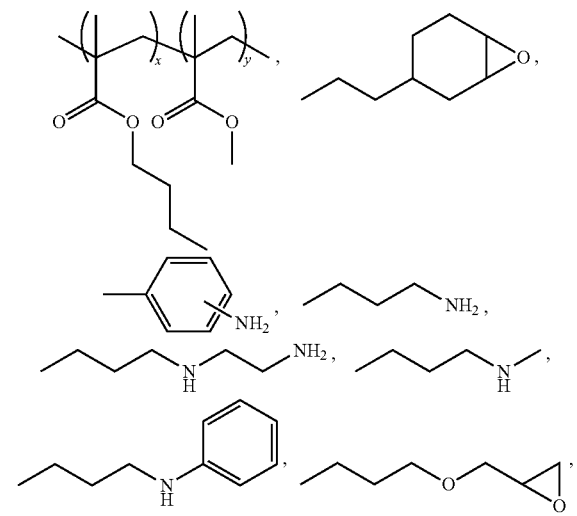

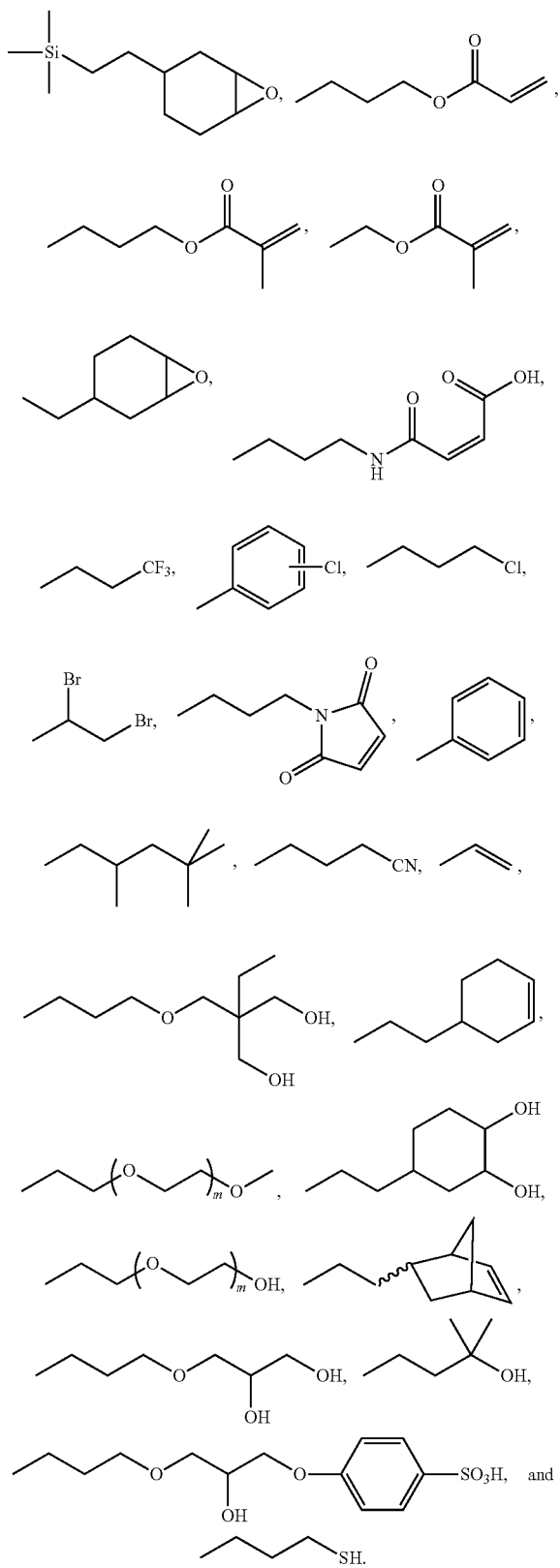

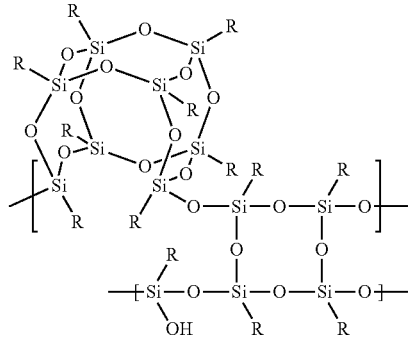

Formula X

As previously illustrated (see Formulas IVD and WE), the substituent can be an additional cage structure. In these instances, the structure can be considered conceptually as either a single POSS structure, as identified above, or as a POSS structure substituted by another POSS structure.

For example, the one remaining bond of each silicon of Formula I, III and IVA can bind to a variety of substituents or groups specified, as "R" groups ($R_1$-$R_8$), ($R_1$-$R_6$) in Formula III. As used herein, when multiple R groups are present on the same POSS molecule, each R group may be the same or different whether all are designated as simply R or differentiated as $R_1$, $R_2$, $R_3$, ... $R_n$. In some embodiments illustrated in Formulas II, IVB and V a POSS molecule in which one or two of the oxygen bridges between adjacent silicon molecules have been eliminated, a greater number of R groups are possible. In specific embodiments, when a POSS having 8 Si atoms is used, no more than two of these inter-silicon connections (oxygen bridges) are eliminated.

However, it is possible to eliminate as many as three such bridges (Formula IIE). In some embodiments, only a single oxygen bridge is eliminated (Formula IIA). As stated above, the Si molecules not completely bound may have one or more additional positions available for binding additional substituents. In the case of a single missing side, the POSS molecule may include additional R groups $R_9$ and $R_{10}$, which may be the same or different as the $R_1$-$R_8$. When 2 or 3 bridges are missing, the POSS molecule may include additional R groups $R_9$, $R_{10}$, $R_{11}$ and $R_{12}$ (as appropriate), which all may be the same or different and may be the same as the groups identified for $R_1$-$R_8$.

POSS compounds with various R groups are known in the literature. They are described in a number of patents including, without limitation, U.S. Pat. Nos. 5,047,492; 5,389,726; 5,484,867; 5,589,562; 5,750,741; 5,858,544; 5,939,576; 5,942,638; 6,100,417; 6,127,557; 6,207,364; 6,252,030; 6,270,561; 6,277,451; 6,362,279; and 6,486,254. These patents describe in detail various methods of producing the basic POSS cage structure and various derivatives thereof, including POSS based polymers.

To the extent that these patents identify and describe various POSS molecules having the structures of Formulas I-V and VII-X, derivatives and polymers thereof, they are incorporated by reference. The discussions of techniques for manufacturing and derivatizing this class of compounds described in each of these patents is also hereby incorporated by reference.

In general, R groups (for example, $R_1$, $R_2$, $R_3$, $R_4$, $R_5$, $R_6$, $R_7$, $R_8$, $R_9$, $R_{10}$, $R_{11}$ and $R_{12}$ as shown in the figures and any other R groups appropriate) can be the same or different and may be reactive or nonreactive groups. They may be, in In some embodiments, R can also be a silane or siloxane structure, including a ladder structure. Formula X is a non-limiting example of a siloxane substituted POSS:

replacing a methyl or H, for example, hydroxy (—OH), alkane derivatives (missing a hydrogen) also known as alkyl groups (other than methyl), alkenyl groups also referred to as derivatives of alkenes (having one or more double bonds), usually missing an H where they are bound to Si in POSS or to some other molecule, alkynyl groups also referred to as derivatives of alkynes (having one or more triple bonds) usually missing an H where they are bound to Si in POSS or to some other molecule, aryl groups (either the 6-carbon ring of benzene or the condensed 6-carbon rings of other aromatic derivatives such as naphthalene) also referred to as derivatives of arenes, usually missing an H where they are bound to Si in POSS or to some other molecule, heteroaryl groups (either a 6-membered or 5-membered aromatic ring containing one or more atoms other than carbon in the ring, e.g. N, S or O, or structures containing condensed heteroaromatic rings) acyl groups (organic acids without the OH group, e.g., $CH_3CO$— or $C_6H_5CO$—), alkoxy groups (alkyl radicals attached to the remainder of a molecule by oxygen), such as methoxy, ester groups, acid groups, acrylate groups, alkyl acrylate groups, hydroxy groups, halogens, amino groups, alkylamino groups, aminoalkyl groups, groups containing one or more tertiary or quaternary nitrogens, silicone containing groups, sulfur containing groups, epoxides, azo groups, diazo groups, halogens, cyclic compounds which can undergo ring opening polymerization or ring opening metathesis polymerization. R groups may also be monomers or polymers where POSS will be used as a pendant substituent of the polymer. Acrylates and cationic polymers providing conditioning properties are provided in some embodiments.

Where appropriate, any of these R groups may themselves be substituted or unsubstituted, saturated or unsaturated, linear or branched. Possible substitutions include $C_1$-$C_{30}$ alkyl groups, $C_1$-$C_{30}$ alkenyl groups, $C_1$-$C_{30}$ alkynyl groups, $C_6$-$C_{18}$ aryl groups, acyl groups, alkoxy or other groups, carboxy groups, ester groups, acrylate groups, alkyl acrylate groups, trihydroxy groups, amino groups, alkylamino groups including mono and dialkylamino groups, mono and dihydroxy alkylamino groups, cyano groups, aminoalkyl groups, groups containing one or more tertiary or quaternary nitrogens, silicone containing groups, sulfur and/or phosphorous containing groups, $SO_2X$, $SO_3X$, where X is H, methyl or ethyl, epoxides and epoxide containing groups, azo groups, diazo groups, halogens, cyclic compounds which can undergo ring opening polymerization or ring opening metathesis polymerization. Indeed, any group which can be attached to a corner of a POSS molecule can be used.

When these R groups are carbon containing fatty acids or fatty alcohols, aromatic or cyclic groups, they generally may contain between 6 and 50 carbon atoms and may be saturated or unsaturated, substituted as discussed above or unsubstituted and branched or linear, as appropriate for a given group.

More specifically, possible R groups include, without limitation, hydroxy groups including mono or poly hydroxy groups, phenols, alkoxy, hydroxy alkyls, silanes, amino and in particular, quats, halosilanes, epoxides, alkyl carbonyls, alkanes, haloalkyls, halogens, acrylates, methacrylates, thiols, nitriles, norbornenyls, branched alkyl groups, polymers, silanes, silanols, styryls and thiols. In a single POSS molecule of Formula I, $R_1$ could be H, $R_2$—OH, $R_3$—$NH$, $R_4$—$CH_2CH_2N^+CH_3(OCH_2CH_3)CH_2CH_2CH_3$, $R_5$—$CH_2CH_2CHO_2CH_2$ (epoxide), $R_6$—$OC(CH_3)_3$, $R_7$—$OOC(CH_2)_{16}CH_3$ and $R_8$ could be $C_1$. This is a hypothetical example, merely to illustrate that each of the R groups can be derivatized separately and to emphasize the wide variety of possible substitutions.

In some embodiments, these POSS molecules are not completely substituted with the same R groups (e.g., not all $R_1$-$R_6$, $R_1$-$R_{10}$ or $R_1$-$R_{12}$ (and any other R groups, as appropriate, given the number of Si atoms and available bonds in a given POSS molecule) are methyl, isobutyl or phenyl). This is particularly preferred for POSS molecules that have the structure of Formula I. Moreover, when a POSS molecule having eight (8) Si subunits, as depicted in Formula I, is employed, at least one of the R groups is a group other than a methyl, particularly where the silicon resin is a T resin and, even more particularly, Resin MK.

Also contemplated under the term POSS is the family of commercially available compounds available from Hybrid Plastics, 55 W.L. Runnels Industrial Drive Hattiesburg, Miss. 39401 and Mayaterials, Inc. P.O. Box 87, South Lyon, Mich. 48178-0087. According to the manufacturers, these commercially available materials break down into several general categories.

In some embodiments, the POSS used in the coatings (nail coating or nail topcoat) of the present embodiments has the formula of $(C_6H_{11}O_2)_n(SiO_{1.5})_n$, where n is 6 (see Formula III), 8 (see Formula I), 10 (see Formula IVA), or 12 (see Formula IVC) and $C_6H_{11}O_2$ represents a glycidyl epoxide having the structure:

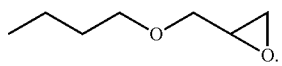

In some embodiments, the POSS used in the coatings of the present embodiments is a mixture of POSS structures having the formula $(C_6H_{11}O_2)_n(SiO_{1.5})_n$, where n is 6, 8, 10, and 12. In some embodiments, the POSS used in the coatings of the present embodiments is a mixture of POSS structures having the formula $(C_6H_{11}O_2)_n(SiO_{1.5})_n$, where n is 8, 10 and 12. In some embodiments, the POSS used in the coatings of the present embodiments is a mixture of POSS structures having the formula of $(C_6H_{11}O_2)_n(SiO_{1.5})_n$, where n is 8 and 10.

In some embodiments, the POSS molecules are functionalized with at least one group or a plurality of groups. Examples of functional groups on the polymer and POSS materials include, but are not limited to, functional silicones—for example, hydroxy, urethane, acrylate, vinyl, Si—H, amides, MQ or T groups, functional acrylates, functional polyamides, Poly(9-vinylcarbazole) (PVK), Polyvinyl Acetate (PVA), Polystyrene (PS), Polyethylene Glycol (PEG), Polypropylene Glycol (PPG), polysaccharides or modified starch, functional block copolymers, functional polyesters and polyethers, fluorinated polymers and wax to bring about the cross-linking reaction between the polymer chains and POSS materials to provide desired properties.

Non-limiting examples of suitable POSS compounds include dodecaphenyl, octaisobutyl and octamethyl POSS. POSS hybrid chemical compounds have molecular level functional ingredients and are commercially available from Hybrid Plastics (Fountain Valley, Calif.). More specifically, the POSS compounds include, but are not limited to, the following:
1-[3-(allylbisphenol A)propyldimethylsiloxy]-3,5,7,9,11,13, 15-heptacyclopentylpentacyclo [9.5.1.13,9.15,15.17,13] octasiloxane;

1-[3(allylbiphenol)propyldimethylsiloxy]-3,5,7,9,11,13,15-heptacyclopentylpentacyclo [9.5.1.13,9.15,15.17,13]octasiloxane;

1-[3-(1,3-propanediol-2-ethyl-2-methyloxy)propyldimethylsiloxy]-3,5,7,9,11,13,15-heptacyclopentylpentacyclo [9.5.1.13,9.15,15.17,13]octasiloxane;

1-[(2-methyl-2-hydroxy)butyldimethylsiloxy]-3,5,7,9,11,13,15-heptacyclopentylpentacyclo [9.5.1.13,9.15,15.17,13]octasiloxane;

1-[3-(ethoxydimethylsilyl)propyl]-3,5,7,9,11,13,15heptacyclopentylpentacyclo[9.5.1.13,9.15,15.17,13]octasiloxane;

1-[2-(diethoxymethylsilyl)propyl]-5,7,9,11,13,15-heptacyclopentylpentacyclo [9.5.1.13,9.15,15.17,13]octasiloxane 1-[3-(triethoxysilyl)propyl]-3,5,7,9,11,13,15-heptacyclopentylpentacyclo [9.5.1.13,9.15,15.17,13]octasiloxane;

1-[2-(ethoxydimethylsilyl)ethyl]-3,5,7,9,11,13,15-heptacyclopentylpentacyclo [9.5.1.13,9.15,15.17,13]octasiloxane;

1-[2-(diethoxymethylsilyl)propyl]-3,5,7,9,11,13,15-heptacyclopentylpentacyclo clo[9.5.1.13,9.15,15.17,13]octasiloxane;

1-[2-(triethoxysilyl)propyl]-3,5,7,9,11,13,15-heptacyclopentylpentacyclo [9.5.1.13,9.15,15.17,13]octasiloxane;

POSS BisPhenol A urethanes

POSS DiMethylol urethanes;

1-chloro-3,5,7,9,11,13,15-heptacyclopentylpentacyclo [9.5.1.13,9.15,15.17,13]octasiloxane;

1-[2-(chlorodimethylsilyl)ethyl]-3,5,7,9,11,13,15-heptacyclopentylpentacyclo [9.5.1.13,9.15,15.17,13]octasiloxane;

1-[2-(dichloromethylsilyl)ethyl]-3,5,7,9,11,13,15-heptacyclopentylpentacyclo[9.5.1.13,9.15,15.17,13]octasiloxane;

1 [2 (trichlorosilyl)ethyl]-3,5,7,9,11,13,15-heptacyclopentylpentacyclo[9.5.1.13,9.15,15.17,13]octasiloxane;

1-[3-(chlorodimethylsilyl)propyl]-3,5,7,9,11,13,15-heptacyclopentylpentacyclo[9.5.1.13,9.15,15.17,13]octasiloxane;

1-[3-(dichloromethylsilyl)propyl] 3,5,7,9,11,13,15-heptacyclopentylpentacyclo[9.5.1.13,9.15,15.17,13]octasiloxane;

1-[3-(trichlorosilyl)propyl] 3,5,7,9,11,13,15-heptacyclopentylpentacyclo[9.5.1.13,9.15,15.17,13]octasiloxane;

1,3,5,7,9,11,13,15-[2 (chlorodimethylsilyl)ethyl]pentacyclo [9.5.1.13,9.15,15.17,13]octasiloxane;

1,3,5,7,9,11,13,15-[2 (chlorodimethylsilyl)ethyl]pentacyclo [9.5.1.13,9.15,15.17,13]octasiloxane;

1,3,5,7,9,11,13,15-[2 (dichlorodimethylsilyl)ethyl]pentacyclo[9.5.1.13,9.15,15.17,13]octasiloxane;

1-[(2-epoxy)propyl]-3,5,7,9,11,13,15-heptacyclopentylpentacyclo[9.5.1.13,9.15,15.17,13]octasiloxane;

1-[2-(cyclohexyl 3 epoxy)ethyl]-3,5,7,9,11,13,15-heptacyclopentylpentacyclo [9.5.1.13,9.15,15.17,13]octasiloxane;

POSS diepoxide resins;

1,3,5,7,9 octavinyl-11,13,15-epoxyethylpentacyclo [9.5.1.1.3,9.1.15,15.1.17,13]octasiloxane;

endo 3,7,14 tris[1 (3 dimethylsiloxy)propyloxy 2,3 epoxypropyl]-1,3,5,7,9,11,14, heptacyclopentyltricyclo[7.3.3.1,5,11]heptasiloxane;

1-(methylpropionato)-3,5,7,9,11,13,15-heptacyclopentylpentacyclo[9.5.1.1.3,9.15,15.17,13]octasiloxane;

1-(ethylundecanoato)-3,5,7,9,11,13,15-heptacyclopentylpentacyclo[9.5.1.1.3,9.15,15.17,13]octasiloxane;

1-(3chloro)propyl]-3,5,7,9,11,13,15-heptacyclopentylpentacyclo[9.5.1.13,9.15,15.17,13] octasiloxane;

1-[4-chlorophenyl]-3,5,7,9,11,13,15-heptacyclopentylpentacyclo[9.5.1.13,9.15,15.17,13]octasiloxane;

1-[chlorobenzyl]-3,5,7,9,11,13,15-heptacyclopentylpentacyclo[9.5.1.13,9.15,15.17,13]octasiloxane;

1-[2-(chlorobenzyl)ethyl-3,5,7,9,11,13,15-heptacyclopentylpenta cyclo[9.5.1.13,9.15,15.17,13]octasiloxane;

1-[3-(methacryl)propyl]-3,5,7,9,11,13,15-heptacyclopentacyclo[9.5.1.13,9.15,15.17,13]octasiloxane;

1-[3-(methacryl)propyldimethylsiloxy]-3,5,7,9,11,13,15-heptacyclopentylpentacyclo [9.5.1.13,9.15,15.17,13] octasiloxane 1-(3,3,3-trifluoropropyldimethylsiloxy-1,3,5,9,11,13,15-heptacyclopentyl-7-[3-(methacryl)propyl]-7-methyltetracyclo[9.5.1.15,11.19,15]octasiloxane;

1-(tridecafluoro-1,1,2,2-tetrahydrooctyldimethylsiloxy)-1,3,5,9,11,13,15-heptacyclopentyl-7-[3 (methacryl)propyl]-7-methyltetracyclo[9.5.1.15,11.19,15]octasiloxane;

1-(trimethylsiloxy)-1,3,5,9,11,13,15-heptacyclopentyl-7-[3-(methacryl)propyl]7ethyltetracyclo[9.5.1.15,11.19,15] octasiloxane;

1,3,5,7,9-pentavinyl-11,13,15-[1 hydroxy 2 (methacryl)ethyl]pentacyclo[9.5.1.13,9.15,15.17,13]octasiloxane;

1,3,5,7,9,11-hexacyclohexyltetracyclo[5.5.1.13,11.15,9] hexasiloxane;

1,3,5,7,9,11,13,15-octacyclohexylpentacyclo[9.5.1.13,9.15,15.17,13]octasiloxane;

1,3,5,7,9,11,13,15-octacyclopentylpentacyclo[9.5.1.13,9.15,15.17,13]octasiloxane;

1,3,5,7,9,11,13,15-octaphenylpentacyclo[9.5.1.13,9.15,15.17,13]octasiloxane;

1,3,5,7,9,11,13,15-octamethylpentacyclo[9.5.1.13,9.15,15.17,13]octasiloxane;

1,3,5,7,9,11,13,15-octakis(dimethylsilyloxy)pentacyclo [9.5.1.13,9,1.5,15.17,13]octasiloxane;

POSS modified Nylon 6;

1-[(3-cyano)propyl]-3,5,7,9,11,13,15-heptacyclopentylpentacyclo[9.5.1.13.9.15,15.17,13]octasiloxane;

1-[2-(Norbomen-2-yl)ethyl]-3,5,7,9,11,13,15-heptacyclopentylpentacyclo[9.5.1.13,9.15,15.17,13]octasiloxane;

1-[2-(Norbomen-2-yl) ethyldimethylsiloxy]-3,5,7,9,11,13,15-heptacyclopentylpentacyclo[9.5.1.13,9.15,15.17,13] octasiloxane;

poly(ethylnorbornenylPOSS co-norbornene);

1,1,3-(norbornenyldimethylsiloxy)- 1,3-dicyclohexyldisiloxane;

1-[3-(allylbisphenol A)propyldimethylsiloxy]-3,5,7,9,11,13,1 5-heptacyclopentylpentacyclo [9.5.1.13,9.15,15.17,13]octasiloxane;

1-[3-(allylbiphenol)propyldimethylsiloxy]-3,5,7,9,11,13,15-heptacyclopentylpentacyclo [9.5.1.13,9.15,15.17,13] octasiloxane;

1,3,5,7,9,11,13,15-octavinylpentacyclo[9.5.1.13,9.15,15.17,13]octasiloxane;

1-vinyl-3,5,7,9,11,13,15-heptacyclopentylpentacyclo [9.5.1.13,9.15,15.17,13]octasiloxane;

1-allyl-3,5,7,9,11,13,15-heptacyclopentylpentacyclo [9.5.1.13,9.15,15.17,13]octasiloxane;

1-[2-(cyclohexen-3-yl)ethyl]-3,5,7,9,11,13,15-heptacyclopentylpentacyclo[9.5.1.13,9.15,15.17,13]octasiloxane;

poly(dimethyl-co-methylvinyl-co-methylethylsiloxyPOSS)siloxane;

POSS diepoxide resins; POSS Bis Phenol A urethanes;

1-[2-(diphenylphosphino)ethyl]-3,5,7,9,11,13,15-heptacyclopentylpentacyclo [9.5.1.13,9.15,15.17,13]octasiloxane;

1-[2-(diphenylphosphino)propyl]-3,5,7,9,11,13,15-heptacyclopentylpentacyclo [9.5.1.13,9.15,15.17,13]octasiloxane;

1-hydrido-3,5,7,9,11,13,15-heptacyclopentylpentacyclo [9.5.1.13,9.15,15.17,13]octasiloxane;
1-[hydridodimethylsiloxy]-3,5,7,9,11,13,15-heptacyclopentylpentacyclo [9.5.1.13,9.15,15.17,13]octasiloxane;
endo 3,7,14 tri(dimethylsilylhydrido)-1,3,5,7,9,11,14-heptacycopentyltricyclo [7.3.3.15,15,11]heptasiloxane;
1,1,3,3-(hydridodimethylsiloxy)-1,3-dicyclohexyldisiloxane;
poly(dimethyl co-methylhydrido co-methylpropylPOSS)siloxanendo-3,7,14-trihydroxy-1,3,5,7,9,11,14-heptacyclopentyltricyclo[7.3.3.15,11]heptasiloxane;
endo-3,7,14-trihydroxy-1,3,5,7,9,1,14-heptacyclohexyltricyclo[7.3.3.15,11]heptasiloxane;
1-hydroxy-3,5,7,9,11,13,15-heptacyclopentylpentacyclo [9.5.10.13,9.15,15.17,13]octasiloxane;
1,1,3,3-(tetrahydroxy)-1,3-dicyclohexyldisiloxane;
1,3,5,7-(tetrahydroxy)-1,3,5,7-(tetraphenyl)cyclotetrasiloxane;
Endo-7,14-dihydroxy 3-(3,3,3-trifluoropropyldimethylsiloxy)-1,3,5,9,11,13,15-heptacyclopentyltricyclo[7.3.3.15, 11]octasiloxane;
1,3,5,7-(tetrahydroxy)-1,3,5,7-(tetraphenyl)cyclotetrasiloxane;
Endo-7,14-dihydroxy-3-(3,3,3-trifluoropropyldimethylsiloxy)-1,3,5,9,11,13,15-eptacyclopentyltricyclo [7.3.3.1.sup.5,11]octasiloxane;
1-[2-(styryl)ethyldimethylsiloxy]-3,5,7,9,11,13,15-heptacyclopentylpentacyclo [9.5.1.13,9.15,15.17,13]octasiloxane;
1-[(4-vinyl)phenyl]-3,5,7,9,11,13,15-heptacyclopentylpentacyclo [9.5.1.13,9.15,15.17,13]octasiloxane;
1-[2-(styryl)ethyl]-3,5,7,9,11,13,15-heptacyclopentylpentacyclo[9.5.1.13,9.15,15.17,13] octasiloxane;
TMP DiolCyclopentyl POSS™ (Aldrich Catalog No. 51,710-0, (St. Louis, Mo.)), Trans Cyclohexane-Diolisobutyl POSS™ (Aldrich Catalog No. 56,028-6), 1,2 PropaneDiolisobutyl POSS™ (Aldrich Catalog No. 56,030-8); Aminopropylisobutyl POSS™ (sold by Hybrid Plastics as AM0265); Aminoethylaminopropylisobutyl POSS™ (Aldrich Catalog No. 56,029-4); IsocyanatopropyldimethylsilylCyclopentyl POSS™ (Aldrich Catalog No. 52,734-3); MethacrylisobutylTitanium POSS; OctaAmmonium POSS™ (sold by Hybrid Plastics as AM0285); OctaAmmonium POSS Poly(styryl POSS co styrene); poly(vinylsilsesquioxane); and structures having 10 and 12 silicon atoms in the cage.

The POSS of the present invention may be prepared by hydrolytic condensation reactions of trifunctional organosilicone monomers, e.g. R Si(OMe). Methods of preparing POSS are described in U.S. Pat. Nos. 8,133,478 and 6,372,843, which are incorporated herein by reference in their entireties.

In some embodiments, the POSS used in the coatings of the present embodiments is Glycidyl POSS® Cage Mixture (sold by Hybrid Plastics as EP0409), which is a blend of caged and non-caged structures as described in, for example, U.S. Pat. Nos. 6,716,919 and 6,927,270, each of which is incorporated herein by reference in its entirety.

In some embodiments, the POSS used in the coatings of the present embodiments is Acrylo POSS Cage Mixture (sold by Hybrid Plastics as MA0736), Epoxycyclohexyl POSS Cage Mixture (sold by Hybrid Plastics as EP0408), NorbornenylethylDiSilanol-isobutyl POSS (sold by Hybrid Plastics as NB1038), TMP Diol-isobutyl POSS (sold by Hybrid Plastics as AL0104), Trans-Cyclohexanediol-isobutyl POSS (sold by Hybrid Plastics as AL0125), 1,2-Propanediol-isobutyl POSS (sold by Hybrid Plastics as AL0130), Octa(3-hydroxy-3-methylbutyldimethylsiloxy) POSS(sold by Hybrid Plastics as AL0136), Amic Acid-Cyclohexyl POSS (sold by Hybrid Plastics as CA0295), Maleamic Acid-Isobutyl POSS (sold by Hybrid Plastics as CA0296), OctaMaleamic Acid POSS (sold by Hybrid Plastics as CA0298), Epoxycyclohexylisobutyl POSS (sold by Hybrid Plastics as EP0402), Glycidylehtyl POSS (sold by Hybrid Plastics as EP0417), Glycidylisobutyl POSS (sold by Hybrid Plastics as EP0418), GlycidylPhenyl POSS (sold by Hybrid Plastics as EP0419), Tryblycidyl Cyclohexyl POSS (sold by Hybrid Plastics as EP0421), Tryglycidylisobutyl POSS (sold by Hybrid Plastics as EP0423), Octa Epoxycyclohexyl dimethylsilyl POSS (sold by Hybrid Plastics as EP0430), Octa-Glycidyldimethylsilyl POSS (sold by Hybrid Plastics as EP0435), Trifluoropropyl POSS Cage Mixture (sold by Hybrid Plastics as FL0578), Trifluoropropylisobutyl POSS (sold by Hybrid Plastics as FL0583), Chlorobenzylethylisobutyl POSS (sold by Hybrid Plastics as HA0605), Aminoethylaminopropylisobutyl POSS (sold by Hybrid Plastics as HA0615), Chloropropylisobutyl POSS (sold by Hybrid Plastics as HA0635), Octakis(dibromoethyl) POSS (sold by Hybrid Plastics as HA0640), Maleimide Cyclohexyl POSS (sold by Hybrid Plastics as IM0670), POSS Maleimide Isobutyl (sold by Hybrid Plastics as IM0673), Acryloisobutyl (sold by Hybrid Plastics as MA0701), Methacryloisobutyl POSS (sold by Hybrid Plastics as MA0702), Methacrylate Cyclohexyl POSS (sold by Hybrid Plastics as MA0703), Methacrylate Isobutyl POSS (sold by Hybrid Plastics as MA0706), Methacrylate Ethyl POSS (sold by Hybrid Plastics as MA0716), MethacrylEthyl POSS (sold by Hybrid Plastics as MA0717), Methacrylate Isooctyl POSS (sold by Hybrid Plastics as MA0718), Methacrylisooctyl POSS (sold by Hybrid Plastics as MA0719), MethacrylPhenyl POSS (sold by Hybrid Plastics as MA0734), Methacryl POSS Cage Mixture (sold by Hybrid Plastics as MA0735), Acrylo POSS Cage Mixture (sold by Hybrid Plastics as MA0736), DodecaPhenyl POSS (sold by Hybrid Plastics as MS0802), Isooctyl POSS Cage Mixture (sold by Hybrid Plastics as MS0805), Phenylisobutyl POSS (sold by Hybrid Plastics as MS0813), Phenylisooctyl POSS (sold by Hybrid Plastics as MS0814), IsooctylPhenyl POSS (sold by Hybrid Plastics as MS0815), Octaisobutyl POSS (sold by Hybrid Plastics as MS0825), OctaMethyl POSS (sold by Hybrid Plastics as MS0830), OctaPhenyl POSS (sold by Hybrid Plastics as MS0840), Octatetramethyl ammonium POSS (sold by Hybrid Plastics as MS0860), OctaTrimethylsiloxy POSS (sold by Hybrid Plastics as MS0865), Cyanopropylisobutyl POSS (sold by Hybrid Plastics as NI0914), (NB1000), 1,3-Bis(Norbornenylethyl)-1,1,3,3-tetramethyldisiloxane (NB1010, Norbornenylethyldimethylchlorosilane (sold by Hybrid Plastics as NB1017), Norbomenylethylethyl POSS (sold by Hybrid Plastics as NB1021), Norbornenylethylisobutyl POSS (sold by Hybrid Plastics as NB1022), NorbornenylethylDiSilanol-isobutyl POSS (sold by Hybrid Plastics as NB1038), Trisnorbornenyl-isobutyl POSS (sold by Hybrid Plastics as NB1070), Allysobutyl POSS (sold by Hybrid Plastics as OL1118), Vinyl-isobutyl POSS (sold by Hybrid Plastics as OL1123), Octacyclohexenyldimethylsilyl POSS (sold by Hybrid Plastics as OL1159), Octavinylsilsesquioxane POSS (sold by Hybrid Plastics as OL1160), OctaVinyldimethylsilyl POSS (sold by Hybrid Plastics as OL1163), Vinyl POSS Cage Mixture (sold by Hybrid Plastics as OL1170), PEG POSS Cage Mixture (sold by Hybrid Plastics as PG1190), OctaSilane POSS (sold by Hybrid Plastics as SH1310), Octahydrido POSS (sold by Hybrid Plastics as SH1311), TriSilanolCyclohexyl POSS (sold by Hybrid Plastics as SO1400), SO1440, TriSilanolEthyl POSS (sold by Hybrid Plastics as S01444), TriSilanolisobutyl POSS (sold by Hybrid Plastics as S01450), TriSilanolisooctyl POSS (sold by Hybrid Plastics as SO1455), TriSilanolPhenyl POSS (sold by Hybrid Plastics as S01457), TrisilanolPhenyl POSS (sold by Hybrid Plastics as SO1458), TetraSilanolPhenyl POSS (sold by Hybrid Plastics as SO1460), Tris sulfonic acid ethyl POSS (sold by Hybrid Plastics as SA1532), Tris Sulfonic Acid Isobutyl POSS (sold by Hybrid Plastics as SA1533), Mercaptopropylisobutyl POSS (sold by Hybrid Plastics as TH1550), Mercaptopropyl i-octyl POSS (sold by Hybrid Plastics as TH1555), OctaAmmonium POSS (sold by Hybrid Plastics as AM0285), Aminopropylphenyl POSS (sold by Hybrid Plastics as AM0273), Vinyl Silsesquioxane Resin (sold by Hybrid Plastics as PM1285MV), Octaaminophenyl POSS (sold by Hybrid Plastics as AM0280), N-Phenylaminopropyl POSS Cage Mixture (sold by Hybrid Plastics as AM0281), N-Methylaminopropylisobutyl POSS (sold by Hybrid Plastics as AM0282), p-Aminophenyl Cyclohexyl POSS (sold by Hybrid Plastics as AM0290), m-Aminophenyl Cyclohexyl POSS (sold by Hybrid Plastics as AM0291), p-Aminophenylisobutyl POSS (sold by Hybrid Plastics as AM0292), m-Aminophenylisobutyl POSS (sold by Hybrid Plastics as AM0293), Aminoethylaminopropylisobutyl POSS (sold by Hybrid Plastics as AM0275), Aminopropylisobutyl POSS (sold by Hybrid Plastics as AM0265), PEG POSS Cage Mixture (sold by Hybrid Plastics as PG1190), Aminopropylisooctyl POSS (sold by Hybrid Plastics as AM0270), or a mixture thereof.

POSS Molecular Silicas™

POSS Molecular Silicas™ possess a robust Si—O core surrounded by non-reactive organic groups ($R_1$-$R_8$) which permit the inorganic core to be compatible with an organic matrix. This allows POSS Molecular Silicas™ to be compounded into standard polymers yielding true nanocomposites with complete molecular level dispersion. The unique ability of POSS Molecular Silicas™ to be dispersed at the molecular level is the key to reinforcing polymer segments and coils leading to significant property enhancements.

POSS Silanols

POSS Silanols possess a hybrid inorganic organic three dimensional structure which contains from one to four stable silanol (Si—OH) groups.

POSS Functionalized Monomers

POSS Functionalized Monomers possess a hybrid inorganic-organic three-dimensional structure which contains from one to eight or more reactive organic functional groups. Although referred to herein as "monomers", it is to be understood that the term reactive organic functional groups include groups that can polymerizable groups or groups that can otherwise interact with additional nail coating components or other POSS molecules to enhance physical properties of the nail coating such as adhesion and toughness.

POSS Functionalized Monomers may contain non-reactive organic groups with one functionalized reactive group, multiple non-reactive organic groups and multiple functionalized reactive groups, or only functionalized reactive groups. For example, a POSS having eight R groups may contain seven non-reactive organic groups with one unique functionality functionalized reactive group, six non-reactive organic groups and two functionalized reactive groups, five non-reactive organic groups and three functionalized reactive groups, etc. up to a POSS containing eight functionalized reactive groups. Non-limiting examples of unique functional groups include, amines, esters, epoxides, methacrylates, olefins, silanes, styryls, and thiols.

By varying the functional group(s) and the non-reactive organic group(s), a multitude of POSS Functionalized Monomers can be prepared to meet almost any need. While the monofunctional POSS Monomers can be incorporated by copolymerization or grafting, multifunctional POSS Monomers, i.e. POSS containing more than one functionalized reactive group, can be utilized as effective cross-linkers.

POSS Functionalized Monomers react similarly in polymerization, grafting and cross-linking reactions to standard organic monomers. While they react like simple organic monomers, when incorporated into a polymeric material, POSS Functionalized Monomers impart significant improvements in the thermal, and mechanicalproperties of traditional coatings.

POSS Polymers and Resins

POSS Polymers and Resins possess a hybrid inorganic-organic composition and can be either thermoplastic or thermoset materials. As a class of materials, POSS Polymers and Resins are comprised of either: (1) polymers in which a POSS Functionalized Monomer has been co-polymerized or grafted onto a polymer chain; or (2) silsesquioxane resins possessing some cage structure (See, e.g. Formula X). POSS Polymers and Resins can be used as stand-alone replacements for traditional materials or they may be compounded or solution blended into traditional polymeric materials to enhance the properties of the base resin. Non-limiting examples of POSS Polymers and Resins include silicones, styrenics, acrylics, and norbornenes.

POSS molecules available from Hybrid Plastics include, without limitation, those based on Formulas I IV, and are selected from alcohols and phenols (such as TMP DiolCyclopentyl POSS, TMP DiolIsobutyl POSS, Trans CyclohexaneDiolCycohexyl POSS, Trans CyclohexaneDiolIsobutyl POSS, 1,2 PropaneDiolCyclohexyl POSS, 1,2 PropaneDiolIsobutyl POSS, and OctaHydroxypropyldimethylsilylPOSS), alkoxysilanes (such as DiethoxymethylsilylethylCycohexyl POSS, DiethoxymethylsilylethylIsobutyl POSS, DiethoxymethylsilylpropylCyclohexyl POSS, DiethoxymethylsilylpropylIsobutyl POSS, EthoxydimethylsilylethylCyclohexyl POSS, EthoxydimethylsilylethylIsobutyl POSS, EthoxydimethylsilylpropylCyclohexyl POSS (may contain some isomer), EthoxydimethylsilylpropylIsobutyl POSS (may contain some β isomer), TriethoxysilylethylCyclohexyl POSS, TriethoxysilylethylIsobutyl POSS, TriethoxysilylpropylCyclohexyl POSS (may contain some β isomer) and TriethyoxysilylpropylIsobutyl POSS (may contain some β isomer), amines (such as AminopropylCyclohexyl POSS, AminopropylIsobutyl POSS, AminopropylIsooctyl POSS, AminoethylaminopropylCyclohexyl POSS, AminoethylaminopropylIsobutyl POSS, OctaAminophenyl POSS and OctaAmmonium POSS), chlorosilanes (such as MonoChloroCyclohexyl POSS, MonoChloroCyclopentyl POSS, MonoChloroIsobutyl POSS, ChlorodimethylsilylethylCyclohexyl POSS, ChlorodimethylsilylethylIsobutyl POSS, ChlorodimethylsilylpropylCyclohexyl POSS (may contain some β isomer), chlorodimethylsilylpropylIsobutyl POSS (may contain some β isomer), DichloromethylsilylethylCyclohexyl POSS, DichloromethylsilylethylIsobutyl POSS, DichloromethylsilylpropylCyclohexyl POSS (may contain some β isomer), DichloromethylsilylpropylIsobutyl POSS (may contain some β isomer), TrichlorosilylethylCyclohexyl POSS, TrichlorosilylethylIsobutyl POSS, TrichlorosilylpropylCyclohexyl POSS (may contain some β isomer), TrichlorosilylpropylIsobutyl POSS (may contain some β isomer), Octa(chlorosilylethyl) POSS (may contain some β isomer), Octa(dichlorosilylethyl) POSS (may contain some β isomer) and Octa(trichlorosilylethyl) POSS (may contain some β isomer)), epoxides (such as EpoxyCyclohexylCyclohexyl POSS, EpoxyCyclohexylCyclopentyl POSS, EpoxyCyclohexylIsobutyl POSS, Epoxy-CyclohexylDisilanolIsobutyl POSS, EpoxyCyclohexyl POSS Cage Mixtures such as EpoxypropylCyclopentyl POSS, EpoxypropylIsobutyl POSS, GlycidylCyclohexyl POSS, GlycidylCyclopentyl POSS, GlycidylEthyl POSS, GlycidylIsobutyl POSS, GlycidylIsoctyl POSS, Glycidyl-Phenyl POSS, OctaEpoxyCyclohexyldimethylsilyl POSS, OctaGlycidyldimethylsilyl POSS, TrisGlycidylCyclohexyl POSS, TrisGlycidylCyclopentyl POSS, TrisGlycidylEthyl POSS and TrisGlycidylIsobutyl POSS), esters (such as EthylUndecanoateCyclohexyl POSS, EthylUndecanoateCyclopentyl POSS, EthylUndecanoateIsobutyl POSS, MethylPropionateCyclohexyl POSS, MethylPropionateCyclopentyl POSS and MethylPropionateIsobutyl POSS), fluoroalkyls (such as Fluoro(3)DisilanolCyclopentyl POSS, Fluoro(13)DisilanolCyclopentyl POSS, Fluoro(13)DisilanolIsobutyl POSS, MethacrylFluoro(3)Cyclopentyl POSS mixture of isomers, MethacrylFluoro(13)Cyclopentyl POSS mixture of isomers, MethacrylFluoro(3)Isobutyl POSS mixture of isomers, DodecaTrifluoropropyl POSS, TriFluoroCyclohexyl POSS, TriFluoroCyclopentyl POSS, TriFluoroIsobutyl POSS, TrifluoropropylIsobutyl POSS, TrisFluoro(3)Cyclopentyl POSS and TrisFluoro(13)Cyvlopentyl POSS), halides (such as ChlorobenzylCyclohexyl POSS, ChlorobenzylCyclopentyl POSS, ChlorobenzylIsobutyl POSS, ChlorobenzylethylCyclohexyl POSS, ChlorobenzylethylCyclopentyl POSS, ChlorobenzylethylIsobutyl POSS, ChlorophenylCyclohexyl POSS, ChlorophenylCyclopentyl POSS, ChlorophenylIsobutyl POSS, ChlorophenylPhenyl POSS, ChloropropylCyclohexyl POSS, ChloropropylCyclopentyl POSS and ChloropropylIsobutyl POSS), isocyanates (such as Isocyanatopropyldimethylsilyl Cyclohexyl POSS and IsocyanatopropyldimethylsilylIsobutyl POSS), methacrylates and acrylates (such as AcryloCyclohexyl POSS, AcryloCyclopentyl POSS, AcryloIsobutyl POSS, MethacrylCyclohexyl POSS, MethacrylCyclopentyl POSS, MethacrylEthyl POSS, MethacrylIsobutyl POSS, MethacrylIsooctyl POSS 90%, MethacrylPhenyl POSS, MethacrylDisilanolCyclohexyl POSS, MethacrylDisilanolCyclopentyl POSS, MethacrylDisilanolIsobutyl POSS, MethacrylFluoro(3)Cyclopentyl POSS, MethacrylFluoro(13)Cyclopentyl POSS, MethacryltrimethylsiloxyCyclopentyl POSS, MethacryltrimethylsiloxyIsobutyl POSS, Methacryl POSS Cage Mixture, OctaMethacryldimethylsilylPOSS, Tri sMethacrylCyclohexyl POSS and TrisMethacrylIsobutyl POSS), molecular silica (such as DodecaPhenyl POSS, DodecaPhenyl POSS, 85%, Isooctyl POSS Cage Mixture 95%, OctaCyclohexyl POSS, OctaCyclopentyl POSS, OctaIsobutyl POSS, OctaMethyl POSS, OctaPhenyl POSS, OctaTMA POSS, DodecaTrifluoropropyl POSS, OctaTrimethylsiloxy POSS, Phenethyl POSS Cage Mixture and PhenethylIsobutyl POSS), nitriles (such as CyanoethylCyclohexyl POSS, CyanoethylCyclopentyl POSS, CyanoethylIsobutyl POSS, CyanopropylCyclohexyl POSS, CyanopropylCyclopentyl POSS and CyanopropylIsobutyl POSS), norbornenyls (such as NorbornenylethylCyclohexyl POSS, NorbornenylethylIsobutyl POSS, NorbornenylethylDiSilanolCyclohexyl POSS, NorbornenylethylDiSilanolCyclopentyl POSS, NorbornenylethylDiSilanolIsobutyl POSS, Tris NorbornenylCyclohexyl POSS, Tris NorbornenylCyclopentyl POSS and Tris NorbornenylIsobutyl POSS), olefins (such as AllylCyclohexyl POSS, AllylCyclopentyl POSS, AllylIsobutyl POSS, AllylDimethylsilylCyclopentyl POSS, CyclohexenylethylCyclopentyl POSS, DimethylvinylCyclopentyl POSS, DiphenylvinylCyclopentyl POSS, MonoVinylCyclohexyl POSS, MonoVinylCyclopentyl POSS, MonoVinylIsobutyl POSS, PhenylMethylVinylCyclopentyl POSS, Tris(Dimethylvinyl) Isobutyl POSS, TrivinylsilylCyclopentyl POSS, OctaCyclohexenyldimethylsilylPOSS, OctaVinyldimethylsilyl POSS, OctaVinyl POSS and Vinyl POSS Cage Mixture), phosphines (such as DiphenylphosphinoethylCyclopentyl POSS and DiphenylphosphinopropylCyclopentyl POSS), polymers (such as Poly(dimethyl-co-methylhydrido-co-methylpropylPOSS)siloxane, Poly(dimethyl-co-methylvinyl co methylethylsiloxyPOSS)siloxane, OctaMethyl POSS Nanoreinforce™ Polypropylene, 10 wt %, Poly(ethylsilsesquixane) uncured, Poly(methylsilsesquioxane) uncured, Poly(phenylsilsesquioxane) uncured, Poly(propylmethacrylPOSS-co-methylmethacrylate), Poly(propylmethacrylPOSS-co-styrene), Poly(styrylPOSS-co-styrene), Poly(vinylsilsesquioxane) uncured and Poly(vinylsilsesquioxane) fully cured FireQuench™), silanes (such as DimethylsilaneCyclohexyl POSS, Dimethyl silaneCyclopentyl POSS Schwab Hydride, DimethylsilaneIsobutyl POSS, MonoSilaneCyclohexyl POSS, MonoSilaneIsobutyl POSS, OctaSilane POSS, Tris(Dimethylsilane) Cyclohexyl POSS, Tris(Dimethylsilane)Cyclopentyl POSS and Tris(Dimethylsilane)CycloIsobutyl POSS), silanols (such as Cyclohexenyldimethylsily DisilanolIsobutyl POSS, DimethylphenylDisilanolCyclopentyl POSS, DimethylvinylDisilanolCyclohexyl POSS, DimethylvinylDisilanolCyclopentyl POSS, DimethylvinylDisilanolIsobutyl POSS, Di SilanolCyclopentyl POSS, Di SilanolIsobutyl POSS, EpoxyCyclohexylDisilanolIsobutyl POSS, Fluoro(3)DisilanolCyclopentyl POSS, Fluoro(13)DisilanolCyclopentyl POSS, Fluoro(13)DisilanolIsobutyl POSS, MethacrylDisilanolCyclohexyl POSS, MethacrylDisilanolCyclopentyl POSS, MethacrylDisilanolIsobutyl POSS, MonoSilanolCyclohexyl POSS, MonoSilanolCyclopentyl POSS Schwabinol, MonoSilanolIsobutyl, NorbornenylethylDiSilanolCyclohexyl POSS, NorbornenylethylDiSilanolCyclopentyl POSS, NorbornenylethylDiSilanolIsobutyl POSS, TMS Di SilanolCyclohexyl POSS, TMS Di SilanolIsobutyl POSS, Tri SilanolCyclohexyl POSS, TriSilanolCyclopentyl POSS, TirSilanolEthyl POSS, TriSilanolIsobutyl POSS, TriSilanolIsooctyl POSS and TriSilanolPhenyl POSS), styrenes (such as StyrenylIsobutyl POSS, StyrylCyclohexyl POSS, StyrylCyclopentyl POSS and StyrylIsobutyl POSS), and thiols (such as MercaptopropylCyclohexyl POSS, MercaptopropyIsobutyl POSS and MercaptopropylIsooctyl POSS 90%). Other POSS products may be purchased from ALDRICH.

Still others are described in U.S. Pat. Nos. 8,133,478 and 5,047,492, the text of which, and in particular, the POSS molecules described in the passage of column 1, line 22 through column 2, line 48, are hereby incorporated by reference and U.S. Pat. No. 2,465,188, the text of which is also hereby incorporated by reference. See also U.S. Pat. No. 5,858,544, the text of which is also incorporated by reference.

In specific embodiments, the POSS molecules useful for producing coating compositions in accordance with the present embodiments include: TrisFluoro(13)Cyclopentyl-POSS (Catalog No. FL0590; $C_{65}H_{93}F_{39}O_{12}Si_{10}$; Mw: 2088.24 g/mole); MercaptopropylIsobutyl-POSS (Catalog No. TH1550; $C_{31}H_{70}O_{12}Si_8$; Mw: 891.63 g/mole); MercaptopropylIsooctyl-POSS (Catalog No. TH1555; $C_{59}H_{126}O_{12}Si_8$; Mw: 1284.37 g/mole); Poly(methacrylpropylisooctylPOSS-co-methymethacrylate) 60% wt (Catalog No. PM1275.4-60; Poly(MethacrylpropylisooctylPOSS-comethylmethacrylate) 80% wt. (Catalog No. PM1275.4-80; OctaIsobutyl-POSS (Catalog No. MS0825; $C_{32}H_{72}O_{12}Si_8$; Mw: 873.60 g/mole); OctaPhenyl-POSS (Catalog No. MS0840; $C_{48}H_{40}O_{12}Si_8$; Mw: 1033.53 g/mole); Isooctyl-POSS Cage Mixture, 95% (Catalog No. MS0805; $[Me_3CCH_2CH(Me)CH_2]_nTn$ n=8; $C_{64}H_{136}O_{12}Si_8$; Mw: 1322.46 g/mole based on n=8MS0805); EpoxyCyclohexyl-Cyclohexyl-POSS (Catalog No. EP0399; $C_{50}H_{90}O_{13}Si_8$; Mw: 1123.93 g/mole); EpoxyCyclohexylIsobutyl-POSS (Catalog No. EP0402; $C_{36}H_{76}O_{13}Si_8$; Mw: 941.66 g/mole); Glycidyl POSS Cage Mixture (Catalog No. EP0409); GlycidylCyclohexyl-POSS (Catalog No. EP0415; $C_{48}H_{88}O_{14}Si_8$; Mw: 1113.89 g/mole); GlycidylIsobutyl-POSS (Catalog No. EP0418); $C_{34}H_{74}O_{14}Si_8$; Mw: 931.63 g/mole); TrisGlycidylCyclohexyl-POSS (Catalog No. EP0421; $C_{66}H_{128}O_{18}Si_{10}$; Mw: 1490.57 g/mole); and OctaEpoxyCyclohexyldimethylsilyl-POSS (Catalog No. EP0430; $C_{80}H_{52}O_{28}Si_{16}$; Mw: 2011.41 g/mole); OctaAminophenyl-POSS (Catalog No. AM0280; $C_{48}H_{48}N_8O_{12}Si_8$; Mw: 1153.63 g/mole); OctaAminophenyl-POSS (Catalog No. AM0285; $C_{24}H_{72}CL_8N_8O_{12}Si_8$; Mw: 1 173.18 g/mole); and OctaTMA POSS (Catalog No. MS0860; $C_{32}H_{96}O_{20}Si_8$~$60H_2O$; Mw: 2218.75 g/mole). These POSS molecules can be purchased from Hybrid Plastics, 55 W.L. Runnels Industrial Drive Hattiesburg, Miss. 39401, USA and Mayaterials.

As previously noted and as reflected in the patents and publications previously incorporated by reference, there are many known POSS molecules and many known ways to produce POSS compounds and various derivatives and polymers thereof. In general, however, one process of producing POSS includes the following steps: a) providing a trifunctional polyhedral oligomeric silsesquioxane of the formula $Si_7R_7O_9(OA)_3$, where OA is OH, $OSb(CH_3)_4$, $OSn(CH_3)_3$, or OT1, and R is an alkyl, alkenyl, aryl, alkoxy group or other R group described herein; and b) corner capping said trifunctional polyhedral silsesquioxane by reacting said trifunctional polyhedral silsequioxane with a compound of the formula M Z to form a polyhedral oligomeric silsesquioxane having the formula $Si_7R_7O_{12}M(z)$. M is a silane, siloxane or organometallic group and Z is a reactive group.

As illustrated in the non-limiting examples set forth below, a variety of POSS structures can be used in nail coating compositions. In some cases, an existing nail coating composition can be enhanced (e.g., by demonstrating enhanced adhesion) by addition of a POSS to the composition. The POSS can be selected to provide a desirable set of physical properties for the system being modified and that exhibits compatibility with the particular nail coating system. In a solvent based system, it is desirable that the POSS be present in a form that is soluble in the relevant solvent. For example, in an aqueous system, it is desirable that the POSS be present in a form that is water soluble. The POSS should also be selected such that it does not react undesirably with other components of the nail coating system during storage and prior to use.

Consideration should also be given as to whether the POSS should react with other components of the system, for example by co-polymerization or other chemical reaction, or whether the POSS should interact primarily with either the nail surface, if applied as a single layer or a basecoat, or with another layer to promote interlaminar adhesion. The most desirable POSS for a particular application can be identified or selected based upon the desired properties and the substituents. Using routine experimentation, the organic groups (which can impart the desired properties such as solubility and reactivity) on the POSS can be varied or different POSS molecules tested to arrive at the optimal POSS for a particular system.

According to the present invention, nail coatings can be obtained by either adding an appropriate POSS component to an existing nail coating system or by formulating an entirely new system. The nail coating system may be, for example, a single layer system, such as an enamel containing only a film forming component, a single layer photocurable system that includes polymerizable monomers such as a gel or acrylic, a solvent based system that includes both a film-forming component and a polymerizable component, or a water based nail coating.

In various embodiments, the POSS is added in an amount of from about 0.01 wt % to about 20 wt % of the total composition before it is applied. In specific embodiments, the POSS is present in an amount of from about 0.05 wt % to about 10 wt %; from about 0.05 wt % to about 8 wt %; from about 0.05 wt % to about 5 wt %; from about 1 wt % to about 10 wt %; from about 1 wt % to about 8 wt %; from about 1 wt % to about 5 wt %; from about 2 wt % to about 10 wt %; from about 2 wt % to about 8 wt %; or from about 2 wt % to about 5 wt %. In some specific embodiments, the POSS is added in an amount of no greater than 20 wt %, no greater than 15 wt %, no greater than 10 wt %, no greater than 8 wt %, no greater than 5 wt %, no greater than 2 wt %, no greater than 1 wt %, or less.

In various embodiments, the POSS is added to an existing formulation directly; as a mixture with some other component of the system such as a solvent, film former such as a cellulosic polymer (e.g., a cellulose alkylate ester such as cellulose acetate butyrate or CAB), or a mixture of solvent and other components. Alternatively, the POSS may be incorporated during normal mixing and processing of used to prepare the nail coating composition.

Nail Enamels

Embodiments of the invention comprise a nail enamel composition for application to the nails which deposit a film on the nail after solvent evaporation. Nail enamel compositions are generally polymer based liquids with a film-forming polymer dissolved in an organic solvent such as an butyl acetate, ethyl acetate, isopropanol and the like, as well as mixtures thereof. After application to the nail, the solvent evaporates depositing the film forming composition and any pigments therein on the surface of the nail.

Polymerizable Nail Coatings (Gels, Acrylics and Hybrids)

Embodiments of the invention comprise a polymerizable composition for application to the nails and polymerization to yield a nail coating or an artificial nail structure. The polymerizable composition is preferably an anhydrous liquid, having the consistency of a semi-mobile gel to freely mobile liquid at room temperature. Immediately prior to use, the polymerizable composition is applied to the nail surface and shaped by the nail technician. After polymerization an artificial nail structure is obtained.

Water-Based Enamels

A water-based enamel nail coating formulation includes water as a solvent and a film-forming polymer. The water-based enamel nail coating formulation can include one or more of the following categories of components: a water-miscible (meth)acrylic acid polymer; a (meth)acrylate copolymer; a styrene-(meth)acrylate copolymer; a polyurethane film former and/or thickeners; an oligo- or polyoxyalkylene (e.g., a glycol ether, dipropylene glycol, n-butyl ether dipropylene glycol, a PEG or PPG, or diethylene glycol); a non-ionic soap; and a color agent. A water-based enamel is free of organic solvents such as ethyl acetate, butyl acetate, acetone, or the like. In some embodiments, a water-based enamel nail coating includes water, styrene acrylates copolymer (e.g., a styrene-(meth)acrylate copolymer), and acrylates copolymer (e.g., a (meth)acrylate copolymer).

Liquid-and-Powder Formulations

In some embodiments, a polymerizable nail coating is derived from the liquid-and-powder method. Immediately prior to use, an appropriate amount of a polymerizable nail coating composition comprised primarily of one or more liquid monomers is poured into a dish or other appropriate vessel. A brush or other shaping tool is dipped into the composition to form a small bead on the tip of the tool. This bead is then dipped into a polymer powder mixture, which is in a separate dish. Upon dipping the bead of liquid monomer on the brush into the polymer powder material, a doughy, adherent, agglomerated mass of particles is formed at the tip of the shaping tool. Alternatively, the powder can be slurried in the liquid to obtain a doughy mass, and the shaping tool is dipped into the doughy mass. Generally a ratio of 0.2 to 1.3 parts of polymer powder to 1 part of the liquid monomer composition will provide suitable polymerization. The liquid polymerizable nail coating composition softens and partially dissolves the powder. The tip of the shaping tool, with its load of doughy material is then used to sculpt a new nail shape on the nail surface. A polymerization initiator (e.g., a peroxide) in the powder and a polymerization accelerator (e.g., an amine) in the liquid monomer act together to catalyze polymerization of the monomer composition to result in an artificial nail structure, which is then shaped and polished as desired.

In order for the polymerizable composition to exhibit a desirable workability, the composition should be such that when a 1 to 0.5, respectively, mixture of the polymerizable composition and the above mentioned powdered catalyst are mixed and stored at 15° C., the mixture should gel to a viscosity of 100,000 centipoise in 400 to 1400 seconds, preferably 600 to 1200 seconds, most preferably 800 to 1000 seconds. Liquid-and-powder compositions and methods are described in, for example, U.S. Pat. No. 6,818,207, which is incorporated by reference in its entirety.

The liquid monomer composition can include one or more ethylenically unsaturated monomers, such as one or more (meth)acrylate monomers. It can also optionally include a multicarbonyl-vinyl containing monomer; a plasticizer; a polymerization accelerator; a UV absorber; a polymerization regulator. Such liquid monomer compositions are described in U.S. Pat. No. 6,818,207, which is incorporated by reference in its entirety.

Suitable polymer powders are preferably polymers or copolymers which contain at least some ethylenic unsaturation to permit cross-linking. The polymer powder mixture is generally comprised of a linear particulate chain-extended or cross-linked acrylate or methacrylate polymer, which may be in the random or block copolymer form. Most typically the acrylate or methacrylate polymer is ethyl- or methyl methacrylate or ethyl- or methyl acrylate, or a combination of one or more of these polymers. Most often a copolymer of ethyl- and methyl methacrylate is used. The polymer powder composition may also contain a polymerization accelerator, or catalyst, which is designed to work in conjunction with the accelerator found in the polymerizable composition. Most preferred is a peroxide, such as benzoyl peroxide. The polymer powder may also contain other ingredients such as titanium dioxide and other dyes and/or pigments.

The monomer composition may contain 0.001-5%, preferably 0.001-4%, or more preferably 0.005-3% by weight of a polymerization accelerator, or catalyst, which is preferably an aromatic or aliphatic tertiary amine. Suitable aliphatic or aromatic tertiary amines include those set forth on pages 1532-1534 of the C.T.F.A. Cosmetic Ingredient Dictionary and Handbook, Seventh Edition, 1997, which is hereby incorporated by reference.

Preferred are aromatic tertiary amines such as N,N-di($C_{1-6}$) alkyl-p-toluidines such as N,N-dimethyl-p-toluidine, N,N-diethyl-p-toluidine; or N,N-di($C_{1-6}$) alkyl anilines such as N,N-dimethyl aniline. The preferred accelerator is N,N-dimethyl-p-toluidine. The amine polymerization accelerator acts as a catalyst in chain extension and/or cross-linking of the monomers in the monomer composition.

In the case where the polymerizable composition is polymerized by chemical means in a liquid/powder system, the most commonly used accelerator is an amine, as mentioned above, in combination with an organic peroxide such as benzoyl peroxide. Generally, the amine accelerator is found in the monomer composition and the peroxide in the powdered composition which is mixed with the monomer composition to cause polymerization immediately prior to application of the composition to the nail, as discussed above.

Reactive Monomers, and/or Oligomers, and/or Polymers

An embodiment of the liquid composition comprises reactive monomers, and/or oligomers, and/or polymers which provide the polymerized composition increased adhesion. In certain embodiments, such reactive monomers, and/or oligomers, and/or polymers can include an ethylenically unsaturated reactant, for example, a (meth)acrylate. As it is known to persons of skill in the polymer arts, the term (meth)acrylate encompasses acrylates and/or methacrylates. According to an aspect, such reactive monomers, and/or oligomers, and/or polymers may be selected from the group consisting of chloride, bromide or iodide.

In some embodiments, the process further includes a step of adding silver perchlorate to a solution of the polyhedral oligomeric silsesquioxane in aqueous acetone to convert reactive group Z to an alcohol. See, U.S. Pat. No. 5,484,867. POSS molecules may also be made as described in a paper entitled "Polyhedral Oligosilsesquioxanes and Heterosilsesquioxanes" by Frank J. Feher of the Department of Chemistry of the University of California at Irvine, Calif. 92697, USA, available from Gelest, Inc., the test of which is hereby incorporated by reference herein.

Mixtures of POSS molecules are specifically contemplated. Indeed, mixtures of POSS molecules with EPOSS molecules containing nine or more Si atoms within their cage like structure are also contemplated. EPOSS molecules are also available commercially from Hybrid Plastics.

According to an aspect, such reactive monomers, and/or oligomers, and/or polymers may possess acidic functionality. According to an aspect, the monomer, oligomer or polymer which provides the polymerized composition increased adhesiveness is present from about 0 wt % to about 50 wt %. In specific embodiments, the polymerized composition increased adhesiveness is present from about 0.1 wt % to about 50 wt %; or from about 0.5 wt % to about 50 wt %; or from about 1 wt % to about 50 wt %; or from about 1 wt % to about 40 wt %; or from about 1 wt % to about 30 wt %; or from about 1 wt % to about 20 wt %; or from about 10 wt % to about 50 wt %; or from about 10 wt % to about 40 wt %; or from about 10 wt % to about 30 wt %; or from about 10 wt % to about 20 wt %.

In various embodiments, the ethylenically unsaturated reactant is mono-, di-, tri-, or poly-functional as regards the addition-polymerizable ethylenic bonds. A multiplicity of ethylenically unsaturated reactants are suitable, so long as the reactants are capable of polymerization to yield a polymerized artificial nail structure upon exposure to the appropriate stimuli. Suitable ethylenically unsaturated reactants are disclosed in U.S. Pat. No. 6,818,207, which is incorporated by reference herein.

Plasticizers

The nail coating of the present embodiments may also include an amount of plasticizer, which can be chosen by a person skilled in the art on the basis of his or her general knowledge, so as to obtain a composition which has cosmetically acceptable properties. Plasticizers useful in the presently disclosed nail coating composition include plasticizers commonly employed in nail enamel compositions. Non-limiting examples of plasticizers include dibutyl phthalate, dioctyl phthalate, tricresyl phthalate, butyl phthalate, dibutoxy ethyl phthalate, diamylphthalate, tosyl amide, N-ethyl-tosyl amide, sucrose acetate isobutyrate, camphor, castor oil, citrate esters, glyceryl diesters, glyceryl triesters, tributy phosphate, triphenyl phosphate, butyl glycolate, benzyl benzoate, butyl acetyl ricinoleate, butyl stearate, and dibutyl tartrate.

Additional examples of plasticizers suitable for use in the present invention, alone or as a mixture, include: glycols and derivatives thereof such as diethylene glycol ethyl ether, diethylene glycol methyl ether, diethylene glycol butyl ether, diethylene glycol hexyl ether, ethylene glycol ethyl ether, ethylene glycol butyl ether and ethylene glycol hexyl ether; glycerol esters; propylene glycol derivatives including propylene glycol phenyl ether, propylene glycol diacetate, dipropylene glycol butyl ether, tripropylene glycol butyl ether, propylene glycol methyl ether, dipropylene glycol ethyl ether, tripropylene glycol methyl ether, diethylene glycol methyl ether and propylene glycol butyl ether; acid esters, including carboxylic acid esters, such as citrates, phthalates, adipates, carbonates, tartrates, phosphates and sebacates; and oxyethylenated derivatives, including oxyethylenated oils, for example, plant oils such as castor oil; and mixtures thereof.

According to some embodiments, the plasticizer is a biodegradable plasticizer. In various specific embodiments, the plasticizer is an acetylated monoglyceride or an alkyl citrate.

In some specific embodiments, the alkyl citrates contemplated for use in the present embodiments are those resulting from esterification of citric acid with alcohols containing three or more carbon atoms, for example, tripropyl citrate, tributyl citrate, trihexyl citrate, etc. These esters may be derived from either primary or secondary alcohols. Esters derived from glycol and glycerol ethers containing one or more unetherified hydroxyl groups are also suitable plasticizers of similar characteristics.

In some specific embodiments, the plasticizer is a mixture of acetyl tributyl amide and N-ethyl tosyl amide. In these embodiments, the plasticizer is present in an amount of from about 3% to about 12% by weight relative to the weight of the composition.

In various specific embodiments, the plasticizer is triethyl citrate (TEC); acetyl triethyl citrate (ATEC); tributyl citrate (TBC); acetyl tributyl citrate (ATBC); citrate (TOC); acetyl trioctyl citrate (ATOC); trihexyl citrate (THC); acetyl trihexyl citrate (ATHC); butyryl trihexyl citrate (BTHC, trihexyl o butyryl citrate); trimethyl citrate (TMC); or alkyl sulphonic acid phenyl ester (ASE). In some specific embodiments, the plasticizer is vinyl chloride copolymer; or 1,2-cyclohexane dicarboxylic acid diisononyl ester.

In some specific embodiments, the plasticizer is a tri(lower alkyl) citrate, including but not limited to, triethyl citrate, tributyl citrate and triamyl citrate.

In some embodiments, the plasticizer is an acyl tri(lower alkyl) citrate where the alkyl group contains 2-4 carbon atoms. This includes, but is not limited to, acetyl triethyl citrate and acetyl tributyl citrate.

The compositions of the invention may contain from about 0.001 wt % to about 20 wt % of a plasticizer. The compositions of the invention may contain from about 0.01 wt % to about 15 wt %, from about 0.05 wt % to about 10 wt %, from about 0.1 wt % to about 5 wt %, or from about 0.5 wt % to about 2 wt % of a plasticizer.

The plasticizer causes the polymerized nail structure to have improved flexibility and reduced brittleness. Suitable plasticizers may be esters, low volatility solvents, or non-ionic materials such as nonionic organic surfactants or silicones.

In certain embodiments, the removable, adhesion-promoting nail coating composition further comprises from about 0.001 wt % to about 20 wt %, from about 0.01 wt % to about 15 wt %, from about 0.05 wt % to about 10 wt %, from about 0.1 wt % to about 5 wt %, or from about 0.5 wt % to about 2 wt % of a plasticizer selected from the group consisting of esters, low volatility solvents (paraffinic hydrocarbons, butyrolactone, xylene, methyl isobutyl ketone), non-ionic surfactants, non-ionic silicones, isostearyl isononanoate, silicones, diisobutyl adipate, trimethyl pentanyl diisobutyrate, acetyl tributyl citrate, and mixtures thereof.

Suitable esters include those having the general structure RCO—OR' where RCO— represents a carboxylic acid radical and where —OR' is an alcohol residue. Preferably R and R' are fatty radicals, having 6 to 30 carbon atoms, and may be saturated or unsaturated. Examples of suitable esters are those set forth on pages 1558 to 1564 of the C.T.F.A. Cosmetic Ingredient Dictionary and Handbook, Seventh Edition, 1997, which is hereby incorporated by reference.

In the preferred compositions of the invention, the plasticizer is an ester of the formula RCO—OR' wherein R and R' are each independently a straight or branched chain $C_{6-30}$ alkyl. A suitable plasticizer is isostearyl isononanoate. Other suitable plasticizers are disclosed in U.S. Pat. No. 6,818,207 which is incorporated by reference.

Color Agents

"Colorants" or "coloring agents" useful in the nail coating compositions of the invention may include, for example, pigments, including nacreous pigments, solid particles (for example, glitter flakes) and liposoluble colorants. Pigments may be white, transparent or colored, and mineral and/or organic. Among the mineral pigments which may be mentioned are titanium dioxide, optionally surface treated, zirconium oxide or cerium oxide, and iron oxide or chromium oxide, manganese violet, ultramarine blue, chromium hydrate and ferric blue. Among the organic pigments which may be mentioned are carbon black, pigments of D&C type, and lakes based on cochineal carmine or on barium, strontium, calcium or aluminum.

Conventional coloring agents can be used, and examples include inorganic pigments such as titanium dioxide, iron oxides, titanated mica, iron oxide coated mica, ultramarine, chromium oxide, chromium hydroxide, manganese violet, bismuth oxychloride, guanine, and aluminum; pearlescent materials; and organic coloring agents such as ferric ammonium ferrocyanide, and D&C Red Nos. 6, 7, 34; Blue No. 1; Violet No. 2; and Yellow No. 5.

In some specific embodiments, the color agent is one or more lake pigments. A "lake pigment" is a pigment manufactured by precipitating a dye with an inert binder, or "mordant", usually a metallic salt. The metallic salt or binder used is typically inert and insoluble in the vehicle, and is typically white or very neutral. In some embodiments, the metallic salt or binder has low tinting strength so that the dye itself determines which wavelengths are absorbed and reflected by the resulting precipitate.

In various embodiments, the colorant can also include one or more pigments. These pigments can be white or colored, and inorganic or organic. Non-limiting examples of inorganic pigments include titanium dioxide, which has optionally been surface treated, zirconium oxide and cerium oxide, as well as iron oxide and chromium oxide, manganese violet, ultramarine blue, chromium hydrate and ferric blue, and metallic pigments such as aluminum and bronze. Non-limiting examples of organic pigments include carbon black, pigments of D&C type and lakes based on cochineal carmine, barium, strontium, calcium, aluminum, and guanine.

The nacreous pigments can be chosen from white nacreous pigments such as mica coated with titanium or with bismuth oxychloride, colored nacreous pigments such as titanium mica with, for example, iron oxides, ferric blue, chromium oxide, or with an organic pigment of the above mentioned type, as well as nacreous pigments based on bismuth oxychloride.

The inorganic pigments may be surface treated as is customary to prevent migration or striation. Silicones and polyethylenes are most often used as the coatings for inorganic pigments and thus may be used according to the present invention.

Colorant materials may also include chips or powder of mica or diamonds in the nail coating composition. Also useful are specialty materials giving rise to two tone color effects such as liquid crystal silicones or multi lamellar metallic particulates, which generally can be mixed with pigments or dyes to obtain a broader spectrum of brilliant color and increased luminous reflectance. Such materials are described in, e.g., U.S. Pat. Nos. 3,438,796; 4,410,570; 4,434,010; 4,838,648; 4,930,866; 5,171,363; 5,364,467; 5,569,535; 5,607,904; 5,624,486; 5,658,976; 5,688,494; 5,766,335; N. Hatberle et al., "Right and Left Circular Polarizing Colorfilters made from Crosslinkable Cholesteric LC Silicones," Conference Record of the 1991 International Display Research Conference (IEEE), pp. 57-59; R. Maurer et al., "Polarizing Color Filters made from Cholesteric LC Silicones," SID 90 Digest (1990), pp. 110-113; H. J. Eberle et al., "Inverse Angle Dependence of the Reflection Colours of Cholesteric Polymeric Liquid Crystals Mixed with Pigments," Liquid Crystals, 5(3), (1989), pp. 907-916; J. Pinsl et al., "Liquid Crystalline Polysiloxanes for Optical Once Write Storage," J. Molec. Electr., Vol. 3 (1987), pp. 9-13; and D. Makow, "Reflection and Transmission of Polymer Liquid Crystal Coatings and their Application to Decorative Arts and Stained Glass," Color Res. Applic. Vol. 11, No. 3, (1986), pp. 205-208, all of which are incorporated herein by reference in its entirety.

In some specific embodiments, the solvent used in the coatings of the present embodiments is an organic solvent. In various embodiments, the solvent used in the coatings of the present embodiments is a polar organic solvent. Non-limiting examples of solvents include acetone, butyl acetate, isopropyl alcohol, ethanol, ethyl acetate, methyl ethyl ketone, and mixtures thereof. In specific embodiments, the solvent is acetone; butyl acetate; or ethyl acetate. In some embodiments, the solvent is butyl acetate, ethyl acetate, and mixtures thereof.

In some specific embodiments, the solvent is acetone, butyl acetate, butylene glycol, dipropylene glycol, disiloxane, ethyl acetate, ethyl ether, heptane, hexylene glycol, ethanol (denatured), isopropyl alcohol, limonene, n-butyl alcohol, propyl acetate, propylene carbonate, or propylene glycol.

In some specific embodiments, the solvent is ethyl acetate, butyl acetate, ethanol (denatured), isopropyl alcohol, acetone or mixtures and combinations thereof.

In some specific embodiments, the solvent is a ketone which is liquid at room temperature, such as methyl ethyl ketone, methyl isobutyl ketone, diisobutyl ketone, isophorone, cyclohexanone and acetone.

In some specific embodiments, the solvent is an alcohol, such as ethanol, isopropanol, diacetone alcohol, 2-butoxyethanol and cyclohexanol.

In some specific embodiments, the solvent is a glycol such as ethylene glycol, propylene glycol, pentylene glycol and glycerol.

In some specific embodiments, the solvent is a propylene glycol ether which is liquid at room temperature, such as propylene glycol monomethyl ether, propylene glycol monomethyl ether acetate and dipropylene glycol mono n-butyl ether.

In some specific embodiments, the solvent is a short chain ester (containing from 3 to 8 carbon atoms in total), such as ethyl acetate, methyl acetate, propyl acetate, n-butyl acetate and isopentyl acetate.

In some specific embodiments, the solvent is an ether which is liquid at room temperature, such as diethyl ether, dimethyl ether and dichlorodiethyl ether.

In some specific embodiments, the solvent is an alkane which is liquid at room temperature, such as decane, heptane, dodecane and cyclohexane.

In some specific embodiments, the solvent is an aromatic cyclic compound which is liquid at room temperature, such as toluene and xylene.

In some specific embodiments, the solvent is an aldehyde which is liquid at room temperature, such as benzaldehyde and acetaldehyde, and mixtures thereof.

In some specific embodiments, the solvent is hydroxypropyl methacrylate (HPMA), hydroxyethyl methacrylate (HEMA), EMA, THFMA, pyromellitic dianhydride di(meth)acrylate, pyromellitic dianhydride glyceryl dimethacrylate, pyromellitic dimethacrylate, methacroyloxyethyl maleate, 2-hydroxyethyl methacrylate/succinate, 1,3-glycerol dimethacrylate/succinate adduct, phthalic acid monoethyl methacrylate, and mixtures thereof.

High-Molecular Weight (Meth)Acrylate Polymer or Copolymer

According to some embodiments, the nail coatings of the present embodiments may also include a high-molecular weight (meth)acrylate polymer or copolymer. While the compositions of the present embodiments can include acrylates, methacrylates are preferred because methacrylates are less likely to cause skin sensitization than acrylate formulas. The term '(meth)acrylate' as used herein, means methacrylate, acrylate, or mixtures thereof.

In some specific embodiments, the high-molecular weight (meth)acrylate polymer or copolymer is a copolymer of an alkyl methacrylate (AMA) and methacrylic acid (MAA). The alkyl group may be, for example, methyl, ethyl, propyl or butyl.

According to an aspect, the monomers are present in the polymer in a ratio of about 90 parts AMA to about 10 parts MAA (90:10 AMA/MAA).

According to an aspect, the MAA monomer fraction may vary from 0 to 100%, i.e. the (meth)acrylate polymer or copolymer may be an alkyl methacrylate polymer. According to an aspect, the AMA-MAA copolymer has a AMA:MAA monomer ratio of about 50:50.

According to an aspect, the AMA-MAA copolymer has a AMA:MAA monomer ratio of about 60:40.

According to an aspect, the AMA-MAA copolymer has a AMA:MAA monomer ratio of about 80:20.

According to an aspect, the AMA-MAA copolymer has a AMA:MAA monomer ratio of about 90:10.

According to an aspect, the AMA-MAA copolymer has a AMA:MAA monomer ratio of about 95:5.

In some specific embodiments, the high-molecular weight (meth)acrylate polymer or copolymer is a copolymer of methyl methacrylate (MMA) and methacrylic acid (MAA).

According to an aspect, the monomers are present in the polymer in a ratio of about 90 parts MMA to about 10 parts MAA (90:10 MMA:MAA).

According to an aspect, the MAA monomer fraction may vary from 0 to 100%; i.e. the (meth)acrylate polymer or copolymer may be a methyl methacrylate polymer.

According to an aspect, the MMA-MAA copolymer has a MMA:MAA monomer ratio of about 50:50.

According to an aspect, the MMA-MAA copolymer has a MMA:MAA monomer ratio of about 60:40.

According to an aspect, the MMA-MAA copolymer has a MMA:MAA monomer ratio of about 80:20.

According to an aspect, the MMA-MAA copolymer has a MMA:MAA monomer ratio of about 90:10.

According to an aspect, the MMA-MAA copolymer has a MMA:MAA monomer ratio of about 95:5.

In some specific embodiments, the high-molecular weight (meth)acrylate copolymer is a copolymer of butyl methacrylate (BMA) and methacrylic acid (MAA).

According to an aspect, the monomers are present in the polymer in a ratio of about 90 parts BMA to 10 parts MAA (90:10 BMA/:MAA).

According to an aspect, the MAA monomer fraction may vary from 0 to 100% i.e. the (meth)acrylate polymer or copolymer may be a butyl methacrylate polymer.

According to an aspect, the BMA-MAA copolymer has a BMA:MAA monomer ratio of about 50:50.

According to an aspect, the BMA-MAA copolymer has a BMA:MAA monomer ratio of about 60:40.

According to an aspect, the BMA-MAA copolymer has a BMA:MAA monomer ratio of about 80:20.

According to an aspect, the BMA-MAA copolymer has a BMA:MAA monomer ratio of about 90:10.

According to an aspect, the BMA-MAA copolymer has a BMA:MAA monomer ratio of about 95:5.

In some specific embodiments, the high-molecular weight (meth)acrylate polymer or copolymer has a molecular weight between about 1,000 g/mol and about 20,000 g/mol.

In some specific embodiments, the high-molecular weight (meth)acrylate polymer or copolymer has a molecular weight of at least about 2,000 g/mol.

In some embodiments, the high-molecular weight (meth)acrylate polymer or copolymer has a molecular weight of at least 3,000 g/mol.

In some embodiments, the high-molecular weight (meth)acrylate polymer or copolymer has a molecular weight between about 2,000 g/mol and about 10,000 g/mol.

In some embodiments, the high-molecular weight (meth)acrylate polymer or copolymer has a molecular weight between about 3,000 g/mol and about 10,000 g/mol.

Urethane (Meth)Acrylate Resin

According to some embodiments, the nail coatings of the present embodiments may also include a urethane (meth)acrylate resin. While the compositions of the present embodiments can include urethane acrylates, urethane methacrylates, urethane methacrylates are preferred because urethane methacrylates are less likely to cause skin sensitization than acrylate formulas. The term 'urethane (meth)acrylate' as used herein, means urethane methacrylate, urethane acrylate, or mixtures thereof.

Certain embodiments of the polymerizable liquid composition of the present disclosure may comprise a urethane (meth)acrylate resin which may convey flexibility and toughness to the polymerized product. In certain specific embodiments, urethane methacrylates are preferred.

In some embodiments, the urethane (meth)acrylate monomer may be present from about 0 to about 80 wt %.

In certain specific embodiments, the urethane (meth)acrylate has a molecular weight (grams/mole) of from about 100 to about 20,000.

In certain embodiments, the urethane (meth)acrylate may have a molecular weight of from about 300 to about 15,000.

In certain embodiments, the urethane (meth)acrylate may have a molecular weight of from about 500 to about 13,000.

In certain embodiments, the urethane (meth)acrylate may have a molecular weight of from about 500 to about 6,000.

In some specific embodiments, the urethane (meth)acrylates have a molecular weight between about 200 g/mol and about 20,000 g/mol.

In some embodiments, the urethane (meth)acrylates have a molecular weight of at least about 2,000 g/mol.

In some embodiments, urethane (meth)acrylates have a molecular weight of at least about 3,000 g/mol.

In some embodiments, the urethane (meth)acrylates have a molecular weight between about 2,000 g/mol and about 10,000 g/mol.

In some embodiments, the urethane (meth)acrylates have a molecular weight between about 3,000 g/mol and about 10,000 g/mol.

In some specific embodiments, the urethane (meth)acrylate is an aliphatic polyol modified urethane methacrylate. Such molecules may be formed by reaction of reactants comprising an aliphatic polyol, a hydroxyalkyl methacrylate, and a diisocyanate, and having a weight average molecular weight (MW) ranging from, for example, about 1,000 to about 6,000. Methods for making polyol modified urethane methacrylate without the use of diisocyanate are also known.

In some specific embodiments, the aliphatic polyol is a polyether, polyester, polybutadiene, and/or polycarbonate. For example, the urethane (meth)acrylate is a an aliphatic polyesterpolyol based urethane methacrylate. Such molecules may be formed by reaction of reactants comprising an aliphatic polyesterpolyol, a hydroxyalkyl methacrylate, and a diisocyanate, and having a weight average molecular weight ranging from, for example, about 1,000 to about 6,000.

In some specific embodiments, the hydroxyalkyl methacrylate is selected from the group consisting of hydroxymethyl methacrylate, hydroxyethyl methacrylate, hydroxypropyl methacrylate, hydroxybutyl methacrylate, hydroxypentyl methacrylate, hydroxyhexyl methacrylate, and combinations thereof, and more preferably, the hydroxyalkyl methacrylate is hydroxyethyl methacrylate.

In other specific embodiments, the diisocyanate is selected from the group consisting of isophorone diisocyanate (IPDI), dicyclohexylmethane diiocyanatediisocyanate, 1-methylcyclohexane-2,4-diisocyanate, dicyclohexyl dimethyl-methane-p,p'-diisocyanate, and combinations thereof. More preferably, the diisocyanate is isophorone diisocyanate.

In some specific embodiments, the urethane (meth)acrylate is a polyester, polyether, polybutadiene and/or polycarbonate urethane oligomer (meth)acrylate.

In some specific embodiments, the urethane (meth)acrylate is a polyether urethane oligomer (meth)acrylate. By polyether urethane oligomer (meth)acrylate is meant a compound for example which contains at least polyether, urethane and (meth)acrylate groupings.

In some specific embodiments, the urethane (meth)acrylate is a polyester urethane oligomer (meth)acrylate. By polyester urethane oligomer (meth)acrylate is meant a compound, for example, which contains at least polyester, urethane and (meth)acrylate groups.

In some specific embodiments, the urethane (meth)acrylate is a polybutadiene urethane oligomer (meth)acrylate. By polybutadiene, urethane oligomer (meth)acrylate is meant a compound, for example, which contains at least polybutadiene, urethane and (meth)acrylate groups.

In some specific embodiments, the urethane (meth)acrylate is a polycarbonate urethane oligomer (meth)acrylate. By polycarbonate, urethane oligomer (meth)acrylate is meant a compound, for example, which contains at least polycarbonate, urethane and (meth)acrylate groups.

These urethane oligomer (meth)acrylates are accessible, in that a polyester, polyether, polybutadiene and/or polycarbonate diol (diol component) with an aliphatic, cycloaliphatic and/or aromatic diisocyanate, for example 1,6-hexamethylene diisocyanate (HDI), 2,4,4-trimethylhexamethylene-1,6-diisocyanate (TMDI), tetramethylene diisocyanate, isophorone diisocyanate, 4,4'-dicyclohexylmethane diisocyanate, 1,4-phenylene diisocyanate, 2,6- and 2,4-toluene diisocyanate, 1,5-naphthylene diisocyanate, 2,4'- and 4,4'-diphenylmethane diisocyanate (diisocyanate component) are reacted under amine or tin catalysis.

If a molar excess of diol component compared with diisocyanate component is hereby used, terminal OH groups remain which can be esterified with an ethylenically unsaturated acid such as acrylic acid or methacrylic acid or one of their derivatives.

If a molar excess of diisocyanate component compared with diol component is used, terminal isocyanate groups remain which are reacted with a hydroxyalkyl and/or hydroxyaryl (meth)acrylate and/or di(meth)acrylate and/or tri(meth)acrylate, such as for example 2-hydroxyethyl acrylate (HEA), 2-hydroxyethyl methacrylate (HEMA), 3-hydroxypropyl methacrylate (HPMA), 3-hydroxypropyl acrylate (HPA), glycerol dimethacrylate and/or glycerol diacrylate.

Usable polycarbonate polyols are, for example, products which result from reaction with diols, such as 1,3-propanediol, 1,4-butanediol, 1,6-hexanediol, diethylene glycol, neopentyl glycol, trimethyl-1,6-hexanediol, 3-methyl-1,5-pentanediol and/or tetraethylene glycol, with diaryl carbonates such as diphenyl carbonate, or with phosgene.

Usable polyether polyols include for example products which are accessible by polymerization of a cyclic oxide, for example ethylene oxide, propylene oxide or tetrahydrofuran or by addition of one or more of these oxides to polyfunctional initiators such as water, ethylene glycol, propylene glycol, diethylene glycol, cyclohexane dimethanol, glycerol, trimethylol propane, pentaerythrite or Bisphenol A. Particularly suitable polyether polyols are polyoxypropylene diols and triols, poly(oxyethylene-oxypropylene) diols and triols which are obtained by simultaneous or sequential addition of ethylene oxide and propylene oxide to suitable initiators, as well as polytetramethylene ether glycols, which result from polymerization of tetrahydrofuran.

In some specific embodiments, polyethers include polyethylene oxide, polypropylene oxide, polybutylene oxide.

In some specific embodiments, polyesters include polypropylene glycol, polyethylene glycol, polytetramethylene glycol, ethylene oxide-propylene oxide copolymer, tetrahydrofuran-ethylene oxide copolymer, tetrahydrofuran-propylene oxide copolymer, terephthalic acid, isophthalic acid, naphthalenedicarboxylic acid, cyclohexanedicarboxylic, 1,2-propane diol (propylene glycol), dipropylene glycol, diethylene glycol, 1,3-butanediol, ethylene glycol, and glycerol.

Ethylenically Unsaturated Monomer

The ethylenically unsaturated monomer is, for example, methyl(meth)acrylate, ethyl(meth)acrylate, n-propyl(meth)acrylate, isopropyl(meth)acrylate, n-butyl(meth)acrylate, isobutyl(meth)acrylate, t-butyl(meth)acrylate, 2-ethylhexyl (meth)acrylate, cyclohexyl(meth)acrylate, stearyl(meth)acrylate, lauryl(meth)acrylate, trimethylcyclohexyl(meth)acrylate, isobornyl(meth)acrylate, or other alkyl(meth)acrylates; phenyl(meth)acrylate, benzyl(meth)acrylate, phenoxyethyl(meth)acrylate, phenoxydiethylene glycol (meth)acrylate, or other aromatic (meth)acrylates; tetrahydrofurfuryl(meth)acrylate, oxetane (meth)acrylate, or other heterocyclic (meth)acrylates; methoxy polypropylene glycol (meth)acrylate, ethoxy polypropylene glycol (meth)acrylate, or other alkoxy polyalkylene glycol (meth)acrylates; (meth)acrylamide, N,N-dimethyl(meth)acrylamide, N,N-diethyl (meth)acrylamide, N-isopropyl (meth)acrylamide, diacetone (meth)acrylamide, acryloylmorpholine, or other N-substituted (meth)acrylamides; N,N-dimethylaminoethyl(meth)acrylate, N,N-diethylaminoethyl(meth)acrylate, or other carboxyl group containing (meth)acrylates; or (meth)acrylonitrile, or other nitriles.

Polymers for Enhanced Adhesiveness and Solvent Sensitivity to the Polymerized Lattice Certain embodiments of the liquid composition comprise at least one polymer which is incorporated within the 3-D lattice and which conveys enhanced adhesiveness and which confers solvent sensitivity to the polymerized lattice. The presence of certain polymers at the polymer/nail interface renders the interfacial bonds susceptible to rupture by organic solvents.

According to an aspect, a polymer which conveys both enhanced adhesion and which sensitizes the polymer/nail interface to solvent is a co-polymer of polymethyl methacrylate (PMMA) and polymethacrylic acid (PMAA).

According to an aspect, the monomers are present in the polymer in a ratio of 90 parts PMMA to 10 parts PMAA (90:10 PMMA:PMAA).

According to an aspect, the PMAA monomer fraction may vary from 0 to 100%.

According to an aspect, the PMMA-PMAA copolymer has a PMMA:PMAA monomer ratio of about 50:50.

According to an aspect, the PMMA-PMAA copolymer has a PMMA:PMAA monomer ratio of about 60:40.

According to an aspect, the PMMA-PMAA copolymer has a PMMA:PMAA monomer ratio of about 80:20.

According to an aspect, the PMMA-PMAA copolymer has a PMMA:PMAA monomer ratio of about 90:10.

According to an aspect, the PMMA-PMAA copolymer has a PMMA:PMAA monomer ratio of about 95:5.

Certain embodiments of the liquid composition comprise at least one monomer which imparts to the interfacial bonds a high degree of sensitivity to organic solvent. According to an aspect, the at least one monomer may be polypropylene glycol-4-monomethacrylate (PPG-4 monomethacrylate) or polypropylene glycol-5-monomethacrylate (PPG-5 monomethacrylate). According to an aspect, suitable monomers may include any acrylated or methacrylated monomer in the polyethylene glycol (PEG), polypropylene glycol (PPG), or polybutylene glycol (PBG) families. According to an aspect, such monomers are present at from about 0 to about 70 weight % (wt %).

In certain embodiments, the monomer that imparts to the interfacial bonds a high degree of sensitivity to organic solvent may be a polyol modified urethane (meth)acrylate.

In certain embodiments, the removable, adhesion-promoting nail coating composition further comprises monomers and oligomers chosen such that various bonds within the resulting thermoset are provided an increased sensitivity to solvent. In certain embodiments, such monomers and oligomers are selected from the group consisting of propoxylated allyl methacrylate, methoxy polyethylene glycol (350) monomethacrylate, polyethylene glycol (600) monomethacrylate, stearyl methacrylate, tridecyl methacrylate, hydroxyethyl methacrylate acetate, and mixtures thereof.

(Meth)Acrylate Monomers for Improved Adhesion, Viscosity, Wear and Durability

An embodiment of the present disclosure provides a polymerizable liquid composition comprised of a (meth)acrylate monomer which provides improved adhesion, viscosity, wear and durability.

In certain embodiments, the (meth)acrylate monomer is a tetrahydrofurfuryl methacrylate. In other embodiments, some or all of the tetrahydrofurfuryl methacrylate may be substituted by such monomers including, but not limited to methyl or ethyl methacrylate, hydroxypropyl or hydroxybutyl methacrylate, and/or other monomers such as pyromellitic dianhydride glyceryl dimethacrylate, and similar (meth)acrylate monomers. The aromatic or aliphatic (meth)acrylate monomer may be present from about 0 to about 70 wt %.

Aromatic or Aliphatic (Meth)Acrylate Monomers for Improve Adhesion

Certain embodiments of the present disclosure may comprise other aromatic or aliphatic (meth)acrylate monomers which may be present to improve adhesion. The (meth)acrylate monomer may be a pyromellitic dianhydride glyceryl dimethacrylate (PMGDM).

In general, this (meth)acrylate monomer may be an acid-functional, (meth)acrylate monomer. The acid-functional, (meth)acrylate monomer may be a carboxylic acid polymer. This methacrylate monomer may be present from about 0 to about 70 wt %.

Free Hydroxyl Groups

The inventive composition comprises monomers and oligomers having a plurality of free hydroxyl groups. The hydroxyl groups of the inventive composition may be available to form hydrogen bonds with a substrate which may be a keratinous nail surface.

The hydroxyl groups of the inventive composition may be available to form hydrogen bonds with a substrate which may be a surface of a natural nail or artificial nail enhancement coating.

Adhesion Promoter (Other than POSS)

Certain embodiments of the nail coating composition may comprise an adhesion promoter in addition to POSS. The additional adhesion promoter can be selected from the group consisting of hydroxypropyl methacrylate (HPMA), hydroxyethyl methacrylate (HEMA), ethyl methacrylate (EMA), tetrahydrofurfuryl methacrylate (THFMA), pyromellitic dianhydride di(meth)acrylate, pyromellitic dianhydride glyceryl dimethacrylate, pyromellitic dimethacrylate, methacroyloxyethyl maleate, 2-hydroxyethyl methacrylate/succinate, 1,3-glycerol dimethacrylate/succinate adduct, phthalic acid monoethyl methacrylate, methacroyloxyethyl maleate, 2-hydroxyethyl methacrylate/succinate, 1,3-glycerol dimethacrylate/succinate adduct, butyl methacrylate, isobutyl methacrylate, PEG-4 dimethacrylate, PPG monomethacrylate, trimethylolpropane trimethacrylate, isopropylidenediphenyl bisglycidyl methacrylate, lauryl methacrylate, cyclohexyl methacrylate, hexyl methacrylate, urethane methacrylate, triethylene glycol dimethacrylate, ethylene glycol dimethacrylate, tetraethylene glycol dimethacrylate, trimethylolpropane trimethacrylate, neopentylglycol dimethacylate, acetoacetoxy methacrylate, acetoacetoxyethyl methacrylate (AAEMA), polyetheramine, glycidyl methacrylates, maleic anhydride, terpolymers containing vinyl acetate, organosilanes, organotitanates, chlorinated polyolefins, sucrose acetate isobutyrate, caprylic/capric triglyceride, glyceryl hydrogenated rosinate, pentaerythryl hydrogenated rosinate, styrene/methyl styrene/indene copolymer, blocked isocyanate PVC, polyamidoamine PVC, and mixtures thereof.

Optional Resin(s)

Certain embodiments of the formulation may optionally comprise resins, such as, but not limited to polyvinylbutyral and/or tosylamide formaldehyde resins. Such resins may act as film formers, adhesion promoters, and aids to removal. These resins may also qualify as solvent-dissolvable resins which are dispersed in the polymerized structure and can be easily dissolved by a solvent to facilitate solvent absorption and migration during removal.

UV Stabilizing Agent

According to certain embodiments, the formulations may further comprise at least one UV stabilizing agent. In certain embodiments, the UV stabilizer is present at up to 2 wt %.

The compositions of the invention may contain one or more UV absorbers, which assist in reducing the yellowing which is often seen in artificial nails. UV absorbers have the ability to convert incident UV radiation into less damaging infrared radiation (heat), or visible light. A recommended amount of UV absorber is 0.001-5% by weight of the total composition. Suitable UV absorbers include hydroxy benzotriazole compounds and benzophenone compounds such as are disclosed in U.S. Pat. No. 6,818,207, incorporated by reference.

The removable, adhesion-promoting nail coating composition may comprise up to 5 wt % of a UV-absorber selected from the group consisting of hydroxy benzotriazole compounds such as 2-(2-hydroxy-5'-methylphenyl)benzotriazole, benzophenones 1-12,3-benzylidene camphor, benzyl salicylate, borneolone, borneol, camphor, bumetrizole, PABA, butyl PABA, butyl methoxydibenzoylmethane, cinoxate, DEA-methoxycinnamate, dibenzoxazoyl naphthalene, digalloyl trioleate, diisopropyl methyl cinnamate, 2-(2H-benzotriazol-2-yl-4-methyl)-phenol (available from BASF Corporation (Florham Park, N.J.) as TinuvinP®) and mixtures thereof.

Photoinitiators and Polymerization

Both UV and visible light activated photoinitiators may be suitable for the present invention. Suitable photoinitiator systems include, but are not limited to, aromatic alpha hydroxy ketones, alkoxyoxybenzoins, acetophenones, acylphosphine oxides, bisacylphosphine oxides, and a tertiary amine plus a diketone, mixtures thereof and the like.

Illustrative examples of photoinitiators are 1-hydroxycyclohexyl phenyl ketone, 2-hydroxy-2-methyl-1-phenyl propan-1-one, bis(2,6-dimethoxybenzoyl) 2,4,4-trimethylpentyl phosphine oxide (DMBAPO), bis(2,4,6-trimethylbenzoyl) phenyl phosphineoxide (Irgacure 819), 2,4,6-trimethylbenzyldiphenyl phosphine oxide, and 2,4,6-trimethylbenzoyl diphenylphosphine oxide, benzoin methyl ester, camphorquinone, and a combination of camphorquinone and ethyl 4 (N,N dimethylamino)benzoate.

Commercially available visible light initiator systems include bis(2,4,6-trimethylbenzoyl) phenyl phosphine oxide (IRGACURE® 8191, mono- and bis-acylphosphine photoinitiators (such IRGACURE® 1700, IRGACURE® 1800, and IRGACURE® 1850 (all from Ciba Specialty Chemicals) and 2,4,6-trimethylbenzoybiphenylphosphine oxide (manufactured by BASF under the trade name LUCIRIN® TPO initiator (available from BASF). Commercially available UV photoinitiators include α-hydroxyketone photoinitators (including α-hydroxyketone photoinitators sold under the trade name DAROCUR 1173 and IRGACURE® 2959 (Ciba Specialty Chemicals). The initiator is used in the reaction mixture in effective amounts to initiate photopolymerization of the reaction mixture, e.g., from about 0.01 to about 5 parts per 100 molar parts of reactive monomer. Alternatively, initiation can be conducted without a photoinitiator using, for example, e beam. Preferred initiators include bisacylphosphine oxides, such as bis(2,4,6-trimethylbenzoyl) phenyl phosphine oxide (IRGACURE® 819®) or a combination of 1-hydroxycyclohexylphenyl ketone and bis(2,6-dimethoxybenzoyl)-2,4,4-trimethylpentyl phosphine oxide (DMBAPO), and the preferred method of polymerization initiation is visible light.

In some specific embodiments, visible light activated photoinitiators are preferred. The most preferred is bis(2,4,6-trimethylbenzoyl) phenyl phosphine oxide (Irgacure 819®).

Viscosity of the coating may be controlled with the addition or removal of solvent.

According to some embodiments, there is provided a method of applying a nail coating to an uncoated nail including the step of applying a nail coating according to any of the present embodiments. As used herein, the term "uncoated nail" may be a natural nail or an artificial nail. In some embodiments, a nail topcoat may be further applied to the coated nail surface, wherein the nail is coated with a nail coating according to the present embodiments. The method can also include the step of providing an uncoated nail. In some embodiments, the topcoat is a topcoat according to any of the embodiments described herein.

According to some embodiments, there is provided a method of applying a coating to a natural nail that includes the step of applying a nail coating according to any of the present embodiments to a natural nail. In some embodiments, a nail topcoat may be further applied to the coated nail surface, wherein the nail is coated with a nail coating according to the present embodiments. The method can also include the step of providing a natural nail.

In some embodiments, the natural nail is not surface treated with a primer. In some embodiments, the natural nail is not surface treated with a file. In some embodiments, the natural nail is not roughened or otherwise texturized in order to promote the adhesion of a nail coating.

Methods of preparing polymer compositions by compounding nanostructured POSS chemicals into polymers are disclosed in U.S. Pat. No. 6,716,919, incorporated herein by reference in its entirety.

Methods of dispersing particulates into a polymer by controlling its surface properties at the nanoscopic level with the use of nanostructured POSS chemicals are disclosed in U.S. Pat. No. 7,723,415, incorporated herein by reference in its entirety.

Certain embodiments of the disclosed polymerizable composition may be viscous gels or liquids. Gel or liquid embodiments may be polymerized by exposure to radiant energy, such as heat, visible, UV, or electron-beam radiation. Liquid or gel embodiments are applied upon nails and may be shaped to the desired configuration. The coated nails are exposed to a polymerization initiator, for example radiant energy or a chemical polymerization initiator such as a peroxide is included or mixed into the formulation, and polymerization occurs.

The inventive composition may be polymerizable with actinic radiation. The actinic radiation may be visible, ultraviolet (UV), or electron beam radiation. The UV radiation may be characterized by a wavelength, or group of wavelengths, typically, but not limited to about 320 to about 420 nanometers.

After the liquid composition is applied to a nail surface, the liquid is polymerized or cured. The liquid composition comprises ethylenically unsaturated (meth)acrylates which may be polymerized or cured by a UV-initiated, free-radical polymerization method. Persons of skill in the polymerization arts may readily determine suitable photoinitiators for use with the invention. Suitable photoinitiators include, but are not limited to benzoyl-diphenylsphosphinates, phenyl ketones, and dimethyl ketals. Set forth below are non-limiting representative photoinitiators that are suitable for purposes of the invention.

A non-limiting suitable photoinitiator is a 2,4,6-trimethylbenzoyl diphenylphosphorous derivative. A suitable derivative is ethyl-2,4,6-trimethyl benzoyldiphenylphosphinate, which may be obtained under the trade name LUCIRIN® TPO-L (BASF Aktiengesellschaft, Ludwigshafen, DE). Another non-limiting suitable derivative is 2,4,6-trimethylbenzoyldiphenylphosphine oxide, which may be obtained under the trade name LUCIRIN® TPO (BASF) or as GENOCURE® TPO (Rahn). The 2,4,6-trimethyl-benzoyldiphenylphosphinate photoinitiator may be present from about 0% to about 20 wt %.

A non-limiting suitable photoinitiator is hydroxycyclohexyl phenyl ketone, which may be obtained under the trade name IRGACURE® 184 and which may be present from about 0 to about 20 wt %.

A non-limiting suitable photoinitiator is hydroxycyclohexyl phenyl ketone, which may be obtained under the trade name Irgacure® 184 and which may be present from about 0 to about 20 wt %.

A non-limiting suitable photoinitiator is benzil dimethyl ketal (BDK), which may be obtained under the trade name FIRSTCURE® BDK (Albemarle, Baton Rouge, La., US) and which may be present from about 0 to about 20 wt %.

Polymerization Regulators

It may be desirable to include one or more polymerization regulators. A polymerization regulator assists in preventing the polymerization of the monomer composition from occurring too quickly.

Hydroquinone and similar materials are suitable polymerization regulators. Suggested ranges of polymerization regulators are from about 0.0001-5% by weight of the total composition. Suitable polymerization regulators are disclosed in U.S. Pat. No. 6,818,207, incorporated by reference.

Color Layer/Color Agents

An aspect of the disclosure provides a color layer. Certain embodiments of a color layer may comprise up to 10 wt % pigments and/or dyes. Embodiments of the basecoat and topcoat may have up to 1 wt % pigments and/or dyes.

High concentrations of pigments and/or dyes may absorb UV radiation. To compensate therefore, certain embodiments of the present disclosure may comprise higher concentrations, up to 20 wt %. photoinitiator.

Solvents

A conventional thermoset nail coating comprises 100% solids and does not comprise non-reactive solvents. The polymerizable liquid composition of the present disclosure further comprises at least one non-reactive solvent. A suitable non-reactive solvent is readily volatile at room temperature and is a good solvent for the remaining ingredients. Upon application, the non-reactive solvent readily volatilizes leaving regions of increased porosity throughout the nail coating. These porous regions later facilitate the entry of a remover solvent which may be acetone.

Suitable non-reactive solvents may be selected from the group consisting of ketones, alkyl acetates, alcohols, alkanes, alkenes, and mixtures thereof. Suitable solvents may be selected from the group consisting of acetone, ethyl acetate, butyl acetate, isopropyl alcohol, ethanol, methyl ethyl ketone, toluene, hexane, and mixtures thereof. A particularly suitable solvent is acetone. Typically a solvent or a mixture of solvents is included at up to about 70 weight percent.

EXAMPLES

It is understood that modifications which do not substantially affect the activity of the various embodiments of this invention are also provided within the definition of the invention provided herein. Accordingly, the following examples are intended to illustrate but not limit the present invention. While the claimed invention has been described in detail and with reference to specific embodiments thereof, it will be apparent to one of ordinary skill in the art in view of the present description that various changes and modifications can be made to the claimed invention without departing from the spirit and scope thereof.

Thus, for example, those skilled in the art will recognize, or be able to ascertain, using no more than routine experimentation, numerous equivalents to the specific substances and procedures described herein. Such equivalents are considered to be within the scope of this invention, and are covered by the following claims.

The Examples below refer to POSS compounds according to their catalog number or Tradename as available from Hybrid Plastics or Mayamaterials as referred to elsewhere in the specification, above. In summary, the following POSS materials are used:

EP0409: $(C_6H_{11}O_2)_n(SiO_{1.5})_n$, where n is 8, 10, or 12 (Glycidyl POSS® Cage Mixture)

AM0281: Hydrolyzed [3-(Trimethoxysilyl)propyl]aniline (N-Phenylaminopropyl POSS™ Cage Mixture)

NB1038: [(Dimethyl(norbornenylethyl)silyloxy)dihydroxy]-POSS®

PM1285MV: (Vinyl Silsesquioxane Resin)-liquid

Example 1

Color Containing Base Formula

The base formula used to prepare exemplary color containing coatings according to the present embodiments is as follows:

| Component | Wt. % |
|---|---|
| Butyl Acetate | 43.361 |
| Ethyl Acetate | 28.582 |
| Nitrocellulose | 11.512 |
| Adipic Acid/Neopentyl Glycol/Trimellitic Anhydride Copolymer | 5.929 |
| Acetyl Tributyl Citrate | 4.941 |
| Isopropyl alcohol | 2.393 |
| Stealkonium bentonite | 1.207 |
| Red 7 Lake CI5850 | 0.506 |
| Red 6 Lake CI5850 | 0.488 |
| Alkyl Acrylate copolymer | 0.302 |
| Silica | 0.201 |
| TiO2 C177891 | 0.182 |
| D&C black 2 | 0.001 |
| Propylene carbonate | 0.198 |
| Benzophenone 1 | 0.198 |

Example 2

Two exemplary base formulas used to prepare exemplary clear coatings according to the present embodiments are as follows:

| | Wt. % | |
|---|---|---|
| Component | Clear Base Formula A | Clear Base Formula B |
| Ethyl Acetate | 50.340 | 40.1000 |
| Butyl Acetate | 15.592 | 24.2499 |
| Phthalic Anhydride/Trimellitic Anhydride/Glycols Copolymer | 11.508 | |
| Adipic Acid/Neopentyl Glycol/Trimellitic Copolymer | | 7.2000 |
| Nitrocellulose | 11.389 | 13.0000 |
| Cellulose Acetate Butyrate | | |
| Acetyl Tributyl Citrate | 6.290 | 5.6000 |
| IPA | 4.881 | 5.6000 |
| Acrylates Copolymer | | |
| Heptane | | 4.0000 |
| Violet 2 C160725 | 0.001 | 0.0001 |
| Benzophenone | | 0.2000 |
| Trimethylpentanediyl dibenzoate | | 0.0500 |

Exemplary clear nail coatings according to the above formulations, plus added POSS, were prepared, tested and compared to control samples (without added POSS). Control samples correspond to a commercially available clear nail enamel.

| Formula # | EP0409 | Acetyl Tributyl Citrate | Clear Base Formula A | Clear Base Formula B |
|---|---|---|---|---|
| 1 | 2 | 2 | | 96 |
| 1 Control | 0 | 0 | | 100 |
| 2 | 2 | 2 | 96 | |
| 2 Control | 0 | 0 | 100 | |

The above compositions were tested for adhesion using the Cross Hatch Adhesion test (ASTM D3359). Briefly, a crosshatch pattern is made through the film to the substrate. Detached flakes of coating are removed by brushing with a soft brush. Pressure-sensitive tape is applied over the crosshatch cut. Tape is smoothed into place by using a pencil eraser over the area of the incisions. Tape is removed by pulling it off rapidly over itself as close to an angle of 180°. Adhesion is assessed on a 0 to 5 scale. The table below summarizes the results from testing.

| FORMULA # | AVERAGE ADHESION SCORE | Improvement over Control |
|---|---|---|
| 1 | 3.0 | 71% |
| 1 Control | 1.75 | — |
| 2 | 2.25 | 125 |
| 2 Control | 1.0 | — |

Adhesion was measured for this formulation, and for the same formulation with varying amounts of POSS EP0409 added.

| POSS | Avg. Adhesion Score |
|---|---|
| 0 wt % | 3.17 |
| 2 wt % EP0409 | 3.67 |
| 4.67 wt % EP0409 | 4.25 |
| 10 wt % EP0409 | 4.50 |

Example 3

Nail Coatings and Testing

Exemplary color containing nail coatings according to the present embodiments were prepared and tested. Twenty five different formulas were prepared using the ranges set forth in the table below:

| Component | Minimum | Maximum |
|---|---|---|
| EP0409 | 0.00% | 3.00% |
| Acetyl Tributyl Citrate | 0.00% | 2.50% |
| Ethyl Acetate* | 0.00% | 10.00% |
| Butyl Acetate* | 0.00% | 10.00% |
| Color Containing Base Formula | 84.50% | 100.00% |

*Solvent constraint: The combination of Ethyl Acetate and Butyl Acetate ≤ 10%

One or more of the components of Ethyl Acetate, Butyl Acetate, Acetyl Tributyl Citrate, and EP0409 were added to the Color Containing Base Formula to prepare the test coatings of Formulas #1 to 25, provided in the table below. The amounts are provided in weight percent.

| Formula # | EP0409 (%) | Acetyl Tributyl Citrate (%) | Ethyl Acetate (%) | Butyl Acetate (%) | Color Containing Base Formula (%) |
|---|---|---|---|---|---|
| 1 | 3 | 0 | 10 | 0 | 87 |
| 2 | 2 | 1.25 | 4.5 | 1.5 | 90.75 |
| 3 | 1 | 2.5 | 6 | 0 | 90.5 |
| 4 | 1 | 0 | 10 | 0 | 89 |
| 5 | 3 | 2.5 | 5 | 5 | 84.5 |
| 6 | 3 | 1.25 | 0 | 10 | 85.75 |
| 7 | 1 | 2.5 | 0 | 10 | 86.5 |
| 8 | 3 | 2.5 | 10 | 0 | 84.5 |
| 9 | 3 | 2.5 | 2 | 0 | 92.5 |
| 10 | 1 | 0 | 0 | 10 | 89 |
| 11 | 1 | 0 | 10 | 0 | 89 |
| 12 | 1 | 0 | 6 | 0 | 93 |
| 13 | 2 | 1.25 | 1.5 | 4.5 | 90.75 |
| 14 | 2.5 | 1.875 | 6.5 | 1.5 | 87.625 |
| 15 | 3 | 2.5 | 0 | 6 | 88.5 |
| 16 | 1 | 2.5 | 0 | 10 | 86.5 |
| 17 | 3 | 0 | 5 | 5 | 87 |
| 18 | 3 | 1.25 | 0 | 10 | 85.75 |
| 19 | 1 | 0 | 2 | 0 | 97 |
| 20 | 3 | 0 | 0 | 2 | 95 |
| 21 | 2 | 2.5 | 0 | 2 | 93.5 |
| 22 | 1 | 2.5 | 6 | 0 | 90.5 |
| 23 | 1 | 1.25 | 0 | 2 | 95.75 |
| 24 | 1 | 0 | 0 | 6 | 93 |
| 25 | 3 | 0 | 0 | 2 | 95 |
| Control | 0 | 0 | 0 | 0 | 100 |

The compositions of formulas 1-25 were tested for adhesion, dry time and print resistance and compared to a control sample corresponding to a commercially available nail enamel. Dry time is a measure of how much time the composition required for drying.

Adhesion was measured using the Cross Hatch Adhesion test (ASTM D3359). Briefly, a crosshatch pattern is made though the film to the substrate. Detached flakes of coating are removed by brushing with a soft brush. Pressure sensitive tape is applied over the crosshatch cut. Tape is smoothed into place by using a pencil eraser over the area of the incisions. Tape is removed by pulling it off rapidly back over itself as close to an angle of 180°. Adhesion is assessed on a 0 to 5 scale.

Print Resistance is a measure of a resistance of dried lacquer films to imprinting and this was tested using the Standard Test Method for Print Resistance of Lacquers (ASTM D 2091). Briefly, a weight presses a piece of fabric against the test surface. The surface is then examined and changes in appearance of the test surface are reported.

The table below summarizes the test results.

| FORMULA # | ADHESION SCORE | Dry Time (min) | Print Resistance |
|---|---|---|---|
| 21 | 4.21 | 13 | Medium Print |
| 5 | 4.04 | 12 | Medium Print |
| 15 | 4.00 | 14 | Medium Print |
| 6 | 3.96 | 10 | Slight-Medium |
| 7 | 3.88 | 12 | Medium Print |
| 8 | 3.88 | 8 | Medium Print |
| 14 | 3.83 | 13 | Medium Print |
| 3 | 3.58 | 13 | Medium Print |
| 2 | 3.50 | 10 | Slight Print |
| 11 | 3.50 | 10 | Slight Print |
| 16 | 3.50 | 8 | Medium Print |
| 1 | 3.42 | 8 | Medium Print |
| 18 | 3.42 | 15 | Medium Print |
| 17 | 3.33 | 11 | Medium Print |
| 9 | 3.33 | 13 | Medium Print |
| 10 | 3.33 | 12 | Slight Print |
| 13 | 3.33 | 14 | Slight-Medium |
| 20 | 3.25 | 11 | Medium Print |
| 25 | 3.25 | 2 | Medium Print |
| 4 | 3.17 | 10 | Slight Print |
| 22 | 3.17 | 13 | Slight-Medium |
| 19 | 2.83 | 12 | Medium Print |
| 24 | 2.83 | 11 | Slight-Medium |
| 12 | 2.75 | 6 | Slight Print |
| 23 | 2.67 | 11 | Medium Print |
| Control | 1.83 | 16 | Slight Print |

Example 4

Nail Coatings and Testing

In another exemplary embodiment, a basecoat nail coating composition to which POSS can be advantageously be added has the following components:

| Ingredient | Exemplary formula |
|---|---|
| Tetrahydrofurfuryl Methacrylate | 20.04600 |
| PPG-5 Methacrylate | 20.04600 |
| Cellulose Acetate Butyrate | 16.06700 |
| Acetone | 12.50971 |
| Bis-HEMA Poly(1,4-Butanedio-1)-22/IPDI Copolymer | 11.43600 |
| Alcohol Denat. | 4.59821 |
| Acrylates Copolymer | 4.52958 |
| Di-HEMA Trimethylhexyl Dicarbamate | 4.35000 |
| Hydroxycyclohexyl Phenyl Ketone | 2.11020 |
| Butyl Acetate | 1.40680 |
| Ethyl Trimethylbenzoyl Phenylphosphinate | 1.40000 |
| Bis(Glyceryl Dimethacrylate) Pyromellitate | 0.55850 |
| Phenyldimethoxyacetophenone | 0.23550 |
| Hydroxypropyl Methacrylate | 0.70650 |
| | 100.00000 |

Example 5

Adhsision was measured for a basecoat composition including a color agent, HEMA, HPMA, Di-HEMA trimethylhexyl carbamate, and hydroxyclohexyl phenyl keotone, and for the same formulation with a 1:1 mixture of ethyl acetate:POSS added to give 10 wt % POSS in the final formulation:

| POSS | Avg. Adhesion Score |
|---|---|
| 0% | 1.67 |
| 10 wt % EP0409 | 4.17 |
| 10 wt % AM0281 | 4.00 |
| 10 wt % NB1038 | 4.83 |
| 10 wt % PM1285MV | 2.17 |

Example 6

Nail Topcoat Base Formula

The base formula used to prepare exemplary topcoat formulations according to the present embodiments is as follows:

| Component | Wt. % |
|---|---|
| Ethyl Acetate | 40.1 |
| Butyl Acetate | 24.2 |
| Adipic Acid/Neopentyl Glycol/Trimellitic | 7.2 |
| Nitrocellulose or cellulose acetate butyrate | 13.0 |
| Acetyl Tributyl Citmte | 5.6 |
| Isopropyl alcohol | 5.6 |
| Heptane | 4.0 |
| Benzophenone | 0.2 |
| Trimethylpentanediyl dibenzoate | 0.1 |

Example 7

Adhesion was measured for a basecoat formulation including the following components: a color agent, HEMA, HPMA, Isobornyl methacrylate, Di HEMA trimethylhexyl carbamate, Benzophenone, Hydroxycylcohexyl Phenyl Ketone, TPO, Trimethyl Pentaryl Diisobutyrate, Camphor, Dimethicone, Nitrocellulose, Tosylamide/Epoxy Resin, Polyvinyl butyral, Butyl Acetate, Alcohol, and Heptane.

Adhesion was measured for the formulation, and for the same formulation with a 1:1 mixture of ethyl acetate:POSS added to give 10 wt % POSS in the final formulation.

| POSS | Avg. Adhesion Score |
|---|---|
| 0 wt % | 3.83 |
| 10 wt % EP0408 | 3.83 |
| 10 wt % AM0281 | 4.00 |
| 10 wt % NB1038 | 4.00 |

Example 8

Nail Topcoats and Testing

Exemplary topcoat nail coating according to the present embodiments were prepared and tested. Thirty eight different formulas were prepared using the ranges set forth in the table below:

| Component | Minimum | Maximum |
|---|---|---|
| EP0409 | 0.00% | 3.00% |
| Acetyl Tributyl Citrate | 0.00% | 3.00% |
| Isopropylidenediphenol PEG-2 Dimethacrylate | 0.00% | 5.00% |
| Irgacure 819 (10% Solution) | 0.00% | 3.00% |
| Butyl Metacrylate/Methacrylic Acid Copolymer 90/10 (33% in EtOH/Acetone) | 0.00% | 7.50% |
| Butyl Acetate | 0.00% | 7.50% |
| Nail Topcoat base formula | 75.00% | 100.00% |

One or more of the components of Butyl Methacrylate/Methacrylic Acid (BUMA) 90%/10% copolymer (33% in EtOH/Acetate), Urethane Methacrylate, Irgacure 819 (10% Solution), Butyl Acetate, Acetyl Tributyl Citrate, and EP0409 were added to the Topcoate Base Formula, provided above in Example 7, to prepare the test coatings of Formulas #1 to #38, provided in the table below. The amounts are provided in weight percent.

| Formula # | BUMA-MMA copolymer | Urethane Methacrylate | Irgacure 819 10% Sol | Butyl Acetate | Acetyl Tributyl Citrate | EP0409 | Nail Topcoat Base Formula |
|---|---|---|---|---|---|---|---|
| 1 | 0.0 | 5.0 | 0.0 | 3.8 | 3.0 | 3.0 | 85.3 |
| 2 | 0.0 | 0.0 | 3.0 | 0.0 | 0.0 | 3.0 | 94.0 |
| 3 | 7.5 | 0.0 | 3.0 | 0.0 | 0.0 | 0.0 | 89.5 |
| 4 | 7.5 | 5.0 | 2.0 | 7.5 | 3.0 | 0.0 | 75.0 |
| 5 | 7.5 | 0.0 | 0.0 | 0.0 | 0.0 | 3.0 | 89.5 |
| 6 | 0.0 | 0.0 | 0.0 | 7.5 | 0.0 | 3.0 | 89.5 |

-continued

| Formula # | BUMA-MMA copolymer | Urethane Methacrylate | Irgacure 819 10% Sol | Butyl Acetate | Acetyl Tributyl Citrate | EP0409 | Nail Topcoat Base Formula |
|---|---|---|---|---|---|---|---|
| 7 | 3.8 | 5.0 | 0.0 | 7.5 | 0.0 | 3.0 | 80.8 |
| 8 | 3.8 | 5.0 | 3.0 | 0.0 | 3.0 | 3.0 | 82.3 |
| 9 | 0.0 | 5.0 | 3.0 | 0.0 | 0.0 | 0.0 | 92.0 |
| 10 | 0.0 | 5.0 | 0.0 | 7.5 | 0.0 | 0.0 | 87.5 |
| 11 | 7.5 | 2.5 | 3.0 | 0.0 | 0.0 | 3.0 | 84.0 |
| 12 | 7.5 | 5.0 | 3.0 | 7.5 | 0.0 | 2.0 | 75.0 |
| 13 | 0.0 | 0.0 | 3.0 | 7.5 | 0.0 | 0.0 | 89.5 |
| 14 | 7.5 | 2.5 | 0.0 | 7.5 | 0.0 | 0.0 | 82.5 |
| 15 | 7.5 | 5.0 | 3.0 | 7.5 | 2.0 | 0.0 | 75.0 |
| 16 | 0.0 | 5.0 | 3.0 | 7.5 | 3.0 | 3.0 | 78.5 |
| 17 | 7.5 | 5.0 | 0.0 | 6.5 | 3.0 | 3.0 | 75.0 |
| 18 | 0.0 | 0.0 | 0.0 | 7.5 | 3.0 | 1.5 | 88.0 |
| 19 | 7.5 | 0.0 | 3.0 | 7.5 | 3.0 | 3.0 | 76.0 |
| 20 | 0.0 | 0.0 | 0.0 | 0.0 | 3.0 | 3.0 | 94.0 |
| 21 | 7.5 | 5.0 | 1.0 | 7.5 | 1.0 | 3.0 | 75.0 |
| 22 | 0.0 | 5.0 | 0.0 | 0.0 | 0.0 | 3.0 | 92.0 |
| 23 | 7.5 | 5.0 | 3.0 | 3.3 | 0.0 | 3.0 | 78.3 |
| 24 | 0.0 | 5.0 | 3.0 | 0.0 | 0.0 | 0.0 | 92.0 |
| 25 | 7.5 | 5.0 | 3.0 | 7.5 | 2.0 | 0.0 | 75.0 |
| 26 | 3.8 | 0.0 | 0.0 | 7.5 | 3.0 | 0.0 | 85.8 |
| 27 | 0.0 | 0.0 | 0.0 | 0.0 | 0.0 | 0.0 | 100.0 |
| 28 | 7.5 | 0.0 | 0.0 | 0.0 | 3.0 | 0.0 | 89.5 |
| 29 | 7.5 | 5.0 | 2.0 | 7.5 | 3.0 | 0.0 | 75.0 |
| 30 | 0.0 | 0.0 | 3.0 | 0.0 | 3.0 | 0.0 | 94.0 |
| 31 | 0.0 | 5.0 | 0.0 | 0.0 | 3.0 | 0.0 | 92.0 |
| 32 | 7.5 | 5.0 | 0.0 | 3.8 | 3.0 | 0.0 | 80.8 |
| 33 | 4.0 | 1.4 | 1.5 | 4.0 | 1.5 | 1.5 | 85.9 |
| 34 | 7.5 | 0.0 | 3.0 | 7.5 | 3.0 | 3.0 | 76.0 |
| 35 | 7.5 | 5.0 | 0.0 | 0.0 | 0.0 | 0.0 | 87.5 |
| 36 | 0.0 | 2.5 | 3.0 | 0.0 | 3.0 | 3.0 | 88.5 |
| 37 (Control) | 0.0 | 0.0 | 0.0 | 0.0 | 0.0 | 0.0 | 100.0 |
| 38 | 0.0 | 2.5 | 3.0 | 7.5 | 0.0 | 3.0 | 84.0 |

The compositions of Formulas 1-38 were tested for dry time, gloss and print resistance. Dry time is a measure of how much time the composition required for drying. Gloss was tested using a 20 degree gloss meter.

Pencil hardness measurements are used to determine the hardness of the coatings. The hardness of a coating, relative to a standard set of pencil leads, is determined by scratching the leads across the coating at a controlled angle of 45° for a distance of approximately ¼ inch (6.35 mm). The range of the pencil leads is from 6B (softest) 5B 4B 3B 2B B H 2H 3H 4H 5H 6H (hardest). The recorded rating indicates the hardness at which the pencil lead scratches the coating.

The Table below summarizes the results from testing.

| Formula # | Dry Time (min) | Gloss | Pencil Hardness rate |
|---|---|---|---|
| 3 | 6 | 171.3 | B |
| 27 | 7 | 190.4 | B |
| 28 | 7 | 186.6 | B |
| 35 | 7 | 186.4 | B |
| 37 (Control) | 7 | 185.1 | B |
| 10 | 8 | 187.0 | B |
| 12 | 8 | 188.4 | B |
| 14 | 8 | 181.6 | B |
| 19 | 8 | 183.4 | B |
| 24 | 8 | 187.4 | B |
| 33 | 8 | 189.7 | B |
| 5 | 9 | 168.6 | B |
| 11 | 9 | 188.1 | B |
| 25 | 9 | 190.2 | B |
| 26 | 9 | 185.8 | B |
| 29 | 9 | 188.4 | B |
| 32 | 9 | 184.7 | B |
| 34 | 9 | 186.2 | B |
| 2 | 10 | 167.1 | B |
| 20 | 10 | 189.3 | B |
| 21 | 10 | 184.3 | B |
| 23 | 10 | 183.0 | B |
| 30 | 10 | 182.9 | B |
| 9 | 11 | 176.0 | B |
| 13 | 11 | 188.6 | B |
| 15 | 11 | 186.2 | B |
| 38 | 11 | 185.3 | B |
| 4 | 13 | 171.8 | B |
| 6 | 13 | 167.0 | B |
| 18 | 13 | 185.6 | B |
| 22 | 13 | 184.9 | B |
| 31 | 13 | 184.4 | B |
| 7 | 14 | 188.5 | B |
| 17 | 14 | 189.5 | B |
| 1 | 16 | 165.9 | B |
| 8 | 16 | 167.8 | B |
| 16 | 16 | 176.3 | B |
| 36 | 16 | 183.3 | B |

Example 9

Adhesion was measured for the basecoat formulation of Example 8, and for the same formulation with a 1:1 mixture of HEMA:POSS added to give 10 wt % POSS in the final formulation.

| POSS | Avg. Adhesion Score |
|---|---|
| 0% | 3.83 |
| 10 wt % PM1258MV | 4.50 |

Example 10

In one exemplary embodiment, a color layer nail coating composition to which POSS is advantageously added has the following components:

| Ingredient | Exemplary formula | Possible Range |
|---|---|---|
| Butyl Acetate | 24.00000 | >10-30% |
| Bis-HEMA Poly(1,4-Butanediol)-22/IPDI Copolymer | 14.02000 | >10-30% |
| Cellulose Acetate Butyrate | 18.83660 | >10-30% |
| PPG-5 Methacrylate | 12.81000 | >10-30% |
| Tetrahydrofurfuryl Methacrylate | 12.81000 | >10-30% |
| Di-HEMA Trimethylhexyl Dicarbamate | 3.00000 | >3-10% |
| Phenyldimethoxyacetophenone | 0.40000 | >1-3% |
| Hydroxypropyl Methacrylate | 1.42000 | >1-3% |
| Silica | 0.50000 | >.3-1% |
| MAY CONTAIN THESE INGREDIENTS: | | |
| Titanium Dioxide | | >3-10% |
| Mica | | >3-10% |
| Hydroxycyclohexyl Phenyl Ketone | 4.20000 | >3-10% |
| Ethyl Trimethylbenzoyl Phenylphosphinate | | >3-10% |
| Trimethylbenzoyl Diphenylphosphine Oxide | 2.00000 | >1-3% |
| Methyl Pyrrolidone | | >.1-3% |
| Isopropyl Alcohol | | >.3-1% |
| Nitrocellulose | | >.3-1% |
| Tin Oxide | | >.1-.3% |
| Stearalkonium Hectorite | | <.1% |
| Drometrizole | 0.00330 | <.1% |
| MAY CONTAIN THESE COLORANTS: | | |
| CI 15850 (Red 6 Lake) | | >.3-1% |
| CI 15850 (Red 7 Lake) | | >.3-1% |
| CI 15880 (Red 34 Lake) | | >.1-.3% |
| CI 19140 (Yellow 5 Lake) | | >1-3% |
| CI 60730 (Ext. Violet 2) | 0.00010 | <.1% |
| CI 77163 (Bismuth Oxychloride) | | >3-10% |
| CI 77491 (Iron Oxides) | | >1-3% |
| CI 77499 (Iron Oxides) | | >1-3% |
| CI 77891 (Titanium Dioxide) | 6.00000 | >3-10% |

Example 11

Adhesion was measured for a color layer formulation of Example 11, and for the same formulation with 10 wt % of POSS NB1038. The first set of tests (left column) was with 1 coat, 4 min cure, IPA wipe. The second set (right column) was with 2 coats, 4 min cure, IPA wipe.

| POSS Additive | Average Adhesion Score | |
|---|---|---|
| 0% | 1.33 | 0.50 |
| 10 wt % NB1038 | 3.50 | 3.83 |

Example 12

Adhesion was measured for a color layer formulation including the following components: Stearalkonium Hectorite, Color, HEMA, HPMA, Isobornyl methacrylate, Di HEMA trimethylhexyl carbamate, Hydroxycyclohexyl Phenyl Ketone, Citric Acid, Dimethicone (Plasticizer), Phosphoric Acid, Nitrocellulose, Butyl Acetate, Diacetone Alcohol, and Ethyl Acetate, and for the same formulation with a 1:1 mixture of ethyl acetate:POSS added to give 10 wt % POSS in the final formulation.

| POSS | Average Adhesion Score |
|---|---|
| 0% | 0.00 |
| 10 wt % NB1038 | 0.50 |
| 10 wt % AM0281 | 0.50 |

Example 13

Adhesion was measured for a color layer formulation including the following components: Colorant, HEMA, HPMA, Di HEMA trimethylhexyl carbamate, Benzophenone-1, Diphenyl-2,4-trimethylbenzoyl phosphinic acid, Dimethicone, Polysilicone-13, PEG-2 Dimethicone, and Synthetic Wax, and for the same formulation with a 1:1 mixture of HEMA:POSS, or a 1:1 mixture of THFMA:POSS, added to give 10 wt % POSS in the final formulation.

| POSS | Avg. Adhesion Score |
|---|---|
| 0% | 0.83 |
| 10 wt % NB1038/THFMA | 2.83 |

Example 14

Peak strength and peel strength of a liquid-and-powder nail coating was measured by Hesiometer analysis. Samples were tested on a Romulus IIIA Hesiometer. Test method was set so each test allowed for 4.5 mm of travel with the blade set at 15° angle while applying 10 Newtons of force to the substrate.

Data was derived from a plot of force vs. displacement. To determine the data point for the peak or impact strength, the integral of the initial data peak was taken. To determine the data point for Peel or Adhesive Strength the, the integral of the plateau from 2.5 mm to 4.5 mm was taken.

| | Liquid and Powder | | Liquid with 5% POSS + Powder | |
|---|---|---|---|---|
| | Peak Strength | Peel Strength | Peak Strength | Peel Strength |
| Ave. | 219.6 | 159.25 | 1064.78 | 121.53 |
| Std. Dev. | 18.9 | 15.15 | 126.16 | 7.84 |
| % SDev. | 8.60 | 9.51 | 11.84 | 6.45 |

The test performed showed a great increase of Peak or Impact strength with the addition of the glycidyl POSS. After examination of the samples, the reduction of Peel strength may be a result of a delamination of the coating ahead of the blade due to the amount of force exerted during the Peak Strength measurement which can affect the peel strength measurement.

Example 15

Adhesion was measured for a series of water-based enamels, and for the same formulations with added POSS (EP0409). The water-based enamel used was a commercially available product that includes water, a styrene acrylates copolymer emulsion, an acrylate copolymer emulsion and colorants. The POSS was added directly to these formulations at levels of 1% and 5%.

| POSS | Average Dry Adhesion Score | Average Wet Adhesion Score |
|---|---|---|
| 0% | 2.5 | 0.17 |
| 1% POSS | 4.25 | 1.33 |
| 5% POSS | 3.67 | 1.50 |

What is claimed is:

1. A composition comprising:
   at least one reactive (meth)acrylate selected from the group consisting of hydroxypropyl methacrylate, hydroxyethyl methacrylate, ethyl methacrylate, tetrahydrofurfuryl methacrylate, pyromellitic dianhydride di(meth)acrylate, pyromellitic dianhydride glyceryl dimethacrylate, pyromellitic dimethacrylate, methacroyloxyethyl maleate, 2-hydroxyethyl methacrylate/succinate, 1,3-glycerol dimethacrylate/succinate adduct, phthalic acid monoethyl methacrylate, and mixtures thereof; and
   a polyhedral oligomeric silsesquioxane having the formula

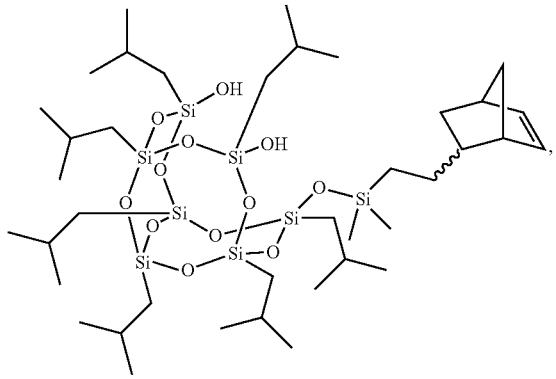

wherein the composition is a nail coating composition (i) providing enhanced adhesion to a surface of natural and/or artificial nails without pretreatment of the nail surface, or to a coated nail surface to promote the adhesion or interlaminar adhesion between various layers; and (ii) that remains wearable for at least five days and remains readily removable by use of a solvent.

2. The composition of claim 1, further comprising a film-forming polymer.

3. The composition of claim 2, wherein the film-forming polymer is selected from the group consisting of a cellulose ester, a cellulose acetate alkylate, a cellulose acetate butyrate, a cellulose acetate propionate, adipic acid/fumaric acid/phthalic acid/tricyclodecane dimethanol copolymer, adipic acid/neopentyl glycol/trimellitic anhydride copolymer, phthalic anhydride/trimellitic anhydride/glycols copolymer, polyethyl cellulose, polyhydroxypropyl cellulose, polyethyl acrylate oxide, poly-lactic acid, nitrocellulose, and mixtures thereof.

4. The composition of claim 1, further comprising a high-molecular weight (meth)acrylate polymer or copolymer having a molecular weight of at least about 1,000 g/mol.

5. The composition of claim 1, further comprising a polymethylmethacrylate-polymethylacrylic acid-copolymer.

6. The composition of claim 1, further comprising a solvent.

7. The composition of claim 6, wherein the solvent is a non-aqueous solvent.

8. The composition of claim 6, wherein the solvent is water.

9. The composition of claim 1, further comprising a polypropylene glycol (meth)acrylated monomer or a reactive polyethylene glycol (meth)acrylated monomer.

10. The composition of claim 1, further comprising a polymerization accelerator, a polymerization initiator, or a combination thereof.

11. The composition of claim 1, further comprising an adhesion promoter selected from the group consisting of hydroxypropyl methacrylate, hydroxyethyl methacrylate, ethyl methacrylate, tetrahydrofurfuryl methacrylate, pyromellitic dianhydride di(meth)acrylate, pyromellitic dianhydride glyceryl dimethacrylate, pyromellitic dimethacrylate, methacroyloxyethyl maleate, 2-hydroxyethyl methacrylate/succinate, 1,3-glycerol dimethacrylate/succinate adduct, phthalic acid monoethyl methacrylate, butyl methacrylate, isobutyl methacrylate, PEG-4 dimethacrylate, PPG monomethacrylate, trimethylolpropane trimethacrylate, isopropylidenediphenyl bisglycidyl methacrylate, lauryl methacrylate, cyclohexyl methacrylate, hexyl methacrylate, urethane methacrylate, triethylene glycol dimethacrylate, ethylene glycol dimethacrylate, tetraethylene glycol dimethacrylate, trimethylolpropane trimethacrylate, neopentylglycol dimethacrylate, acetoacetoxy methacrylate, acetoacetoxyethyl methacrylate, polyetheramine, glycidyl methacrylates, maleic anhydride, terpolymers containing vinyl acetate, organosilanes, organotitanates, chlorinated polyolefins, sucrose acetate isobutyrate, caprylic/capric triglyceride, glyceryl hydrogenated rosinate, pentaerythryl hydrogenated rosinate, styrene/methyl styrene/indene copolymer, blocked isocyanate PVC, polyamidoamine PVC, and a mixture thereof.

12. The composition of claim 1, further comprising at least one non-reactive, solvent dissolvable polymer selected from the group consisting of adipic acid/fumaric acid/phthalic acid/tricyclodecane dimethanol copolymer, adipic acid/neopentyl glycol/trimellitic anhydride copolymer, phthalic anhydride/trimellitic anhydride/glycols copolymer, polyethyl cellulose, polyhydroxypropyl cellulose, polyethyl acrylate oxide, poly-lactic acid, nitrocellulose, cellulose ester, and mixtures thereof.

13. The composition of claim 1, further comprising:
   at least one polymethylmethacrylate-polymethylacrylic acid copolymer;
   at least one non-reactive, solvent dissolvable polymer selected from the group consisting of adipic acid/fumaric acid/phthalic acid/tricyclodecane dimethanol copolymer, adipic acid/neopentyl glycol/trimellitic anhydride copolymer, phthalic anhydride/trimellitic anhydride/glycols copolymer, polyethyl cellulose, polyhydroxypropyl cellulose, polyethyl acrylate oxide, poly-lactic acid, nitrocellulose, cellulose ester, and mixtures thereof; and
   at least one non-reactive solvent selected from the group consisting of ketones, alkyl acetates, alcohols, alkanes, alkenes, and mixtures thereof.

* * * * *